US012703722B2

(12) United States Patent
Lasker et al.

(10) Patent No.: US 12,703,722 B2

(45) Date of Patent: Aug. 11, 2026

(54) POPTAG PEPTIDE AND USES THEREOF

(71) Applicants: CZ Biohub SF, LLC, San Francisco, CA (US); The Board of Trustees of the Leland Stanford Junior University, Stanford, CA (US)

(72) Inventors: Keren Lasker, Palo Alto, CA (US); Steven Boeynaems, Stanford, CA (US); Aaron David Gitler, Foster City, CA (US); Lucy Shapiro, Palo Alto, CA (US)

(73) Assignees: CZ Biohub SF, LLC, San Francisco, CA (US); The Board of Trustees of the Leland Stanford Junior University, California, CA (US)

( * ) Notice: Subject to any disclaimer, the term of this patent is extended or adjusted under 35 U.S.C. 154(b) by 944 days.

(21) Appl. No.: 17/782,366

(22) PCT Filed: Dec. 4, 2020

(86) PCT No.: PCT/US2020/063245
§ 371 (c)(1),
(2) Date: Jun. 3, 2022

(87) PCT Pub. No.: WO2021/113598
PCT Pub. Date: Jun. 10, 2021

(65) Prior Publication Data

US 2023/0044825 A1 Feb. 9, 2023

Related U.S. Application Data

(60) Provisional application No. 62/944,936, filed on Dec. 6, 2019.

(51) Int. Cl.

| | |
|---|---|
| ***A61K 39/00*** | (2006.01) |
| ***C07K 14/195*** | (2006.01) |
| ***C12N 15/62*** | (2006.01) |

(52) U.S. Cl.
CPC ............ *C07K 14/195* (2013.01); *C12N 15/62* (2013.01); *C07K 2317/622* (2013.01); *C07K 2319/735* (2013.01)

(58) Field of Classification Search
None
See application file for complete search history.

(56) References Cited

U.S. PATENT DOCUMENTS

| | | | |
|---|---|---|---|
| 2013/0017210 | A1 | 1/2013 | Peabody et al. |
| 2019/0144872 | A1 | 5/2019 | Gallo et al. |

(Continued)

FOREIGN PATENT DOCUMENTS

| | | | |
|---|---|---|---|
| WO | 9404678 | A1 | 3/1994 |
| WO | 2014191493 | A1 | 12/2014 |
| WO | 2015104406 | A2 | 7/2015 |

OTHER PUBLICATIONS

Nierman et al., "Complete genome sequence of Caulobacter crescentus," PNAS, vol. 98, No. 7: 4136-4141 (Year: 2001).*

(Continued)

*Primary Examiner* — M Franco G Salvoza
(74) *Attorney, Agent, or Firm* — Kilpatrick Townsend & Stockton LLP

(57) ABSTRACT

Proteins and fusion proteins for forming membraneless droplets in cells are provided. Described herein, is the development of a protein, named PopTag, that drives phase separation when it is part of a chimeric fusion protein. PopTag is engineered from the PopZ protein, found in a-proteobacteria (including *Caulobacter crescentus*). Despite PopZ being exclusively found in this clade of bacteria, the PopTag can drive protein phase separation in other prokaryotes (e.g., *E. coli*) and eukaryotes (e.g., human cells).

21 Claims, 7 Drawing Sheets

Specification includes a Sequence Listing.

(56) References Cited

U.S. PATENT DOCUMENTS

2019/0309312 A1* 10/2019 Ylera .................... C07K 16/32
2019/0322980 A1 10/2019 Bowman et al.

OTHER PUBLICATIONS

Lucchese et al., "How a single amino acid change may alter the immunological information of a peptide," Frontiers in Bioscience, E4 : 1843-1852 (Year: 2012).*
Rudikoff et al., "Single amino acid substitution altering antigen-binding specificity," Proc Natl Acad Sci USA 79:1979-1983 (Year: 1982).*
Lim et al., A PopZ-Linked Apical Recruitment Assay for Studying Protein-Protein Interactions in the Bacterial Cell Envelope, Molecular Microbiology, vol. 112, Issue 6, Dec. 2019, 21 pages.
Marks et al., The Genetic Basis of Laboratory Adaptation in Caulobacter Crescentus, Journal of Bacteriology, vol. 192, No. 14, Jul. 2010, pp. 3678-3688.
International Application No. PCT/US2020/063245, International Preliminary Report on Patentability mailed on Jun. 16, 2022, 9 pages.
International Application No. PCT/US2020/063245, International Search Report and Written Opinion mailed on May 20, 2021, 14 pages.
International Application No. PCT/US2020/063245, Invitation to Pay Additional Fees and, Where Applicable, Protest Fee mailed on Mar. 30, 2021, 2 pages.
Boeynaems et al., Protein Phase Separation: A New Phase in Cell Biology, Trends in Cell Biology, vol. 28, No. 6, Jun. 2018, pp. 420-435.
Bowman et al., Oligomerization and Higher-order Assembly Contribute to Sub-Cellular Localization of a Bacterial Scaffold, Molecular Microbiology, vol. 90, No. 4, Nov. 2013, pp. 1-32.
Nordyke et al., Intrinsically Disordered Bacterial Polar Organizing Protein Z, PopZ, Interacts with Protein Binding Partners Through an N-Terminal Molecular Recognition Feature, Journal of Molecular Biology, vol. 432, No. 23, Nov. 20, 2020, pp. 6092-6107.
Ali et al., Transferrin Trojan Horses as a Rational Approach for the Biological Delivery of Therapeutic Peptide Domains, The Journal of Biological Chemistry, vol. 274, No. 34, Aug. 20, 1999, pp. 24066-24073.
Altschul et al., Basic Local Alignment Search Tool, Journal of Molecular Biology, vol. 215, No. 3, Oct. 5, 1990, pp. 403-410.
Altschul et al., Gapped BLAST and Psi-Blast: A New Generation of Protein Database Search Programs, Nucleic Acids Research, vol. 25, No. 17, Sep. 1997, pp. 3389-3402.
Ausubel et al., Current Protocols in Molecular Biology, ringbou edition, Dec. 4, 2003, 4755 pages.
Azaldegui et al., The Emergence of Phase Separation as an Organizing Principle in Bacteria, Biophysical Journal, vol. 120, Apr. 6, 2021, pp. 1123-1138.
Banani et al., Biomolecular Condensates: Organizers of Cellular Biochemistry, Nature Reviews Molecular Cell Biology, vol. 18, No. 5, May 2017, pp. 285-298.
Banaszynski et al., A Rapid, Reversible, and Tunable Method to Regulate Protein Function in Living Cells Using Synthetic Small Molecules, Cell, vol. 126, No. 5, Sep. 8, 2006, pp. 995-1004.
Basile et al., Why Do Eukaryotic Proteins Contain More Intrinsically Disordered Regions?, Public Library of Science Computational Biology, vol. 15, No. 7, Jul. 22, 2019, pp. 1-20.
Bird et al., Single-Chain Antigen-Binding Proteins, Science, vol. 242, Oct. 21, 1988, pp. 423-426.
Boeynaems et al., Inside Out: The Role of Nucleocytoplasmic Transport in ALS and FTLD, Acta Neuropathologica, vol. 132, No. 2, Aug. 2016, pp. 159-173.
Boeynaems et al., Phase Separation of C9orf72 Dipeptide Repeats Perturbs Stress Granule Dynamics, Molecular Cell, vol. 65, No. 6, Mar. 16, 2017, pp. 1044-1055.
Boeynaems et al., Phosphorylation Leads the Way for Protein Aggregate Disassembly, Developmental Cell, vol. 45, No. 3, May 7, 2018, pp. 279-281.
Bowman et al., A Polymeric Protein Anchors the Chromosomal origin/ParB Complex at a Bacterial Cell Pole, Cell, vol. 134, No. 6, Sep. 19, 2008, pp. 945-955.
Bowman et al., Caulobacter PopZ Forms a Polar Subdomain Dictating Sequential Changes in Pole Composition and Function, Molecular Microbiology, vol. 76, No. 1, Apr. 2010, pp. 173-189.
Branon et al., Efficient Proximity Labeling in Living Cells and Organisms with TurboID, Nature Biotechnology, vol. 36, No. 9, Oct. 2018, doi: 10.1038/nbt.4201, Correction: Nature Biotechnology, vol. 38, No. 1, Jan. 2020, doi: 10.1038/s41587-019-0355-0, Oct. 2018, 45 pages.
Butler et al., Engineered Antibody Therapies to Counteract Mutant Huntingtin and Related Toxic Intracellular Proteins, Progress in Neurobiology, vol. 97, No. 2, May 2012, pp. 190-204.
Cohan et al., Making the Case for Disordered Proteins and Biomolecular Condensates in Bacteria, Trends in Biochemical Sciences, vol. 45, No. 8, Aug. 2020, pp. 1-13.
Dahlberg et al., Cryogenic Single-molecule Fluorescence Annotations for Electron Tomography Reveal in Situ Organization of Key Proteins in Caulobacter, Proceedings of the National Academy of Sciences, vol. 117, No. 25, Jun. 23, 2025, pp. 13937-13944.
Dye et al., Mutations in the Nucleotide Binding Pocket of MreB Can Alter Cell Curvature and Polar Morphology in Caulobacter, Molecular Microbiology, vol. 81, No. 2, Jul. 2011, pp. 368-394.
Ebersbach et al., A Multimeric Pole-organizing Protein Critical for Chromosome Attachment, Division and Protein Localization in Caulobacter, Cell, vol. 134, No. 6, Sep. 19, 2008, pp. 956-968.
Franzmann et al., Protein Phase Separation as a Stress Survival Strategy, Cold Spring Harbor Perspectives in Biology, vol. 11, No. 6, Jun. 2019, pp. 1-18.
Guntas et al., Engineering an Improved Light-induced Dimer (iLID) for Controlling the Localization and Activity of Signaling Proteins, Proceedings of the National Academy of Sciences, vol. 112, No. 1, Jan. 6, 2015, pp. 112-117.
Harris et al., A Caulobacter MreB Mutant with Irregular Cell Shape Exhibits Compensatory Widening to Maintain a Preferred Surface Area to vol. Ratio, Molecular Microbiology, vol. 94, No. 5, Dec. 2014, pp. 988-1005.
Henikoff et al., Amino Acid Substitution Matrices from Protein Blocks, Proceedings of the National Academy of Sciences, vol. 89, No. 22, Nov. 15, 1992, pp. 10915-10919.
Hey et al., Artificial, Non-antibody Binding Proteins for Pharmaceutical and Industrial Applications, Trends in Biotechnology, vol. 23, No. 10, Oct. 10, 2005, pp. 514-522.
Hofmann et al., Polymer Scaling Laws of Unfolded and Intrinsically Disordered Proteins Quantified with Single- molecule Spectroscopy, Proceedings of the National Academy of Sciences, vol. 109, No. 40, Oct. 2, 2012, pp. 16155-16160.
Holmes et al., Caulobacter PopZ Forms an Intrinsically Disordered Hub in Organizing Bacterial Cell Poles, Proceedings of the National Academy of Sciences, vol. 113, No. 44, Nov. 2016, p. 12490-12495.
Huston et al., Protein Engineering of Antibody Binding Sites: Recovery of Specific Activity in an Anti-Digoxin Single-Chain Fv Analogue Produced in *Escherichia Coli*, Proceedings of the National Academy of Sciences of the United States of America, vol. 85, No. 16, Aug. 1988, pp. 5879-5883.
Karlin et al., Applications and Statistics for Multiple High-Scoring Segments in Molecular Sequences, Proceedings of the National Academy of Sciences, vol. 90, No. 12, Jun. 15, 1993, pp. 5873-5877.
Kato et al., Cell-free Formation of RNA Granules: Low Complexity Sequence Domains Form Dynamic Fibers Within Hydrogels, Cell, vol. 149, No. 4, May 11, 2012, pp. 753-767.
Kubala et al., Structural and Thermodynamic Analysis of the GFP: GFP-nanobody Complex, Protein Science, vol. 19, No. 12, Dec. 2010, pp. 2389-2401.
Lambrus et al., Applying the Auxin-inducible Degradation System for Rapid Protein Depletion in Mammalian Cells, In Methods in Cell Biology, vol. 144, Jan. 2018, pp. 107-135.

(56) References Cited

OTHER PUBLICATIONS

Lasker et al., An Intracellular Compass Spatially Coordinates Cell Cycle Modules in Caulobacter Crescentus, Current Opinion in Microbiology, vol. 33, Oct. 2016, pp. 131-139.
Lasker et al., Selective Sequestration of Signaling Proteins in a Membraneless Organelle Reinforces the Spatial Regulation of Asymmetry in Caulobacter Crescentus, Nature Microbiology, vol. 5, No. 3, Mar. 2020, pp. 418-429.
Ma et al., Unstructured mRNAs form Multivalent RNA-RNA Interactions to Generate TIS Granule Networks, Available Online at: https://www.biorxiv.org/content/biorxiv/early/2020/Feb. 18, 2020. 02.14.949503.full.pdf, Feb. 2020, pp. 1-15.
Marsh et al., Sequence Determinants of Compaction in Intrinsically Disordered Proteins, Biophysical Journal, vol. 98, No. 10, May 19, 2010, pp. 2383-2390.
Martin et al., Intrinsically Disordered Protein Regions and Phase Separation: Sequence Determinants of Assembly or Lack Thereof, Emerging Topics in Life Sciences, vol. 4, No. 3, Dec. 2020, pp. 307-329.
Mathieu et al., Beyond Aggregation: Pathological Phase Transitions in Neurodegenerative Disease, Science, vol. 370, Oct. 2, 2020, pp. 56-60.
Molliex et al., Phase Separation by Low Complexity Domains Promotes Stress Granule Assembly and Drives Pathological Fibrillization, Cell, vol. 163, No. 1, Sep. 24, 2015, pp. 123-133.
Needleman et al., A General Method Applicable to the Search for Similarities in the Amino Acid Sequence of Two Proteins, Journal of Molecular Biology, vol. 48, No. 3, Mar. 28, 1970, pp. 443-453.
Patel et al., A Liquid-to-solid Phase Transition of the ALS protein FUS Accelerated by Disease Mutation, Cell, vol. 162, No. 5, Aug. 27, 2015, pp. 1066-1077.
Pearson et al., Improved Tools for Biological Sequence Comparison, Proceedings of the National Academy of Sciences, vol. 85, No. 8, Apr. 1988, pp. 2444-2448.
Ramaswami et al., Altered Ribostasis: RNA-protein Granules in Degenerative Disorders, Cell, vol. 154, No. 4, Aug. 15, 2013, pp. 727-736.
Sambrook et al., Molecular Cloning: A Laboratory Manual, Third Edition, vol. 1, 2001, 2272 pages.
Scheckel et al., Prions, Prionoids and Protein Misfolding Disorders, Nature Reviews Genetics, vol. 19, No. 7, Jul. 2018, pp. 405-418.
Shin et al., Liquid Nuclear Condensates Mechanically Sense and Restructure the Genome, Cell, vol. 175, No. 6, Nov. 29, 2018, pp. 1481-1491.
Shin et al., Liquid Phase Condensation in Cell Physiology and Disease, Science, vol. 357, No., 6357, Sep. 22, 2017, 13 pages.
Shin et al., Spatiotemporal Control of Intracellular Phase Transitions using Light-activated Optodroplets, Cell, vol. 168, No. 1, Jan. 12, 2017, pp. 1-13.
Smith et al., Comparison of Biosequences, Advances in Applied Mathematics, vol. 2, No. 4, Dec. 1981, pp. 482-489.
Sorensen et al., Effective Concentrations Enforced by Intrinsically Disordered Linkers Are Governed by Polymer Physics, Proceedings of the National Academy of Sciences, vol. 116, No. 46, Nov. 12, 2019, p. 23124-23131.
Van Der Lee et al., Classification of Intrinsically Disordered Regions and Proteins, Chemical Reviews, vol. 114, No. 13, Jul. 9, 2014, pp. 6589-6631.
Vanneste et al., C9orf72-generated poly-GR and poly-PR Do Not Directly Interfere with Nucleocytoplasmic Transport, Scientific Reports, vol. 9, No. 1, Oct. 31, 2019, pp. 1-10.
Wiegand et al., Drops and Fibers-how Biomolecular Condensates and Cytoskeletal Filaments Influence Each Other, Emerging Topics in Life Sciences, vol. 4, No. 3, Oct. 13, 2020, doi: 10.1042/ETLS20190174; Correction: Emerging Topics in Life Sciences, vol. 4, No. 3, Dec. 11, 2020, doi: 10.1042/ETLS20190174_COR, Oct. 13, 2020, 17 pages.
Woerner et al., Cytoplasmic Protein Aggregates Interfere with Nucleocytoplasmic Transport of Protein and RNA, Science, vol. 351, Jan. 8, 2016, pp. 173-176.
Yoo et al., Cellular sensing by phase separation: Using the process, not just the products, Journal of Biological Chemistry, vol. 294, No. 18, May 2019, pp. 7151-7159.
Zhang et al., Stress Granule Assembly Disrupts Nucleocytoplasmic Transport, Cell, vol. 173, No. 4, May 3, 2018, pp. 958-971.
Zhao et al., Transforming Activity of an Oncoprotein-Encoding Circular RNA from Human Papillomavirus, Nature Communications, vol. 10, No. 1, May 24, 2019, doi: 10.1038/s41467-019-10246-5; Correction: Nature Communications, vol. 13, No. 1, May 18, 2022, doi: 10.1038/s41467-022-30659-z, May 24, 2019, 13 pages.

* cited by examiner

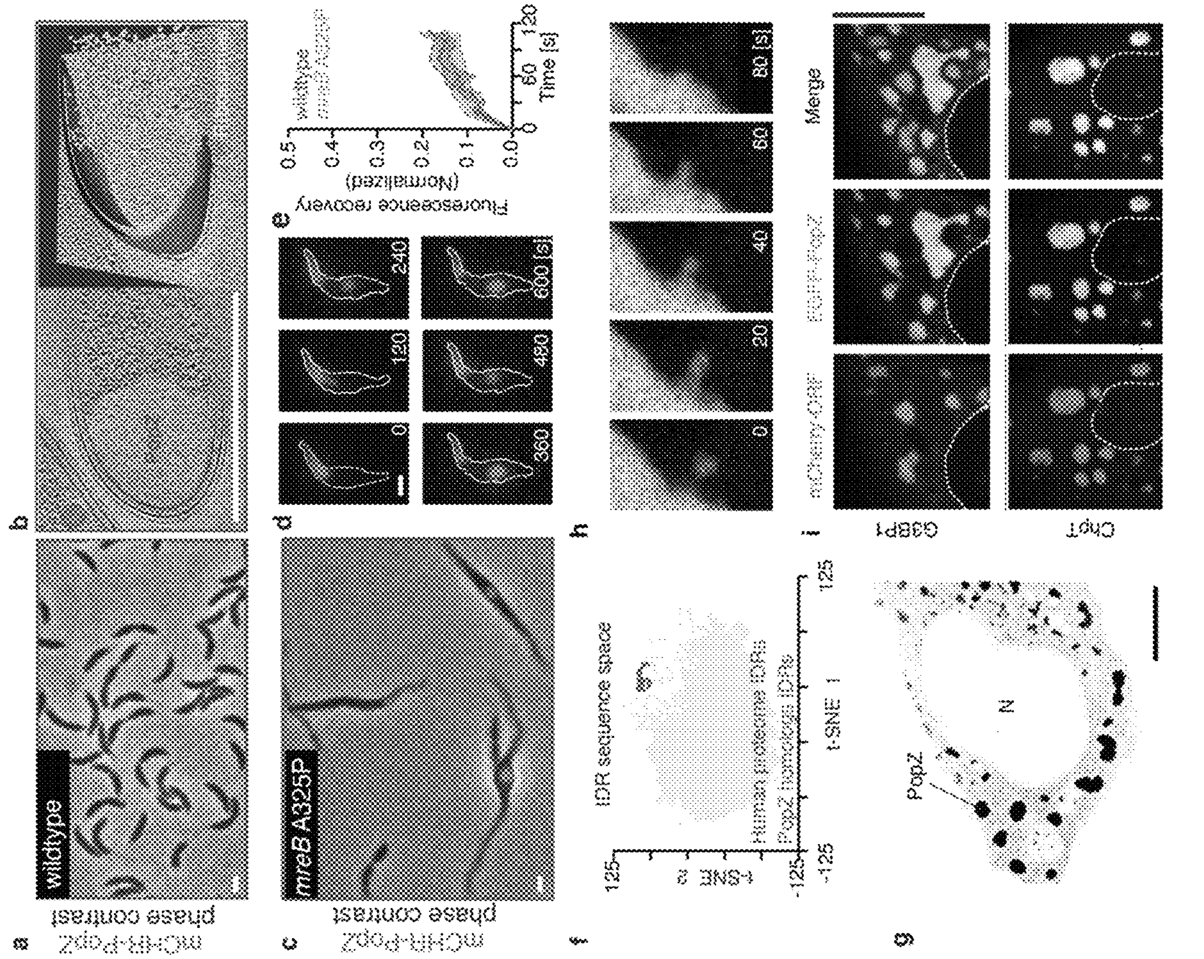
FIG. 1a-i

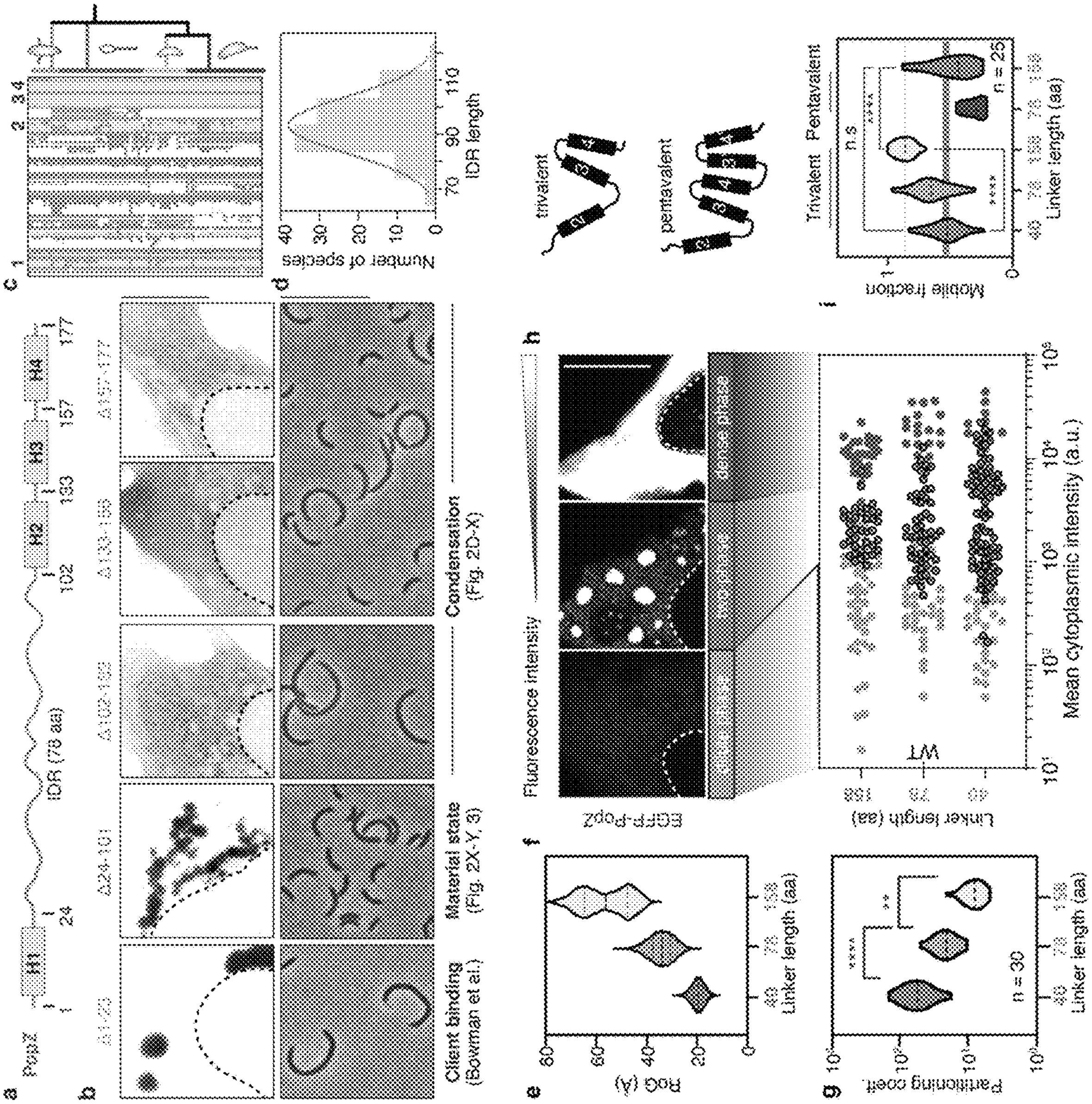
FIG. 2a-i

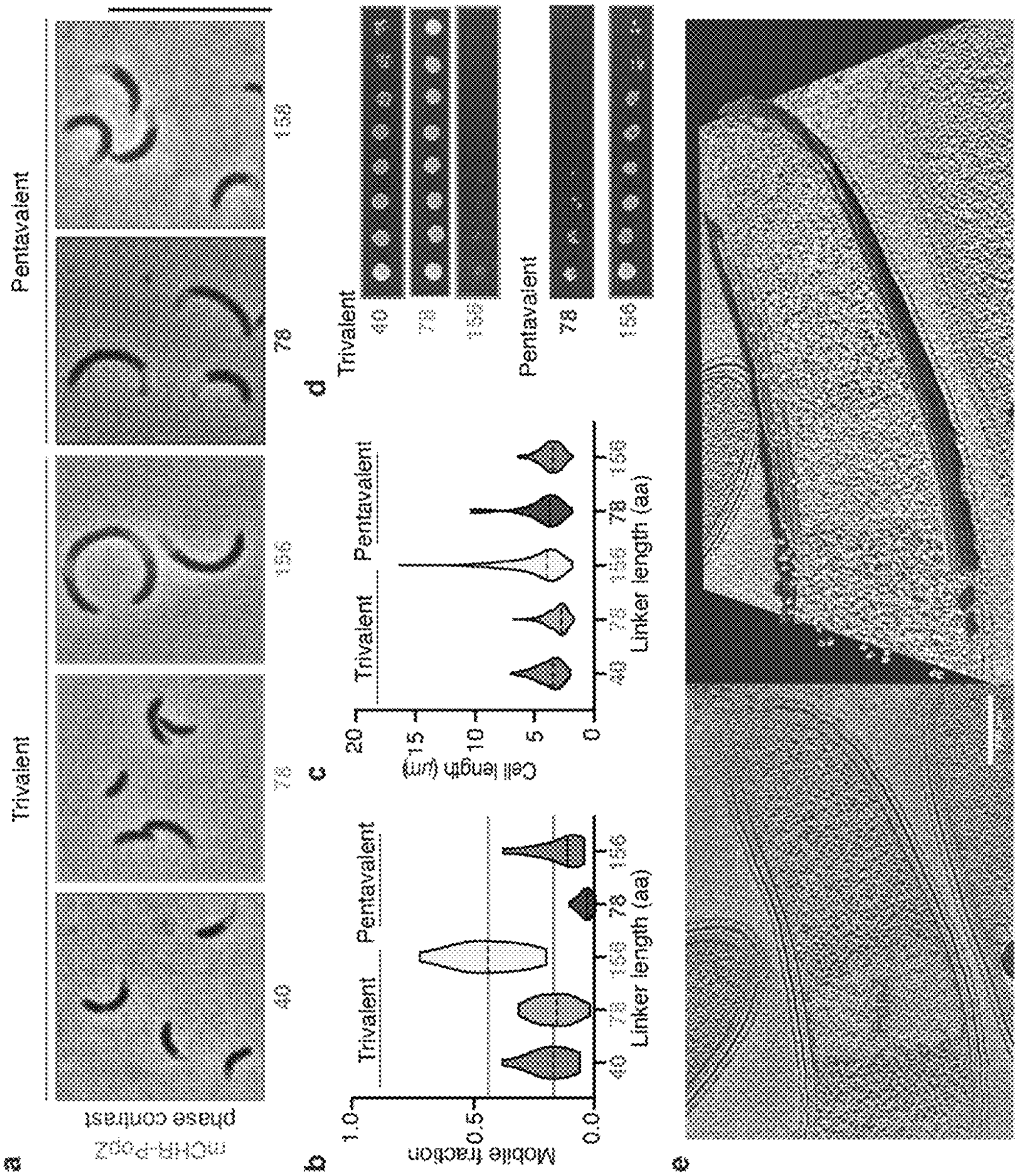
FIG. 3a-e

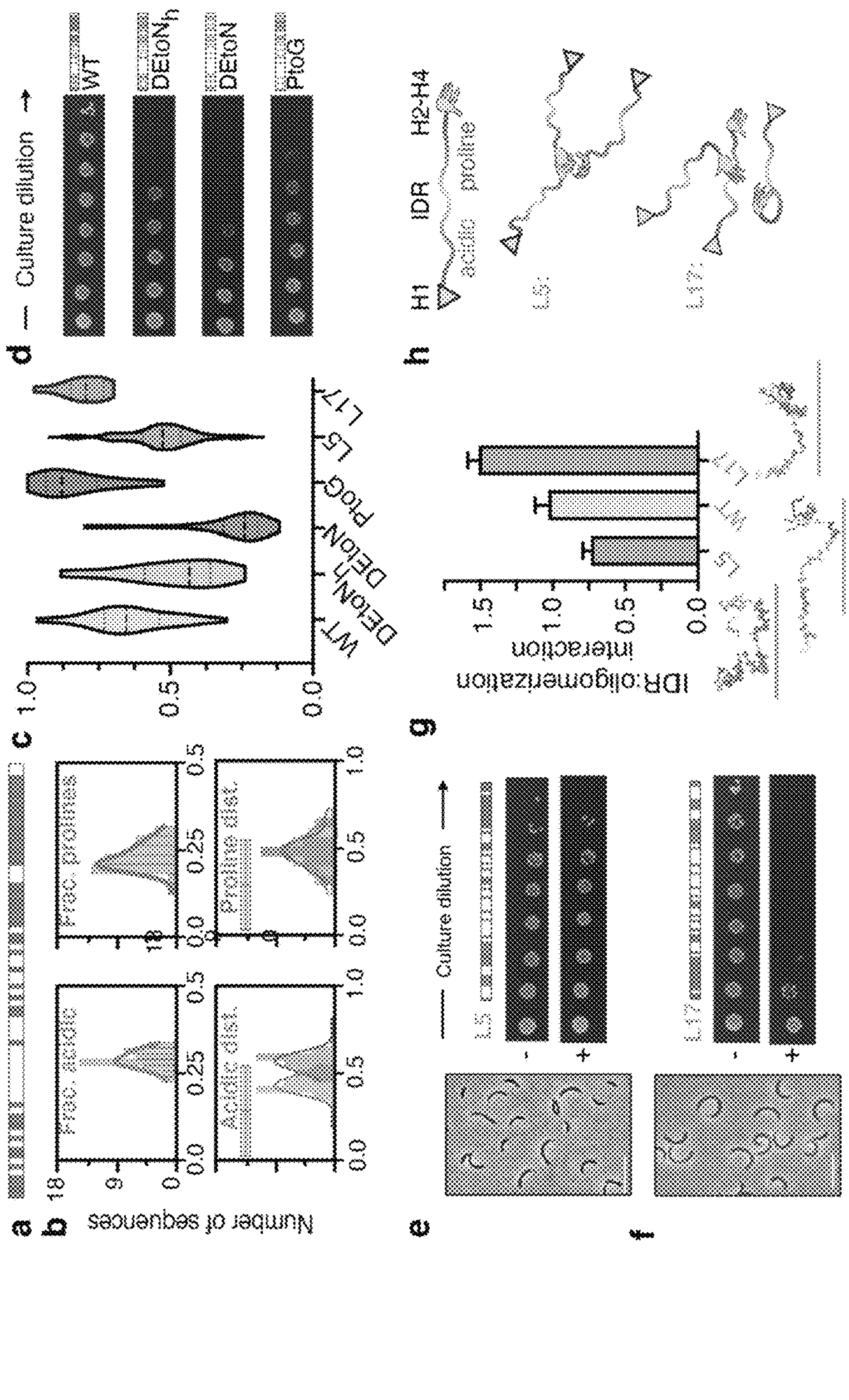
FIG. 4a-h

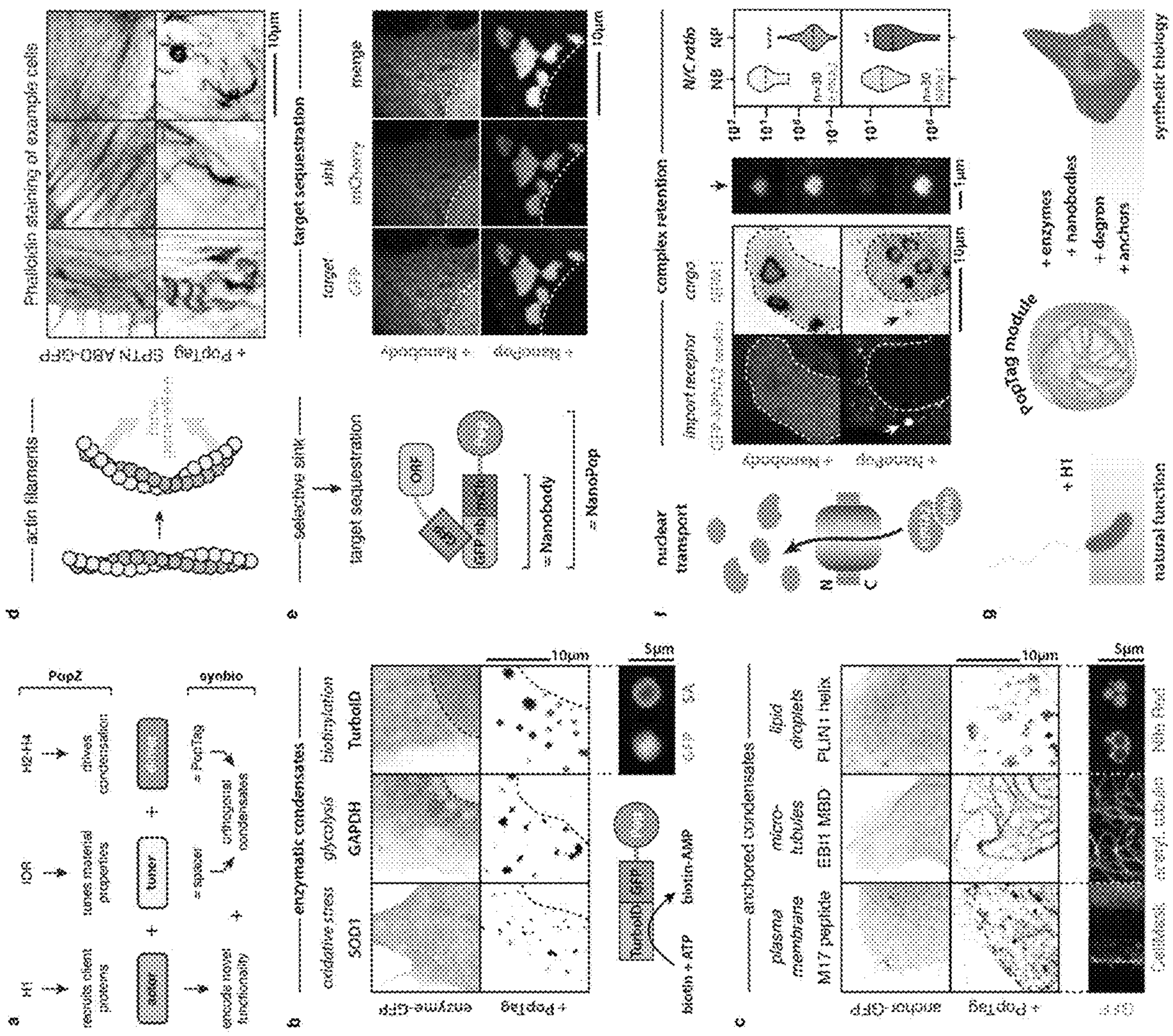
FIG. 5a-g

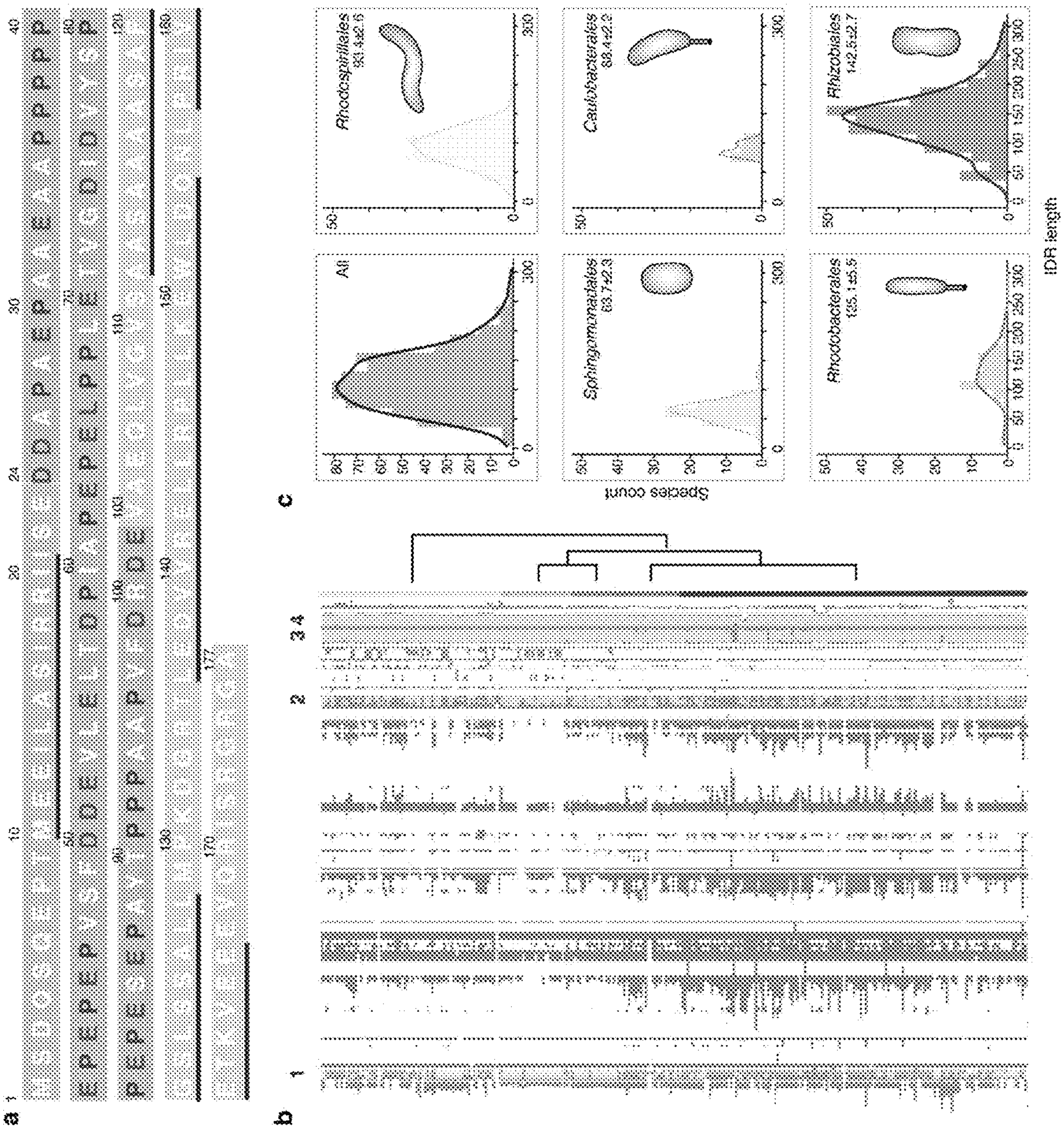
FIG. 6a-c

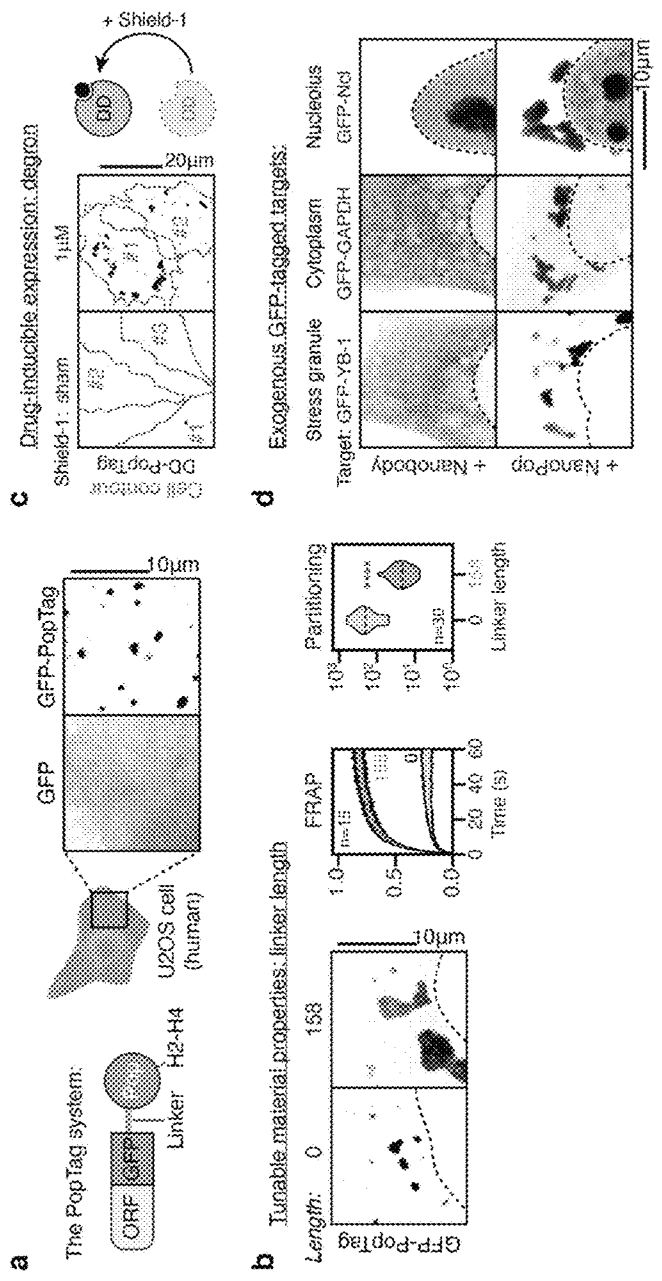
FIG. 7a-d

POPTAG PEPTIDE AND USES THEREOF

CROSS-REFERENCE TO RELATED PATENT APPLICATIONS

The present is a national phase application of PCT Application No. PCT/US2020/063245, filed Dec. 4, 2020, which claims benefit of priority to U.S. Provisional Patent Application No. 62/944,936, filed Dec. 6, 2019, which is are incorporated by reference for all purposes.

STATEMENT AS TO RIGHTS TO INVENTIONS MADE UNDER FEDERALLY SPONSORED RESEARCH AND DEVELOPMENT

This invention was made with Government support under contracts GM1 18071 and NS097263, awarded by the National Institutes of Health. The Government has certain rights in the invention.

SEQUENCE LISTING

The contents of the electronic sequence listing (103182-1215678-003810WO_SL.txt; Size: 112,959 bytes; and Date of Creation: Jan. 15, 2021) is herein incorporated by reference in its entirety.

BACKGROUND OF THE INVENTION

Cellular compartments and organelles organize biological matter. Most well-known organelles are separated by a membrane boundary from their surrounding milieu. There are also many membraneless organelles and recent studies suggest that these organelles, which are supramolecular assemblies of proteins and RNA molecules, form via protein phase separation. See, e.g., Boeynaems, et al., *Trends Cell Biol.* 2018 June;28(6):420-435.

BRIEF SUMMARY OF THE INVENTION

We describe the development of a protein, named PopTag, that drives phase separation when it is part of a chimeric fusion protein. PopTag is engineered from the PopZ protein, found in a-proteobacteria (including *Caulobacter crescentus*). Despite PopZ being exclusively found in this clade of bacteria, the PopTag can drive protein phase separation in other prokaryotes (e.g., *E. coli*) and eukaryotes (e.g., human cells).

The resulting protein droplets can be tuned in a variety of ways:

1. Material properties range from liquid to solid, depending on the addition of a negatively charged protein and/or proline-rich linker.
2. Inducible degradation, e.g., using degron systems.
3. Fluorescent imaging using fluorescent protein fusions.
4. Cellular localization via fusion to different protein domains.
5. Functionality via enzyme fusions.
6. Target recruitment, e.g., via binding domain fusions or the use of nanobodies.

The use of this protein tag includes, but is not limited to:

1. Recombinant protein purification as phase-separated bodies.
2. Generation of enzymatic nanoparticles as catalysts.
3. Generation of synthetic protein droplets in both prokaryote and eukaryote cells and organisms, including but not limited to bacteria, yeast, plant cells and mammalian cells, e.g., for the study of phase separation in vivo as well as any bioengineering application that uses the PopTag.
4. Sequestering toxic protein and RNA species in the cytoplasm of cells, for example, those proteins and RNA species associated with neurodegenerative disorders or viral infections, by fusing PopTag to a nanobody or other epitope-binding polypeptide, which is raised against a specific toxin or against a specific viral protein. By sequestering the toxic protein or RNA species in the compartment (which may be formed in, for example, the cytoplasm, Golgi, or endoplasmic reticulum) created by PopTag, the effects or action of the protein or RNA are removed from the cell. This sequestration can provide therapeutic benefits to the cell and the cellular host, e.g., a patient.
5. Sequestration of functional factors to perturb cellular pathways.
6. Compartmentalization of enzymatic reactions to optimize yield, specificity, and off-target reactions.

In some embodiments, a fusion protein is provided comprising an amino acid sequence linked to a polypeptide sequence comprising SEQ ID NO: 1, or a variant thereof as set forth in Table 1, wherein the amino acid sequence is heterologous to the polypeptide sequence. The terms "amino acid sequence" and "polypeptide sequence" both refer to chains of amino acids and are used merely to differentiate the two as different sequences for antecedent basis purposes. In some embodiments, the polypeptide sequence is substantially (e.g., at least 60%, 70%, 80%, 90%, or 95%) identical to SEQ ID NO:1.

In some embodiments, the amino acid sequence is an epitope-binding polypeptide. In some embodiments, the epitope-binding polypeptide comprises an immunoglobin heavy chain variable region. In some embodiments, the epitope-binding polypeptide is a single domain antibody (e.g., nanobody) or a single-chain variable fragment (scfv).

In some embodiments, the amino acid sequence is a target-binding polypeptide.

In some embodiments, the amino acid sequence comprises a fluorescent protein.

In some embodiments, the amino acid sequence comprises an enzyme.

Also provided is a polynucleotide comprising a nucleic acid sequence that encodes the fusion protein as described above or elsewhere herein. In some embodiments, the polynucleotide comprises a promoter operably linked to the nucleic acid sequence.

Also provided is a truncated PopZ polypeptide comprising SEQ ID NO: 1, or a variant thereof as set forth in Table 1. In some embodiments, the polypeptide sequence is substantially (e.g., at least 60%, 70%, 80%, 90%, or 95%) identical to SEQ ID NO:1 or any one of SEQ ID NO: 4-149 or comprises such a sequence.

Also provided is a cell comprising a polynucleotide encoding the fusion protein as described above or elsewhere herein, wherein the cell expresses the fusion protein. In some embodiments, the cell is a eukaryotic cell. In some embodiments, the eukaryotic cell is a mammalian (e.g., human) cell. In some embodiments, the eukaryotic cell is a plant or yeast cell.

In some embodiments, the cell comprises: a. a first polynucleotide encoding a first fusion protein and; b. a second polypeptide encoding a second fusion protein, wherein the first fusion protein and the second fusion protein comprise a polypeptide sequence comprising SEQ ID NO: 1 or a variant thereof as set forth in Table 1 and comprise different heterologous amino acid sequences. In some embodiments, the polypeptide sequence is substantially (e.g., at least 60%, 70%, 80%, 90%, or 95%) identical to SEQ ID NO:1 or any one of SEQ ID NO: 4-149. In some embodiments, the different heterologous amino acid sequences are different enzymes.

Also provided are methods of purifying a product from a cell. In some embodiments, the method comprises expressing in the cell the fusion protein as described above or elsewhere herein, wherein the fusion protein forms compartments in the cell; optionally performing a reaction in the compartments to form the product; lysing the cell; and isolating the compartments from cell lysate material, wherein the compartments comprise the product, thereby purifying the product from the cell. In some embodiments, the product is formed by performing a product in the compartments. In some embodiments, the amino acid sequence comprises an enzyme and the enzyme catalyzes production of the product. In some embodiments, the cell produces the product and the amino acid sequence comprises a binding polypeptide that binds the product, thereby binding the product to the compartment. In some embodiments, the product is the fusion protein.

Also provided is a method of expressing the fusion protein as described above or elsewhere herein in a cell. In some embodiments, the method comprises introducing into the cell an expression cassette comprising a promoter operably linked to a polynucleotide encoding the fusion protein; wherein the fusion protein is expressed in the cell.

BRIEF DESCRIPTION OF THE DRAWINGS

FIG. 1*a-i*. PopZ phase separates in *Caulobacter crescentus* and human U2OS cells.

FIG. 1*a*. PopZ self-assembles at the poles of wild-type *Caulobacter* cells. A fluorescent image of ΔpopZ *Caulobacter* cells expressing mCherry-PopZ from the xylX promoter on a high copy plasmid overlaid on a corresponding phase-contrast image. Scale bar, 1 m FIG. 1*b*. The PopZ microdomain excludes ribosomes and forms a sharp convex boundary. (left) Slice through a tomogram of a cryo-ET focused ion beam-thinned ΔpopZ *Caulobacter* cell overexpressing mCherry-PopZ. A dashed red line shows the boundaries of the PopZ region. (right) Segmentation of the tomogram in (left) showing the outer membrane, inner membrane (light brown), and ribosomes. Scale bar, 1 μm. FIG. 1*c-d*. PopZ creates droplets in deformed *Caulobacter* cells. FIG. 1*c*. A fluorescent image of *Caulobacter* cells bearing a mreB A325P mutant, expressing mCherry-PopZ from the xylX promoter on a high copy plasmid overlaid on a corresponding phase-contrast image. Scale bar, 1 μm. FIG. 1*d*. Fluorescent images showing the PopZ microdomain extending into the cell body, concurrent with the thinning of the polar region, producing a droplet that dynamically moves throughout the cell. Frames are two minutes apart. Scale bar, 1 μm. FIG. 1*e*. PopZ dynamics are not affected by a release from the cell pole. Recovery following targeted photobleaching of a portion of an extended PopZ microdomain in wild-type and mreB A325P mutant cells. Cells expressing mCherry-PopZ from a high copy plasmid were imaged for 12 frames of laser scanning confocal microscopy following targeted photobleaching with high-intensity 561 nm laser light. Shown is the mean±SEM of the normalized fraction of recovered signal in the bleached region; n equals 15 cells. FIG. if. IDRs of PopZ homologs cluster separately from IDRs within the human proteome. t-SNE mapping of IDR sequence composition. Each data point corresponds to the sequence composition of a single IDR. In gray are IDRs from the human proteome, and in red are IDRs from PopZ homologs within the Caulobacterales order. FIG. 1*g*. *Caulobacter* PopZ expressed in human U20S cells forms phase-separated condensates in the cytoplasm, but not the nucleus (N). FIG. 1*h*. In vivo fusion and growth of PopZ condensates in human U20S cells. 80 seconds time-lapse images of a small PopZ condensate merging with a large PopZ condensate. Scale bar, 10 μm. FIG. 1*i*. PopZ expressed in human U20S cells retains selectivity. (Top) EGFP-PopZ and stress granule protein mCherry-G3BP1 form separate condensates. (Bottom) EGFP-PopZ recruits the *Caulobacter* phosphotransfer protein mCherry-ChpT when co-expressed in human U20S cells. Scale bar, 10 m.

FIG. 2*a-i*. Modular organization regulates the dynamics of the PopZ condensate. FIG. 2*a*. Domain organization of the PopZ protein from *Caulobacter crescentus*. PopZ is composed of a short N-term region with a predicted helix, H1 (gray box), a 78 amino-acid intrinsically disordered region (IDR, curly line), and a C-term region with three predicted helices, H2, H3, H4. FIG. 2*b*. Region deletion and its effect on PopZ condensation. (top) GFP fused to five PopZ deletions expressed in human U20S cells. (bottom) mCherry fused to four PopZ deletions (Δ1-23, Δ24-101, Δ102-132, and Δ133-177) expressed in 4popZ *Caulobacter* cells. FIG. 2*c*. conservation of the PopZ protein regions. Graphical representation of a multiple alignment of 99 PopZ homologs within the Caulobacterales order. Each row corresponds to a PopZ homolog and each column to an alignment position. All homologs encode an N-terminal region, an IDR, and a C-terminal helical region. White regions indicate alignment gaps, and gray regions indicate predicted helices 1 to 4. Phylogeny tree of the corresponding species is shown, highlighting the four major genera in the Caulobacterales order: Asticcacaulis, *Brevundimonas*, Phenylobacterium, and *Caulobacter*. Notably, all species within the *Brevundimonas* genus code for insertion between helix 2 and helix 3. FIG. 2*d*. Conserved linker length within the Caulobacterales order. A histogram of the length of the linker of 99 PopZ homologs. The mean length is 93.6 aa with s.e.m of 1.1. FIG. 2*e*. Linker length and its effect on the radius of gyration. The predicted radius of gyration for a half linker (IDR-40, 40 aa),full wild-type linker (IDR-78, 78 aa), and a double linker (IDR-156, 156 aa). FIG. 2*f*. Phase diagram of PopZ expressed in Human U2OS cells. (top) Three states of PopZ condensation: diffuse PopZ (dilute phase, left), PopZ condensates (two-phase, i.e., a diffused phase and condensed phase, middle) and a single condensate that fills most of the cytoplasm (dense phase, right). A color gradient indicates EGFP fluorescence intensity from (low) to (high). The nucleus boundary is shown as a white dotted line. (bottom) Phase diagrams of EGFP fused to PopZ with IDR-40, IDR-78, and IDR-156. Each dot represents data from a single cell, positioned on the x-axis as a function of the cell mean cytoplasmic intensity. The color of the dot indicates its phase, a dilute phase, two-phase, or dense phase. FIG. 2*g*. Quantification of the partition coefficient, i.e., the ratio of the total concentration in the condensed phase to that in the protein-dilute phase, of each of the three linkers. A higher partitioning coefficient indicates denser condensates. Four (two) asterisks indicate four (two) fold difference. FIG. 2*h*. Schematics of the oligomerization domain of the wild-type PopZ (trivalent, left) and an oligomerization domain with increased valency consisting of five helices, with a repeat of helices 3 and 4 (pentavalent, right). FIG. 2*i*. Balance between condensation promoting and counteracting phase separation tunes condensate material properties. FRAP, shown as mobile fractions, the plateau of the FRAP curves, for PopZ with its wild-type oligomerization domain (trivalent) and a linker of three different lengths, as well as PopZ with an extended oligomerization domain (pentavalent) with IDR-78 and IDR-156.

FIG. 3*a-e*. IDR length and OD valency affect *Caulobacter* viability. FIG. 3*a*. Linker length and its effect on condensate localization in *Caulobacter*. ΔpopZ *Caulobacter* cells expressing mCherry fused to PopZ with an IDR of different lengths and either a trivalent or a pentavalent c-terminal region. mCherry-PopZ with IDR-40 or the wild-type IDR-78 maintains its localization at the poles of the cell, while mCherry-PopZ with IDR-156 demonstrates condensates throughout the cytoplasm. The mutants of PopZ with pentavalent c-term both show polar localization. Scale bar, 10 μm. FIG. 3*b*. Balance between condensation promoting and obstructing tunes material properties. A violin plot of the distribution of FRAP measurements for the different mutants. FRAP, shown as mobile fractions, for PopZ with its wild-type oligomerization domain (trivalent) and a linker of three different lengths, as well as PopZ with an extended oligomerization domain (pentavalent) with IDR-78 and c. FIG. 3*c*. Cell length for the different mutants. A violin plot of the distribution of cell lengths for the different mutants. At least 30 cells were measured for each condition. FIG. 3*d*. Serial dilutions of PopZ mutants in a ΔpopZ background. Spotting on M2G plates with 0.06% xylose is shown after three days of incubation. FIG. 3*e*. PopZ IDR-156 condensates retain ribosome exclusion. (left) Slice through a tomogram of a cryo-focused ion beam-thinned ΔpopZ *Caulobacter* cell overexpressing mCherry-PopZ with IDR-156. (right) Segmentation of the tomogram in (left) showing annotated outer membrane, inner membrane, and ribosomes. Scale bar, 0.25 μm.

FIG. 4*a-h*. The IDR net charge and charge distribution are conserved and tune the material properties of the PopZ condensate. FIG. 4*a*. The PopZ IDR is enriched with acidic residues and prolines. Schematic of the wild-type PopZ IDR showing acidic residues (28%), prolines (29%), and all other residues (43%). FIG. 4*b*. The sequence composition of the PopZ IDR is conserved across Caulobacterales. Histograms are calculated across 99 PopZ homologs within the Caulobacterales order and show a tight distribution for the following four parameters. (top, left) The mean fraction of acidic residues is 0.29±0.004. (top, right) The mean fraction of prolines is 0.23±0.006. (bottom, left) Among the acidic residues within the IDR, the fraction of those found in the N-terminal half (0.57±0.011) and the C-terminal half of the IDR (0.43±0.011). (bottom, right) Among the prolines within the IDR, the fraction of those found in the N-terminal half (0.5±0.015) and the C-terminal half of the IDR (0.5±0.015). FIG. 4*c*. Amino acid composition plays a role in PopZ viscosity. FRAP, shown as mobile fractions, for PopZ with its wild-type IDR and five mutants: Substituting either half or all of the acidic residues for asparagine (DEtoNh and DEtoN, respectably), substituting all prolines for glycines (PtoG), and moving all acidic residues to either the N-terminal part or the C-terminal part of the linker (L17 and L5, respectably). FIG. 4*d*. Serial dilutions of *Caulobacter* cells expressing mutant PopZ in a popZ background e-f. Charge polarity affects PopZ liquidity. Data shown for two extreme linkers, scramble L5 and scramble L17, which exhibit opposing acidity at the N and C termini of the PopZ IDR. FIG. 4*e*. Replacing wild-type PopZ with L5 in *Caulobacter* does not show a phenotype in cell length (left) or growth (right). FIG. 4*f*. Replacing wild-type PopZ with L17 leads to filamentous cells (left) and close to no growth (right). FIG. 4*g*. Competition between intra and inter PopZ interactions. Plotted is the percentage of PopZ conformations with IDR/OD interactions throughout an all-atoms simulation trajectory of either wild-type PopZ, PopZ with L5 IDR, or PopZ with L17 IDR. Snapshots from the three simulations are shown in the bottom.

FIG. 4*h*. Visualization of the binding competition model. FIG. 5*a-g*: An engineered PopTag phase separates into cytoplasmic condensates with tunable material properties. FIG. 5*a*. Re-engineering PopZ as a modular platform for the generation of designer condensates. The PopTag drives phase separation, the spacer tunes material properties, and the actor domain determines functionality. FIG. 5*b*. The PopTag fusion allows the condensation of enzymes. TurboID maintains biotinylation activity within PopTag condensates, indicated by the biotin signal inside PopTag condensates after the addition of biotin to the cell medium. Biotin was detected by streptavidin (SA) staining. FIG. 5*c*. Subcellular anchors control PopTag condensate localization. M17 peptide derived from HIV Gag protein, microtubule-binding domain (MBD) from EBII, amphipathic helix from PLIN1. CellMask labels the plasma membrane, acetylated tubulin the microtubules, and Nile Red lipid droplets. FIG. 5*d*. Condensation of the PopTag on actin filaments by actin-binding domain fusion (SPTN2) drives coalescence, buckling, and bending of actin filaments (phalloidin staining). FIG. 5*e*. NanoPop is the fusion of the PopTag to a GFP-targeting nanobody and allows the recruitment of GFP (-tagged proteins) into condensates. Nanobody and NanoPop are labeled with mCherry. FIG. 5*f*. NanoPop condensates trap endogenously GFP-tagged KPNA2 in the cytoplasm of HAP1 cells, together with its client cargo protein NPM1. Violin plots show the quantification of nucleo-cytoplasmic ratios. n is the number of cells. Mann-Whitney.  p-value=0.01,  p-value=0.0001. FIG. 5***g*. Scheme highlighting how different actor domains drive PopZ/PopTag function in nature or synthetic biology.

FIG. 6*a-c*. PopZ sequence across alpha-proteobacteria. FIG. 6*a*. PopZ primary sequence. The N-terminal, IDR, and C-terminal regions. Within the IDR, prolines and negatively charged residues. Rectangles indicate the boundaries of predicted α-helices. FIG. 6*a* discloses SEQ ID NO: 152. FIG. 6*b*. Conservation of the PopZ protein regions within α-proteobacteria. Graphical representation of multiple alignment of 655 PopZ homologs across α-proteobacteria. Each row corresponds to a PopZ homolog and each column to an alignment position. All homologs encode an N-terminal region, an IDR, a C-terminal helical region. White regions indicate alignment gaps, and gray regions indicate predicted helices 1 to 4. Phylogeny tree of the corresponding species is shown, highlighting five major orders within α-proteobacteria: Rhodospirillales, Sphingomonadales,Caulobacterales, Rhodobacterales, and Rhizobiales. FIG. 6*c*. Wide distribution of linker length across α-proteobacteria. Shown are the length distribution of the PopZ IDR across all of the 655 representatives α-proteobacteria and per order. Mean and s.e.m is reported for each.

FIG. 7*a-d* 6. PopTag condensates have tunable functionality. FIG. 7*a*. Scheme highlighting setup of the PopTag system and formation of GFP-PopTag condensates in U20S cells. FIG. 7*b*. Changing the linker length alters the FRAP dynamics and partitioning coefficient of PopTag condensates. Student's t-test; ** p-value <0.0001. FIG. 7***c*. Fusing PopTag to the drug-stabilized degron (DD) allows for the pharmacological control of PopTag expression. The addition of Shield-1 stabilizes the degron and prevents degradation of DD-PopTag condensates. FIG. 7*d*. NanoPop condensates can sequester different GFP-tagged client proteins upon transient expression.

DETAILED DESCRIPTION OF THE INVENTION

The inventors have discovered active fragments of the PopZ bacterial protein family that are capable of forming cellular compartments (membraneless organelles) and surprisingly can form them when expressed in eukaryotic cells. Moreover, it has been discovered that the active fragments can be fused with a heterologous polypeptide sequence to generate a number of beneficial functionalities.

Active fragments of the PopZ protein (the full-length of which is found in α-proteobacteria (e.g., *Caulobacter crescentus*)) have been discovered. For example, the following peptide (referred to as "PopTag") has been discovered to form membraneless organelles when expressed in prokaryotic or eukaryotic cells:

```
                                          (SEQ ID NO: 1)
EVAEQLVGVSAASAAASAFGSLSSALLMPKDGRTLEDVVRELLRPLLKEW

LDQNLPRIVETKVEEEVQRISRGRGA.
```

A large number of PopZ domains are known. For example a listing of PopTag protein domain from other bacterial species is provided at the end of this application (SEQ ID NOA4-149). Any of these sequences or substantially identical variants thereof can form a polypeptide corresponding to SEQ ID NO:1I and can be used as described for the PopTag polypeptide. By comparing a number of different PopZ proteins from various species, the following variants of SEQ ID NO:1 (also considered "PopTag" proteins) have been determined: ID-6T,

TABLE 1

| | | |
|---|---|---|
| 1 | E | Q; H; K; D; |
| 2 | V | A; E; D; G; F; L; M; L; N; Q; P; S; R; T; Y; |
| 3 | A | E; D; G; N; Q; P; S; R; T; V; |
| 4 | E | A; D; G; H; K; M; L; N; Q; P; S; R; T; |
| 5 | Q | A; E; D; G; F; H; K; M; L; N; P; S; R; T; V; |
| 6 | L | A; E; D; I; M; N; Q; P; R; V; |
| 7 | V | A; E; D; G; F; L; M; L; P; S; T; |
| 8 | G | A; E; D; I; —; L; N; S; T; V; |
| 9 | V | A; E; D; G; E; L; H; K; —; M; L; N; Q; P; S; R; T; |
| 10 | S | A; E; D; G; F; I; H; K; —; M; L; N; Q; P; R; T; V; |
| 11 | A | E; G; I; K; —; N; Q; P; S; R; T; V; |
| 12 | A | C; E; D; G; F; I; H; K; —; M; L; N; Q; P; S; R; T; V; |
| 13 | S | A; E; D; G; F; I; H; K; —; M; L; N; Q; R; T; V; |
| 14 | A | C; E; D; I; H; K; —; M; L; N; Q; S; R; T; V; X; |
| 15 | A | E; G; F; L; —; M; L; Q; S; T; V; X; |
| 16 | A | E; D; G; F; I; H; K; —; M; L; N; Q; S; R; T; V; Y; X; |
| 17 | S | A; E; D; G; H; K; —; L; N; Q; R; T; V; |
| 18 | A | G; I; H; K; —; M; L; N; Q; P; S; R; T; V; Y; |
| 19 | F | A; G; I; M; L; S; R; V; Y; |
| 20 | G | A; E; D; F; H; K; M; L; N; Q; P; S; R; T; V; |
| 21 | S | A; E; D; G; F; I; H; K; M; L; N; Q; R; T; V; Y; |
| 22 | L | A; F; V; |
| 23 | S | A; E; D; G; E; I; —; M; L; N; Q; P; R; T; H; V; Y; X; |
| 24 | S | A; E; D; G; F; H; K; —; L; N; Q; P; R; T; V; |
| 25 | A | M; E; D; G; F; I; H; K; —; L; N; Q; P; S; R; T; V; |
| 26 | L | A; E; G; F; I; —; K; M; N; Q; P; S; R; T; H; V; |
| 27 | L | A; E; D; G; F; I; —; K; M; Q; P; S; R; T; H; V; |
| 28 | M | A; E; D; G; F; I; H; K; —; L; N; Q; P; S; R; T; V; Y; |
| 29 | P | A; E; D; G; H; K; —; L; N; Q; S; R; T; V; |
| 30 | K | A; M; E; D; G; F; I; H; —; L; N; Q; P; S; R; T; V; Y; |
| 31 | D | A; M; E; G; I; H; K; —; L; N; Q; P; S; R; T; V; |
| 32 | G | A; M; E; D; L; H; K; —; L; N; Q; P; S; R; T; V; |
| 33 | R | A; C; E; D; G; I; —; K; M; L; N; Q; P; S; T; H; V; Y; |
| 34 | T | A; D; —; M; L; P; S; R; V; |
| 35 | L | A; F; I; M; S; V; |

TABLE 1-continued

| | | |
|---|---|---|
| 36 | E | A; D; G; H; N; Q; |
| 37 | D | A; E; G; —; K; M; N; Q; S; R; T; V; |
| 38 | V | A; F; I; H; K; M; L; T; Y; |
| 39 | V | A; G; I; M; L; S; T; |
| 40 | R | A; E; G; I; H; K; M; L; N; Q; S; T; V; |
| 41 | E | A; D; G; N; Q; S; T; V; |
| 42 | L | A; E; I; M; S; T; V; |
| 43 | L | I; A; C; M; V; |
| 44 | R | A; H; K; N; Q; T; |
| 45 | P | Q; S; E; G; V; |
| 46 | L | E; L; M; Q; V; Y; |
| 47 | E | I; M; V; |
| 48 | K | A; D; G; H; Q; S; R; T; |
| 49 | E | A; D; G; I; H; N; Q; S; T; V; |
| 50 | W | Y; |
| 51 | L | I; M; V; |
| 52 | D | H; S; V; E; N; |
| 53 | Q | A; E; D; G; I; H; K; M; L; N; S; R; T; |
| 54 | N | E; H; K; Q; R; Y; |
| 55 | L | M; V; |
| 56 | P | A; E; G; K; N; Q; S; T; |
| 57 | R | A; E; D; G; I; H; K; L; N; Q; P; S; T; V; Y; X; |
| 58 | I | M; L; T; V; |
| 59 | V | A; I; T; |
| 60 | E | A; D; H; K; Q; S; R; |
| 61 | T | A; E; D; G; H; K; L; N; Q; S; R; W; |
| 62 | K | A; C; E; F; I; H; M; L; Q; S; RT; V; Y; |
| 63 | V | I; |
| 64 | E | A; D; G; H; K; N; Q; S; R; T; V; |
| 65 | E | A; D; I; H; K; L; N; Q; S; R; T; V; |
| 66 | E | A; D; Q; |
| 67 | V | I; M; L; |
| 68 | Q | A; E; D; H; K; N; S; R; T; V; |
| 69 | R | C; G; K; M; N; T; Y; |
| 70 | 1 | A; M; L; T; V; |
| 71 | S | A; I; M; L; N; R; T; V; |
| 72 | R | A; E; G; H; K; —; N; Q; S; T; V; |
| 73 | G | A; C; D; H; K; —; M; L; N; Q; S; R; T; |
| 74 | R | A; E; G; H; K; N; Q; P; S; T; |
| 75 | G | A; S; D; N; |
| 76 | A | S; G; V; |
| 1 | E | Q; H; K; D; |
| 2 | V | A; E; D; G; F; I; M; L; N; Q; P; S; R; T; Y; |
| 3 | A | E; D; G; N; Q; P; S; R; T; V; |
| 4 | E | A; D; G; H; K; M; L; N; Q; P; S; R; T; |
| 5 | Q | A; E; D; G; F; H; K; M; L; N; P; S; R; T; V; |
| 6 | L | A; E; D; I; M; N; Q; P; R; V; |
| 7 | V | A; E; D; G; F; I; M; L; P; S; T; |
| 8 | G | A; E; D; I; —; L; N; S; T; V; |
| 9 | V | A; E; D; G; F; 1; H; K; —; M; L; N; Q; P; S; R; T; |
| 10 | S | A; E; D; G; F; I; H; K; —; M; L; N; Q; P; R; T; V; |
| 11 | A | E; G; I; K; —; N; Q; P; S; R; T; V; |
| 12 | A | C; E; D; G; F; I; H; K; —; M; L; N; Q; P; S; R; T; V; |
| 13 | S | A; E; D; G; F; I; H; K; —; M; L; N; Q; R; T; V; |
| 14 | A | C; E; D; I; H; K; —; M; L; N; Q; S; R; T; V; X; |
| 15 | A | E; G; F; I; —; M; L; Q; S; T; V; X; |
| 16 | A | E; D; G; F; I; H; K; —; M; L; N; Q; S; R; T; V; Y; X; |
| 17 | S | A; E; D; G; H; K; —L; N; Q; R; T; V; |
| 18 | A | G; I; H; K; —; M; L; N; Q; P; S; R; T; V; Y; |
| 19 | F | A; G; I; M; L; S; R; V; Y; |
| 20 | G | A; E; D; F; H; K; M; L; N; Q; P; S; R; T; V; |
| 21 | S | A; E; D; G; F; I; H; K; M; L; N; Q; R; T; V; Y; |
| 22 | L | A; F; V; |
| 23 | S | A; E; D; G; F; I; —; M; L; N; Q; P; R; T; H; V; Y; X; |
| 24 | S | A; E; D; G; F; H; K; —; L; N; Q; P; R; T; V; |
| 25 | A | M; E; D; G; F; I; H; K; —; L; N; Q; P; S; R; T; V; |
| 26 | L | A; E; G; F; I; —; K; M; N; Q; P; S; R; T; H; V; |
| 27 | L | A; E; D; G; F; I; —; K; M; Q; P; S; R; T; H; V; |
| 28 | M | A; E; D; G; F; I; H; K; —; L; N; Q; P; S; R; T; V; Y; |
| 29 | P | A; E; D; G; H; K—; L; N; Q; S; R; T; V; |
| 30 | K | A; M; E; D; G; F; I; H; —; L; N; Q; P; S; R; T; V; Y; |
| 31 | D | A; M; E; G; I; H; K; —; L; N; Q; P; S; R; T; V; |
| 32 | G | A; M; E; D; I; H; K; —; L; N; Q; P; S; R; T; V; |
| 33 | R | A; C; E; D; G; I; —; K; M; L; N; Q; P; S; T; H; V; Y; |
| 34 | T | A; D; —; M; L; P; S; R; V; |
| 35 | L | A; F; I; M; S; V; |
| 36 | E | A; D; G; H; N; Q; |
| 37 | D | A; E; G; —; K; M; N; Q; S ; R; T; V; |
| 38 | V | A; F; I; H; K; M; L; T; Y; |
| 39 | V | A; G; L; M; L; S; T; |

TABLE 1-continued

| | | |
|---|---|---|
| 40 | R | A; E; G; I; H; K; M; L; N; Q; S; T; V; |
| 41 | E | A; D; G; N; Q; S; T; V; |
| 42 | L | A; E; I; M; S; T; V; |
| 43 | L | I; A; C; M; V; |
| 44 | R | A; H; K; N; Q; T; |
| 45 | P | Q; S; E; G; V; |
| 46 | L | E; I; M; Q; V; Y; |
| 47 | L | I; M; V; |
| 48 | K | A; D; G; H; Q; S; R; T; |
| 49 | E | A; D; G; I; H; N; Q; S; T; V; |
| 50 | W | Y; |
| 51 | L | I; M; V; |
| 52 | D | H; S; V; E; N; |
| 53 | Q | A; E; D; G; I; H; K M; L; N; S; R; T; |
| 54 | N | E; H; K; Q; R; Y; |
| 55 | L | M; V; |
| 56 | P | A; E; G; K; N; Q; S; T; |
| 57 | R | A; E; D; G; I; H; K; L; N; Q; P; S; T; V; Y; X; |
| 58 | I | M; L; T; V; |
| 59 | V | A; I; T; |
| 60 | E | A; D; H; K; Q; S; R; |
| 61 | T | A; E; D; G; H; K; L; N; Q; S; R; W; |
| 62 | K | A; C; E; F; I; H; M; L; Q; S; R; T; V; Y; |
| 63 | V | I; |
| 64 | E | A; D; G; H; K; N; Q; S; R; T; V; |
| 65 | E | A; D; I; H; K; L; N; Q; S; R; T; V; |
| 66 | E | A; D; Q; |
| 67 | V | I; M; L; |
| 68 | Q | A; E; D; H; K; N; S; R; T; V; |
| 69 | R | C; G; K; M; N; T; Y; |
| 70 | I | A; M; L; T; V; |
| 71 | S | A; I; M; L; N; R; T; V; |
| 72 | R | A; E; G; H; K; —; N; Q; S; T; V; |
| 73 | G | A; C; D; H; K; —; M; L; N; Q; S; R; T; |
| 74 | R | A; E; G; H; K; N; Q; P; S; T; |
| 75 | G | A; S; D; N; |
| 76 | A | S; G; V; |

Using Sequence Homology to Generate a List of Amino-Acid Substitutions Shown in Table 1.

We started by aligning PopTag to its homologs within α-proteobacteria. We used BLASTP 2.10.0 with parameters: Max target sequences: 5000, Expected threshold: 10. Word size: 3, Max matches in a query range: 0, Matrix: BLOSUM62, Gap Costs: Existence:11 Extension:1, Compositional adjustments: Conditional compositional score matrix adjustment.

We detected 4199 candidate homologous sequences. For filtered out candidate sequence with homology to less than 50% of the PopTag sequence. For the remaining of the candidate homologous sequences, we extracted amino-acid substitutions based on the reported BLAST alignment.

Using binding energy to predict mutations that maintain PopZ self-assembly capabilities.

We ran Rosetta ab-initio protein folding to predict PopTag structure (Rosetta server). We ended up with five possible structures. From there, we ran ZDOCK 3.0.2 to predict PopTag-PopTag homo-dimer structure. We ended up with 50 possible models (10 possible homo-dimer models per each of the 5 modeled PopTag monomers). We then used MODELLER homology modeling to predict the structure of mutated PopTags, based on (1). We then superposed each homology model on the 50 docking complexes and ran FiberDock to refine the structure and calculate free binding energy. We included substitutions with calculated binding energy that supports PopTag-PopTag dimerization.

In some embodiments, the polypeptide has the following sequence, wherein amino acids in parentheses are alternatives at the designated position:

(SEQ ID NO: 2)
```
(E/D)VA(E/D)QLVGVSAASAAASAFGSLSSALLMPKDGRTLEDVVR

(E/D)LLRPLLKEWL(D/E)QNLPRIV(E/D)TKV(E/D)(E/D)(E/D)

VQRISRGRGA.
```

Polypeptides described herein can be substantially identical to SEQ ID NO:1 or SEQ ID NO:2. For example, in some embodiments, the polypeptide is at least 60%, 70%, 80%, 85%, 90%, 95%, 98%, or 99% identical to SEQ ID NO:1 or SEQ ID NO:2. In some embodiments, the polypeptide has 1, 2, 3, 4, 5, 6, or more amino acid changes (or amino acid insertions or deletions) compared to SEQ ID NO:1 as listed in Table 1 (i.e., has one of the possible mutations as listed in Table 1 at 1, 2, 3, 4, 5, 6, or more different amino acid positions).

In some embodiments, the polypeptide is a fragment of SEQ ID NO:1 or SEQ ID NO:2. For example, in some embodiments, the polypeptides comprise at least 60, 65, or 70 contiguous amino acids of SEQ ID NO:1 or SEQ ID NO:2 but do not include the full-length of SEQ ID NO:1 or SEQ ID NO:2. An exemplary fragment is (SEQ ID NO: 3)
```
AEQLVGVSAASAAASAFGSLSSALLMPKDGRTLEDVVRELLRPLLKEWL

DQNLPRIVETKVEEEVQRISRGRGA.
```

In some embodiments, the polypeptides comprise SEQ ID NO: 1 or SEQ ID NO:2 and comprise further amino acids from a native PopZ protein but does not include the full-length of the native PopZ polypeptide. In other embodiments, the polypeptide can include the full-length PopZ polypeptide.

The above-described PopTag polypeptides or fragments or variants thereof can be fused to a heterologous amino acid sequence. Any amino acid sequence can be added as desired, depending on the functionality desired to be localized to the membraneless organelle that will form from the polypeptide. In some embodiments, the heterologous amino acid sequence is a fluorescent or protein that degenerates a detectable signal, an enzyme, or an epitope-binding or target-binding protein.

The heterologous amino acid sequence can be fused to the amino terminus of the PopTag polypeptide. PopZ self-assembly generally occurs via interactions at the PopZ carboxyl terminus.

In some embodiments, the heterologous amino acid sequence comprises a detectable protein. In some embodiments, the detectable protein is fluorescent. Exemplary fluorescent proteins include but are not limited to blue fluorescent protein, green fluorescent protein, yellow fluorescent protein, and red fluorescent protein In some embodiments, the heterologous amino acid sequence comprises an enzyme. Enzymes can be used to convert one substance to another. By targeting the enzyme to the organelle formed by the PopTag protein, the reaction can be localized to the organelle, concentrating the product in a location and also allowing for ease in later purification of the product. Exemplary enzymes include, but are not limited to, SOD1 (UniProtKB-P00441), GAPDH (UniProtKB-P04406), TurboID (Branon, et al., Nature Biotechnology volume 36, pages880-887(2018)). In some embodiments, two or more PopTag fusions are used where two or more enzyme fusions are expressed to allow for localization of two or more enzymes (as parts of fusions) in the organelles.

This can be useful, for example, where the product of a first enzymatic reaction is the substrate of a second enzymatic reaction.

In some embodiments, the heterologous amino acid sequence comprises an epitope-binding protein. The term "epitope," as used herein, means a component of a molecule capable of specific binding to an antibody or antigen binding fragment thereof. Such components optionally comprise one or more contiguous amino acid residues and/or one or more non-contiguous amino acid residues. Epitopes frequently consist of surface-accessible amino acid residues and/or sugar side chains and can have specific three-dimensional structural characteristics, as well as specific charge characteristics. Conformational and non-conformational epitopes are distinguished in that the binding to the former but not the latter is lost in the presence of denaturing solvents. An epitope can comprise amino acid residues that are directly involved in the binding, and other amino acid residues, which are not directly involved in the binding. The epitope to which an antigen binding protein binds can be determined using known techniques for epitope determination such as, for example, testing for antigen-binding to antigen variants with different point mutations.

The epitope-binding protein can be selected to bind any specific target as desired. In some embodiments, the epitope-binding protein specifically binds to GFP-GFP nanobody (Kubala, et al., *Protein Sci.* 2010 December; 19(12): 2389-2401), HA-tag (Zhao, et al., *Nature Communications* volume 10, Article number: 2947 (2019)), SOD1 (WO2014/191493), or HTT (Butler, et al., *Prog Neurobiol.* 2012 May; 97(2): 190-204).

Eukaryote viruses require cellular uptake for host infection. Therapeutic and prophylactic anti-viral strategies can involve the generation of antibodies, nanobodies or other viral binding proteins that can prevent viral docking to the cell membrane and viral entry. Additionally, the antibody-mediated aggregation of viral particles is a another mode of anti-viral activity of these molecules. The PopTag and constructs comprising it can also be used in these strategies. In some embodiments, fusing virus-binding proteins, natural or designed, to the PopTag allows for the generation of anti-viral nanoparticles. Given their size and condensed state, in some embodiments, these nanoparticles can have improved characteristics, such as protein stability, retention in the body, increased binding affinity due to multivalency, increased vial aggregation or a combination thereof.

In some embodiments, the Pop-Tag-comprising nanoparticles are used to protect agricultural crops. For example, in some embodiments, the PopTag is fused to a pathogen-binding protein that binds to a plant pathogen (e.g., virus, fungus, bacteria). The nanoparticles can be applied for example by spraying them on target plants.

In some embodiments, the Pop-Tag-comprising nanoparticles are used to protect against animal pathogens, (e.g., human or non-human viruses). Depending on the entry mechanisms of the pathogen, the Pop-Tag-comprising nanoparticles can be administered via injection, external application or nasal sprays. Exemplary target viruses can include but are not limited to influenza and SARS-CoV-2.

Accordingly, in some embodiments, the amino acid comprises or is part of, an antibody. In some embodiments, the antibody is or comprises an antigen-binding fragment, preferably made of a single amino acid chain that retains epitope binding activity. Antigen binding fragments of an antibody molecule are well known in the art, and include, for example, (i) a Fab fragment, a monovalent fragment consisting of the VL, VH, CL and CHi domains; (ii) a F(ab')2 fragment, a bivalent fragment comprising two Fab fragments linked by a disulfide bridge at the hinge region; (iii) a Fd fragment consisting of the VH and CHi domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv) (see e.g., Bird et al. (1988) *Science* 242:423-426; Huston et al. (1988) *Proc. Natl. Acad. Sci.* USA 85:5879-5883); (viii) a single domain antibody. These antibody fragments are obtained using techniques known to those skilled in the art, and the fragments are screened for utility in the same manner as are intact antibodies.

Antibody molecules can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, rat, guinea, pig, human, camel, llama, fish, shark, goat, rabbit, and bovine. Single domain antibodies are described, for example, in International Application Publication No. WO 94/04678. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species (e.g., camel, llama, dromedary, alpaca and guanaco) or other species besides Camelidae.

In some embodiments, an epitope binding fragment can also be or can also comprise, e.g., a non-antibody, scaffold protein. These proteins are generally obtained through combinatorial chemistry-based adaptation of preexisting antigen-binding proteins. For example, the binding site of human transferrin for human transferrin receptor can be diversified using the system described herein to create a diverse library of transferrin variants, some of which have acquired affinity for different antigens. See, e.g., Ali et al. (1999) *J. Biol. Chem.* 274:24066-24073. The portion of human transferrin not involved with binding the receptor remains unchanged and serves as a scaffold, like framework regions of antibodies, to present the variant binding sites. The libraries are then screened, as an antibody library is screened, and in accordance with the methods described herein, against a target antigen of interest to identify those variants having optimal selectivity and affinity for the target antigen. See, e.g., Hey et al. (2005) TRENDS Biotechnol 23(10):514-522.

In some embodiments, the scaffold portion of the non-antibody scaffold protein can include, e.g., all or part of the Z domain of *S. aureus* protein A, human transferrin, human tenth fibronectin type III domain, kunitz domain of a human trypsin inhibitor, human CTLA-4, an ankyrin repeat protein, a human lipocalin (e.g., anticalins, such as those described in, e.g., International Application Publication No. WO2015/104406), human crystallin, human ubiquitin, or a trypsin inhibitor from E. elaterium.

In some embodiments, the heterologous amino acid sequence comprises a target-binding protein. For example, in some embodiments, the target-binding protein binds a target molecule that is localized in the cell, thereby allowing for localization of the membraneless organelle to a particular cellular location. As some examples, the target-binding protein is, e.g., a M17 peptide (which is inserted in the plasma membrane upon myristoylation), spectrin beta, non-erythrocytic 2 (SPTN2) (which binds actin), EBIl (which binds microtubules), Perilipin 1 (PLIN1) (which binds lipid droplets), or an MLLE domain (which binds axatin-2 and other proteins harboring PAM2 motifs). In other embodiments, the target is a cellular molecule ((e.g., a receptor protein binds its cognate ligand).

In some embodiments, the target binding protein is a protein that has binding affinity for a certain protein or non-protein molecule or a protein motif. Thus, for example, certain receptors have an affinity for certain ligands. Thus the target-binding protein can be a binding protein that allows for localization of a target protein to the organelle formed by the PopTag protein and/or localization of the organelle to the cellular location of the target protein to which the target binding protein binds.

In some embodiments, an epitope-binding protein or target-binding protein is a fusion partner with the PopTag protein allows for localization of the epitope-containing molecule to the organelle. This can be useful where the epitope-containing molecule (or target) is a desired product, which can be purified from the cell as described herein. Alternatively, the epitope-containing molecule or target can be an undesirable product that can thereby be sequestered in the organelles and thereby removed from the cytoplasm.

The PopTag protein and the fusion partner can be linked directly or via an amino acid linker. In embodiments in which a linker links the two fusion partners, the linker can be of any length as desired. In some embodiments, the linker is between 1-200, e.g., 1-100, 1-20, or 1-10 amino acids for example. In some embodiments, the linker comprises at least 20, 30, 40, 50, 60 70% or more acidic amino acid residues (e.g., D and E) optionally with a majority of the remaining amino acids in the linker being A, V, or P. In some embodiments, the linker is DDAPAEPAAEAAPPPP-PEPEPEPVSFDDEVLELTDPIAPEPELPPLETVG-DIDVYSPPEPESE PAYTPPPAAPVFDRDDDAPAEPAAEAAPPPP-PEPEPEPVSFDDEVLELTDPIAPEPELPPLE TVG-DIDVYSPPEPESEPAYTPPPAAPVFDRD (SEQ ID NO: 150). In some embodiments, the linker modulates the material properties of the PopTag condensate, and can be selected for desired properties.

The PopTag proteins and PopTag fusions as described herein can be expressed in any cell to generate PopTag membraneless organelles. As shown herein, expression of these proteins in eukaryotic and prokaryotic cells results in PopTag oligomerization and organelle formation, including as fusion proteins. Accordingly, in some embodiments, a cell comprising (e.g., expressing) the PopTag fusion polypeptides is provided. In some embodiments, the cells comprising the PopTag fusion polypeptides are prokaryotic cells. Exemplary prokaryotic cells include but are not limited to, *Escherichia coli, Caulobacter crescentus*. In some embodiments, the cells comprising the PopTag fusion polypeptides are eukaryotic cells. Exemplary eukaryotic cells include but are not limited to, mammalian (e.g., human), fungal (e.g., yeast) or plant cells.

The PopTag fusion polypeptides can be introduced into a cell in any way desired. In some embodiments, an expression cassette comprising a promoter operably linked to a polynucleotide encoding the PopTag fusion protein is introduced into the cell. The cell can then be exposed to conditions conducive for expression. The promoter can be for example, inducible or constitutive. The expression cassette can be introduced by a vector (e.g., a plasmid of viral vector) or can be delivered directly (e.g., via electroporation or biolistics). Exemplary vectors include but are not limited to, a recombinant adeno-associated virus, a recombinant adenoviral, a recombinant lentiviral, etc. For example, viral vectors can be based on vaccinia virus, poliovirus, adenovirus, adeno-associated virus, SV40, herpes simplex virus, human immunodeficiency virus, and the like. A retroviral vector can be based on Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, mammary tumor virus, and the like. Introduction of the expression cassette can be performed in vitro, ex vivo (e.g., removal of cells from the body, introduction of the expression cassette outside the body, and reintroduction of the cells into the body), or in vivo (e.g., via gene therapy).

Cells expressing the fusion polypeptides described herein as well as vectors and expression cassettes encoding the fusion polypeptides can in some embodiments be administered to an animal (e.g., a human) to cause a biological effect. In some embodiments the effect is a prophylactic or therapeutic effect. For example, the cells can have an affinity for a cytotoxic or other undesirable molecule or protein and can allow for sequestration of that molecule or protein in the cell.

As noted above, in some embodiments, two or more (e.g., 2, 3, 4, 5, or more) different fusion proteins, each comprising a PopTag protein can be introduced into the same cell. This will result in organelles comprising the multiple different fusions (interacting via the common PopTag fusion partner), allowing for multiple functionalities in the same organelle based on the functionalities of the various fusion partners.

In some embodiments, the PopTag fusion polypeptide further includes one or more drug-inducible degron degradation motifs, allowing for inducible degradation of the PopTag fusion proteins in an inducible manner. Exemplary inducible degradation systems include those described in Lambrus, B. G., Moyer, T. C., and Holland, A. J. Methods in Cell Biol 358(6364): 716-8. (2017)

One advantage of localization of the fusion proteins, and optionally molecules that bind to the fusion proteins or products that are catalyzed by the fusion proteins, is that the organelles formed by the fusion proteins can be readily purified from cells containing them. For example, in some embodiments, a cell expressing the fusion proteins and thereby containing membraneless organelles composed of the fusion proteins, can be lysed and the resulting lysate can be separate from the organelles. In some embodiments, the separation can be achieved by centrifugation of the lysate and subsequent removal of the organelles which will separate from most of the remaining lysate due to differential density. As noted above, by purifying the organelles one can readily purify any desired component of the organelle of contents of the organelle (e.g., a product made by one or more enzyme as part of the fusion protein).

Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "sequence identity" or "percent identity" in the context of two or more nucleic acids or polypeptides refer to two or more sequences or subsequences that are the same ("identical") or have a specified percentage of amino acid residues or nucleotides that are identical ("percent identity") when compared and aligned for maximum correspondence with a second molecule, as measured using a sequence comparison algorithm (e.g., by a BLAST alignment), or alternatively, by visual inspection.

The phrase "substantial identity" or "substantially identical," used in the context of two nucleic acids or polypeptides, refers to a sequence that has at least 60% sequence identity with a reference sequence. Alternatively, percent identity can be any integer from 70% to 100%. In some embodiments, a sequence is substantially identical to a reference sequence if the sequence has at least 60%, 65%, 70%, 75%, 80%, 85%, 90%, 91%, 92%, 93%, 94%, 95%, 96%, 97%, 98%, or 99% sequence identity to the reference sequence as determined using the methods described herein; preferably BLAST using standard parameters, as described below.

Embodiments of the present invention provide for nucleic acids encoding polypeptides that are substantially identical to any of SEQ ID NO:1 or SEQ ID NO:2.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, Proc. *Nat'l. Acad. Sci.* USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci.* USA 89:10915 (1989)).

The BLAST algorithm also performs a statistical analysis of the similarity between two sequences (see, e.g., Karlin & Altschul, *Proc. Nat'l. Acad. Sci.* USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

As with all peptides, polypeptides, and proteins, including fragments thereof, it is understood that additional modifications in the amino acid sequence of the PopTag proteins described herein can occur that do not alter the nature or function of the antibodies or antigen-binding fragments thereof. Such modifications include conservative amino acid substitutions, such that each recited sequence optionally contains one or more conservative amino acid substitutions. The list provided below identifies groups that contain amino acids that are conservative substitutions for one another; these groups are exemplary as other conservative substitutions are known to those of skill in the art.

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

By way of example, when an aspartic acid at a specific residue is mentioned, also contemplated is a conservative substitution at the residue, for example, glutamic acid. Non-conservative substitutions, for example, substituting a proline with glycine, are also contemplated.

An amino acid residue "corresponding to an amino acid residue [X] in [specified sequence," or an amino acid substitution "corresponding to an amino acid substitution [X] in [specified sequence]" refers to an amino acid in a polypeptide of interest that aligns with the equivalent amino acid of a specified sequence.

A polynucleotide sequence is "heterologous" to an organism or a second polynucleotide sequence if it originates from a foreign species, or, if from the same species, is modified from its original form.

An "expression cassette" refers to a nucleic acid construct that, when introduced into a host cell, results in transcription and/or translation of an RNA or polypeptide, respectively.

Unless defined otherwise, all technical and scientific terms used herein have the same meanings as commonly understood by one of ordinary skill in the art to which this technology belongs. Although exemplary methods, devices and materials are described herein, any methods and materials similar or equivalent to those expressly described herein can be used in the practice or testing of the present technology. For example, the reagents described herein are merely exemplary and that equivalents of such are known in the art. The practice of the present technology can employ, unless otherwise indicated, conventional techniques of tissue culture, immunology, molecular biology, microbiology, cell biology, and recombinant DNA, which are within the skill of the art. See, e.g., Sambrook and Russell eds. (2001) Molecular Cloning: A Laboratory Manual, 3rd edition; the series Ausubel et al. eds. (2007) Current Protocols in Molecular Biology: the series Methods in Enzymology (Academic Press, Inc., N.Y.); MacPherson et al. (1991) PCR I: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5th edition; Miller and Calos eds. (1987) Gene Transfer Vectors for Mammalian Cells (Cold Spring Harbor Laboratory); and Makrides ed. (2003) Gene Transfer and Expression in Mammalian Cells (Cold Spring Harbor Laboratory).

EXAMPLE

Example 1

1. PopTag is Sufficient for Phase Separation in Human Cells

We identified PopTag, a 76 amino-acid sequence extracted from the bacterial protein PopZ (UniProt ID Q9A8N4), that phase separates in U2OS osteosarcoma cell line. A heterologous protein of choice (ORF, open reading frame) can be visualized with GFP (green fluorescent protein), and fused to the PopTag with the possibility of a central linker. When expressing GFP alone, GFP is diffusely localized throughout the cell. Upon fusion of GFP to the PopTag, with a central (GGGGS)4 spacer (SEQ ID NO: 151), GFP-PopTag forms phase-separated condensates in the cytoplasm. Insertion of a negatively charged linker tunes the material properties of PopTag condensates from gel-like to liquid-like, as assayed by an increase in fluid-like dynamics (FRAP, fluorescent recovery after photobleaching) and decrease in molecular density (partitioning coefficient).

2: PopTag Condensates have Tunable Material Properties

Protein binding domains, so-called anchors, target PopTag condensates to different cellular localizations. While GFP-PopTag condensates localize to the bulk of the cytoplasm, fusion to M17 targets it to the plasma membrane, the actin binding domain of SPTN2 confers actin cytoskeleton localization, the microtubule binding domain of EBI1 to the microtubule cytoskeleton, and an amphipathic helix of the PLIN1 protein to the surface of lipid droplets.

GFP-PopTag condensates have gel-like properties, based on (1) their poor dynamics as assayed by fluorescence recovery after photobleaching, FRAP, and (2) high partitioning coefficient indicating high molecular density. By inserting a negatively charged spacer (DDAPAEPAAEAAPPPPPEPEPEPVSFDDEVLELTDPIAPEPELPPLETVGDIDVYSPPEPESEPAYTPPPAAPV FDRDDDAPAEPAAEAAPPPPPEPEPEPVSFDDEVLELTDPIAPEPELPPLETVGDIDVYSPPEPESEPAYTPPPA APVFDRD (SEQ ID NO: 150), derived from PopZ UniProt ID: Q9A8N4), between the (GGGGS)4 spacer (SEQ ID NO: 151) and the PopTag, we can tune the material properties to more fluid-like behavior, indicated by an increase in FRAP dynamics, larger condensate size due to droplet fusion events, and a decreased partitioning coefficient.

3: PopTag Condensates have Tunable Cellular Localization

Fusing anchors (i.e., protein domains that bind to specific cellular structural features) to PopTag condensates allows targeting to different cytoplasmic compartments and organelles. In our assay, we fused anchors at the N-terminus of our GFP-PopTag and show altered localization depending on the specific anchor): (1) The M17 peptide, an HIV-derived peptide that is targeted to the plasma membrane upon myristoylation by the cell, targets the GFP-PopTag condensates to the plasma membrane. (2) The actin binding domain of SPTN2 targets GFP-PopTag condensates to the actin cytoskeleton. (3) The microtubule binding domain of EBI1 targets GFP-PopTag condensates to the microtubule cytoskeleton. (4) An amphiphatic alpha helix derived from PLIN1 targets GFP-PopTag condensates to the surface of lipid droplets.

(FIG. 3B)

4: PopTag Condensates have Tunable Enzymatic Functionality

PopTag condensates can be functionalized by fusion to different enzymes. Fusion to the PopTag allows for the formation of enzyme condensates in the cytoplasm. For example, fusion of the PopTag to SOD1 and GAPDH results in their phase separation in the cytoplasm. Additionally, fusion of the PopTag to the biotinylating enzyme TurboID results in the formation of condensates that stain positive for streptavidin (SA) upon treatment of the cells with biotin-indicating that TurboID retains its enzymatic activity within the context of phase-separated PopTag condensates.

5: PopTag Droplets have Tunable Composition

PopTag droplets can be engineered to have different protein composition. By fusing specific protein binding domains to the PopTag, one can recruit a client protein to the condensates. The MLLE domain of PABPC1 can bind to the PAM2 motif of ATXN2, a protein that is implicated in the pathogenesis of spinocerebellar ataxia type 2 (SCA2) and amyotrophic lateral sclerosis (ALS). ATXN2 is not enriched in GFP-PopTag condensates in the cytoplasm. However, upon fusion of the MLLE domain at the N-terminus of GFP-PopTag we do observe the recruitment of ATXN2 to the GFP-PopTag condensate.

5: NanoPop Sequesters GFP Tagged Proteins

To generate a system that would allow for the recruitment of any protein of interest we decided to test the compatibility of the PopTag system with nanobodies. Nanobodies are single chain antibodies derived from camelids or cartilaginous fish, of which the antigen binding domain can be expressed as a linear protein sequence. NanoPop includes a PopTag fused to a GFP nanobody, a single-chain antibody specific to GFP. We found that GFP tagged proteins are specifically recruited into NanoPop, as shown for the stress granule protein YB1, a cytoplasmic enzyme Glyceraldehyde 3-phosphate dehydrogenase (GAPDH), as well as NcI.

NanoPop condensates allowed for the recruitment of client proteins to PopTag condensates based on nanobody binding. A heterologous protein of choice (ORF, open reading frame) can be visualized with GFP (green fluorescent protein). Fusion of RFP (red fluorescent protein) to GFP nb (nanobody raised against GFP) allows for recruiting RFP to the GFP-tagged protein. Subsequent fusion to the PopTag allows specific recruitment of GFP-tagged protein to PopTag condensates. Nanobody-RFP fusion colocalizes with GFP diffusely throughout the cell. Nanobody-RFP-PopTag fusion, NanoPop, induces the recruitment of GFP to the cytoplasmic PopTag condensates. The recruitment to NanoPop condensates is observed for different GFP-tagged proteins that were expressed by plasmid transfection. Recruitment of endogenous GFP-tagged nuclear transport receptor KPNA2 to cytoplasmic NanoPop condensates prevents its nuclear localization, and subsequently perturbs nuclear localization of its cargo NPM1.

6: Drug-Induced PopTag Assemblies

Drug-inducible expression of PopTag condensates via degrons: To enable temporal control on the assembly of the PopTag, we developed a drug-inducible degradation of the PopTag proteins by fusion to a destabilizing domain (see, e.g., Banazynski, et al., *Cell* 2006 Sep 8; 126(5): 995-1004). Upon fusion of the DD (Destabilizing Domain, degron to the PopTag, rapid degradation is inhibited by incubating transfected cells (red outlines) with the Shield-1 compound. In cells lacking the compound, PopTag molecules are rapidly degraded, releasing any sequestered protein. Only in the presence of Shield-1, DD-GFP-PopTag condensates were present.

Methods Plasmid generation

Constructs encoding PopTag and fusion proteins we synthesized by Genscript (Piscataway, USA) and subcloned into pcDNA3.1+N-eGFP under the control of a CMV promoter.

Human Cell Culture and Transfection

U20S (ATCC) cells were cultured in DMEM medium (Thermo-Fisher Scientific) containing 10% FBS (Invitrogen) at 37° C. and 5% $CO_2$ and handled according to standard procedures. Cells were seeded on glass coverslips and allowed to adhere for 24h. Cells were subsequently transfected with plasmids encoding PopTag fusion proteins via Lipofectamine 3000 (Thermo Scientific) according to manufacturer's instructions.

Alternative PopTag Sequences

We identified the attached sequences as alternative PopTag fragments based on sequence alignment (same as 1). We then used MMseqs2 to cluster the sequences based on homology (0.65 minimum sequence identity and 0.65 minimum alignment coverage). We ended up with 146 sequences as follows (SEQ ID NO. 4-149, respectively).

```
>MAK64050
EVSEGIMSEPAASAAMGSFHTLADQIRISEEEGRTLEGVVRALLRPMLKEWLDANLPSIV

DEKVQAEIDRVSRRR

>OZB16237
EPLTDANTAESAAGALGKLISKMDIGSDNTLEGLVRELLKPMVKEWLDANLARIVEEKV

EAEVQRIAR

>WP_116399749
ELSDVLLSPAASESVAHAFDTLDRTLKMQNDGTLEDMSRELLRPMLKAWLDENLPALV

ERLVKAEIERVVRG

>WP_150286982
ERIMSDNTKALVSQAFQTLSRHTAMPAMGRSLEDVVVELLRPMLRDWIDSHLPAIVEK

HVRAEIERVARG

>WP_084563928
TAEDRILSEAADAAIGASFNVLSRTVVAQNPHTIEDLVRDMLRPMLQSWLDENLPRIVER

QVRAEIERVSRG

>SFZ82387
DIAEELLEPATKAAVRSTFARLNGLSAVAPGITLEDLIRDMMRPMLKEWLDENLPAVVE

RMVEKEIERVSRG

>RYZ14919
ETLTSAPVAQHAAGALGKLMGSMLVSSTGTLDDVVRELLKPMLKEWLDANLPQLVEA

EVAKEIDRIRR

>RZO67422
AAVAEDAFKSLNQSIRISGQSEKTLEDLVTDLLRPLMKEWLDENLPQIVEDKVQDEVTRI

AR

>KAB2877277
LLSSAASHAVDHAFSQFTQTVFTQNGRTIEDVGRDMLRPMLKSWLDDNLPGLVERLVR

AEIERVSRGR
```

-continued

>WP_107990003
DRLMSDNTDTTVHSAFASLSNTVLAANSRTLDELVREMLRPMIKGWLDDNLPTMVER

MVRQEIERVTRGR

>PCJ59580
DSLLDKTAAAAATESFGELTKAVIKEDGPGIQLGSLTEKTLEDLLKELLRPMLKEWLDQ

NLPSITEKLVRKEIERTAR

>OGN41220
DALVGESAAAXXXSAFAGLAASFKKPEPAAASSTEMPFVSGNTVEAMVAEMLRPMLK

DWLDNNLPAIVEAAVQREVERIARS

>WP_150968254
EGASALLSAQAGDQVAAAFDDLTRAIRDGQMRSMEEMAREMMRPMLQEWLDDNLPRI

VERLVRDEIERIARG

>WP_110354116
QVSERLVSSHTVESVGQNFHLLAQTVLSQNARTLEDLVQDMLRPMLKGWLDENLPHM

VERLVRAEIERVARGR

>OYW35496
KDLLSPSVDAVVAAAFESLGDMVLPAHERTVEDLVKEILRPMLKEWLDAHLPDIVERLV

RAEIERVSR

>WP_152586336
DALLSGAADACVADAFGRLGAAVAGRSSPATMEDFVAELLRPLLREWLDENLPPLVER

LVRAEIERISRG

>MBG50924
EPLISGATEAATAAAFGSLASSILTSSGDARTLEDLVADMLRPMLKDWMDKNLPSLVEQ

LVREEIERVARRGR

>MBF34074
EALTDERIAGAAATALGKLMVKRSSSEEEANPNTLDGLMREILRPMIKEWLDANLPAIV

ERKVEEEVQRIAR

>MSO89259
GEGLMSQSATMSSAGAIAHLNQALLGDYSDLLGNMGRMTVEDLVRELLRPLLKEWLD

RNLPPLVEQMVRNEIQRIVR

>RME62048
IVSDDVAVAASAKFDQLSHMLVRRYPGAENTLEGLVRDLLRPLLKEWLDANLPPLVEE

MVAREIERITRGKS

>WP_109253360
LLGESQAGVASAAFAALSENLRVSSGNGQTLEGIVRELMKPMLKQWLDENLPTIVEQK

VEEEIERVARRR

>OQW62276
TADAILSTPVASAAAGSLARLAGTLRISDQPGQTVEGVVRELLKPMLKEWLDRNLAAIV

EARVEAELERIAR

>WP_068000963
DLTETLISSATDQVVSSAFNGLANTVLSKNARTLEDMVAEMLRPMLKGWLDQHLPSVV

ERLVRQEIDRIS

>HAJ47106
LVSSHTQSAVNQAFSMLSRSNTNDMPIAQGDGRTLEDIVAQMLRPMLKDWLEDNLPA

MVERIVREEVERASRTTG

>WP_104831404
EIEDEILDQTTAAAASKAFTTLSQSVRVSEGPGRTLEDIVTEMLRPMVKEWLDANLPAIV

EEKVEEEVQRVARRR

-continued

>WP_062630189
DIAEGLLETTTKAAVRSSIGKLGAAGLGTIASPALGNGGLTIEAMVRELLRPMLKEWLDE

NLPAVVERMVEKEIARVARG

>WP_127070964
DMANELLEPATKAAVHSAFAKLGTPSKQTSDMALGASGLTIENMIREMLRPMLKDWLE

ENLPSMVERMVEKEIERVSRG

>WP_018996642
EGLVAAATADATAGQLGKLMGSMMLSQGTTIEDLVREMLKPMLKEWLDGNLPQLVEQ

EVKKELQRISR

>HAA93780
DNLIGDSPRAQATTSLANLSTAIREHRPGLTVEQLAEELLRPMLREWLDANLPDMVERL

VQKEIQRMA

>OYY45783
EALVGAGVAGATSSAFARLNQAVQDSVPAPAATDPGPRVGGSGQSIEDLVKEMLRPML

KEWLDTNLPPMVERYVEREIARLTR

>WP_136161146
EDIVSAAVASASRNALASLARLKVRAEDDAPENSLEGLVRDMLRPMLKEWLDANLPRI

VEAMVAKEIARISGDR

>WP_144343391
ERLVSGSASNAVSAAFGSLQRTVTSNSRTVDDLVTEAIRPMLKAWLDENLPTLVERLVR

AEIERVAR

>PHR54293
DELLSAASTAASAGTLGALASSMKLAETDGQTIEGVMRELLRPLLKDWLDTNLPAIVEA

KVEAAIDKVVR

>WP_024749786
LVSADAANSVASHFQALAASIVLSESDLIERYARDLLRPLLKQWLDDNLPHIVERLVRVE

IERVARGR

>WP_083579096
IVSDATASATAERLKALSSAMAGPESGSVTLEGLVREMLRPMLKDWLDRNLPDIVDEV

VSREIARLTGKG

>WP_099512227
QTAEALLSSEAVASVTGAFSRLSESVRPAQPQTVEDLMKEMLRPMLKAWLDDNLPPLV

ERLVREEIERVVRRRA

>WP_119422031
LVSAPVAQQAASTFSNLASTVSQVRGLPIGSPNRTLEDIVKELLRPMLKDWLDANLPTL

VHRIVEREVAKLAGR

>GEQ98249
EALVSSSTEERSSASFAELSAMLVGGYEGAGNTLEGLVREMLKPMLRAWLDENLPRIVE

DMVEREVARIAARG

>WP_127690594
AETMLSVESEVATRHSLSALSAMVVKPQEGGRDNTLESLVRELLRPMMKDWLDAHLP

DLVEAMVAKEIARITGRA

>WP_046863310
LLSPAVDSTVSQAFGLLSSTISNQSFSSTLLSSNPRTLEDLVGDLLRPLLKAWLDEHLPPL

VERLVRSEIERVARG

>WP_014077464
STQAARESLVNLSRLLIRPEDGPAGTLEDLVREMLRPMLKDWLDAHLPGLVETLVKREI

DRIT

-continued

>MPY74861
ADSIISTSTAAAGISSFGQLARSVKSGRPGITVEQLAEELMRPMLRQWLDENLPDMVERL

VRREIERMARA

>WP_110030672
QLISMDAGAKVAASFDHLSATLAASSTRSFDEIAEELLKPMLQNWLDDNLPTLVERLVR

EEIERVSRG

>MAS86895
EDDENLLSENTASASLAALDKLSRSSAIDNRRNINDAVTIEDITREMLRPMLKAWLDKNL

PDIIERTVQKEIRRLS

>WP_131117822
ETLVSPEAGATVGSAFQTLATSVVLQNSDTIEKLTREMLRPLLKSWLDDHLPALVERLV

RQEIERLARG

>PCJ89384
DHLLSNQAAESISGAFSNLSNLVVSGQAKTMEDLMREMLRPMLQAWLDQNLPPMVEK

MVASEIRRLSGR

>HAD25315
IVDKVTAQATAAALNQLVVDMPSYVGMGQGLSLEEIVKELLRPLLKEWLDQHLPGMA

ERLVQEEISRISRAR

>WP_046171594
DMADQLLEPATQAAVRSSITRLNGLGNTGATIESLMRDMLRPMLKEWLDENLPSVVER

MVEKEIARVSRG

>WP_111198331
AEQPAILSGNSAQAVQSAFGKLADSVLSRATNERSVEEVTRELLRVMLKQWLDENLPA

MVERMVREEIERVAR

>WP_040617591
LISNDTGAAVHTALDHLSAMFVGSKAQTVEELIQEMLRPMLKAWLDQHLPGMVEEMV

QKEIKRITRGR

>OJX54643
DMAEQLLAPATDAAVQGAMSRLGSLAGTGIGSMTVEAMIRDMLRPMLKDWLDENLPA

LVERMVEKEISRISRG

>MPT47087
QLQDNIVSAQSENAARSSLAALSNMMVKSAGQGDPATLEDLVKDMLRPMLKEWLDAN

LPNMVEGMVAKEISRITGR

>WP_073011368
EDDDPLTSDQTGEAVNAAFSNLASLYVGNAQTVEDLIKDMLRPMLKAWLDQNLPVLV

EQLVQKEIERVTRRR

>WP_099475008
EVLMSANSSGLAMDQFGILSDLLTSGYQGSGNTLEDLVREMLKPMLRGWLDENLPPLV

ERMVAKEIARLSRTK

>WP_134763919
KFAHALISREAGERVAASFSELAAAIRDDHLRDSDAIVREVMRPMLQEWLDENLPRLVE

QLVREEIERIARG

>MBG05802
IVSDPTAQAGVDAFGQLAGIIAGRMQLGQGRTVEELVQELLRPLLREWLDKNLPELVDE

LVKKEIERM

>TDI66500
EIEEGLLSADAAVATSAAFGDLNRTLTVSLGEGKTVEAIVGDLLRPLLKSWLDQHLPPLV

EQMVQEEIERLARRR

-continued

>WP_113943108
LISQAAEKQVAASFGSLSQALLEEQKRLLNDKMEAMLRPMLQEWLDTNLPPLVERLVR

EEIERVVRRG

>WP_099057644
AEALSGLNALVSAATVEQVSRSFGELAAAIDGQQRRSLDEMAEDMLRPMLREWLDDNL

PTLVERLVREEIERVARG

>WP_090699777
QPLLSAETNASVATAFQSLAQSVLLRDPGVMENMARDLLRPMLKQWLDDNLPPLVERL

VRAEIERAARG

>EKE77616
EEDEGLVSPPKRDEAVSAFANLTSTLEARHPELPIGAGHKTLESLTKEVMRPMLKDWLD

KNLPHIVERLVREEIERIAR

>WP_155191382
EFLTSAATGQAVHAALDNFSDMLISTKAQTIEEMVREMLRPMIKAWLDKNLPPMVEEM

VKKEIQRVIRRR

>MSP82741
DRLVSDFAANMASSRFSALARAAEPDPLEGVQRTGRTVEEIAVDLLRPMLKEWLDTNV

PSIVERMVEREIRYLSR

>CBS86857
EVDDGLISRRTAEDASHHLTHLARELGDDLSIGPMPIGIRTVEEVVRELLKPLLKEWLDE

NLPTVVERLVQQEIDRMIR

>WP_108659666
EMDDSLTSQKTRQSVTNSLDQLSRTILSNNPRTLEDLVRDMVRPLLREWLEANLPDIVE

RQVRQEIDRVASRGR

>TNE42206
LMSDSAAGAAAASFENLARAMPVLEEDSRSLEGIVVEMLRPVLAAWLDQHLPKIVEQM

VQKEIERVSR

>SDC97157
IAEPAASAHAGPSLSSLIINPAGTGQTLEGLVRDMLRPMLSDWIDTNLPGIVERLVKQEM

SGIN

>WP_152428646
EPIASPATDAAVASSFNALFASRLLPNPEMLAELTRDLLRPMLKAWLDDNLPVMVERLV

RAEIERVARG

>WP_109901738
EPLVSTPIANQARNAFAQVADAARPSVSPRESVGDGRTVEQVAEDLMRPMLKAWLDA

HLPAIVERAVAEELARITGRGS

>PPR25242
EVVEDDVLVSAATTAVGASAFAQLTGAMDLAMRLGGVDRTLEALVKELMRPMLRDW

LEANLPAVVERLVQREIDKMSVKSG

>WP_010919196
EVAEQLVGVSAASAAASAFGSLSSALLMPKDGRTLEDVVRELLRPLLKEWLDQNLPRIV

ETKVEEEVQRISRGRGA

>OYW82231
ASRLVSDRTESTAANAFGALTNALLVPKDGRTLEDVLKELMRPMLQDWLDKNLAAIVE

EQVRLEVERIAR

>TAJ69484
AANLVSDHIAAAAAATFGQLSSSILMPAEGRTLEDVVREMLRPMLQQWLDTNLPGIVQE

AVQAEVERIARGR

-continued

>WP_045319374
ASAFAGLTAAARTPADARSLEDIVRELLRPMLKDWIDANLPGIVEREVRAEVERISRQG

GA

>WP_126424045
ETTSHLVSERTVQSAVSAFGQLTSASLLPREGRSIEDLLTEILRPMLQDWLDGNLPAIVET

AVREEVERLAR

>HBJ92934
SAGKAAGALGQLMGSMAIGNGATLESIVRELLRPMLKEWLNENLPGIVEAKVEEEVKRI

SR

>WP_117396792
DIADSLLEPTAQAASSHAFSQLDNLIMSQKQGQTIEDLIREMLRPMLKSWLDENLPGVVE

QLVQREIERVSRGK

>WP_036837750
EMDEPLVSAAASATVQSAFGQLSHTVLAANGRTLDDLVKEMLRPMLHAWLDENLPVIV

ERLVRAEIERVSRGR

>WP_111433003
EPLLSPTSDAAVSAAFGNLAHTILSNNARTLEDLVGEMLRPMLKTWLDDNLPALVERLV

RQEIERVSRGR

WP_150942726
AETLLSSAANASVSDAFTRLGSTIMPTQPQTLEDLMKDLLRPILKSWLDENLPSLVERLV

QAEIERISRGQ

>WP_054731639
EELVSAASADAARQSLEALSAAVTPDTAATNAHVAPVPAARTMEDVVLDALRPMLKD

WLDTNLPSLVEAMVAKEISRITGKR

>WP_123152580
IVSTVAVEASRHALASLSKMVVKPEVAGSDTLEGVVRDMLKPMLKDWLDTHLPDIVER

MVAQEVARISGRS

>WP_082922353
SESLIAGAAAATLRDSFAALQSVASTPEPSKPAGTANPLEDMVREMMRPMLKQWLDDN

MPGMVEKIVEREIARITGR

>WP_113227590
NLVSAEAGAQIARSFGALAEVFDGVRNPTIETVAQDMLRPMLQEWLEDNLPTIVERMV

REEIERVARG

>OJW52521
SEPLVSSAAVSEAALSFQALNKVASESPRYPDPRLNAGIGGQTVENLVREILRPLLKEWL

DANLPTLVRWVVNEQVERIVR

>WP_116391335
AQTLVSDGAAKKVSDAFGALHENVRVSNAGGQTIEDIVEAMLRPMIQQWLDQNLPRIV

EEKVEEEVRRIARRR

>MSQ87355
LVGDPAVQAAGASIAQLANAVSRERAVVLGNTGITLEQLVREICTPILKEWLDTNLPHIV

DRVVKQEIERI

>TDN86484
ETIVSRQAADASRGKLESLSRMVVKPETPGSDTLEGMVREMLRPMLREWMDANLPGLV

ERMVQREIERIT

>WP_153478534
EGLLSDRAGASVGHAFDALSRTVSAQTPRSVEELVADILRPMLKSWLDQNLPGLVEDLV

RQEIERIARSR

-continued

>MBS27392
VSDEVEEVSAASMSGLTAALAATAAVGDGNKTLEELVKEVLRPILKEWLDDNLPDVVD

RIVHEEVERISQ

>MAZ76946
ILSDSAQSATMSSLSKLVGNVPLNRRGYDGITLEDIVRELLNPMIRDWMDDNLPPMVER

IVQKELEKLAR

>PPR71936
VTSEIVSASTAHAATDILSELAKAILNRRDVAVDDAGQNMTLEGMVREILKPLLREWLD

RNLPYLIERLVKKEIDTMINRAEG

>WP_094408892
DALMSPDTASAASRAFAKLQDMDEDESPAAAVMRASGGGNPTLDELVREALKPVLRE

WLDRNLPPMVETMVREEIQRLA

>PCJ02983
ISDSLISEQVGDAVNKNFHLLANTLLAQNGAGQTVESMVMALMRPMLKSWLDENLPV

MVEKIVREEIERVARG

>WP_056631067
EEAPAVSPATVEATRGALGALSRLIVKPEPESDGTLEGLVREMLRPMLSEWLDHNLPPL

VEQMVAREIAKIIANQG

>SIS42034
DRLVSPPTEVASAAIFSELYGALARDRGLGIGKVGITLEEIVREALRPLLREWLDANLPEL

VERLVRKEIERLVTG

>MBI05737
EPLMEVSSEDVAVSAFAALASQVSSGSAEHRAQAISPSERTLEDHVLEMLRPMLREWLD

KHLPEMVQRLVQREIDRITH

>WP_115936803
VSQATDALGTASFAYLEKSIRMGQVGDTLEDIVKGLLRPMLQSWLDENLPQLVERLVQ

REIEMMAGG

>WP_014102704
ESVLGEVAASATFAGFARLANNIAVDRRRQTGEGVTIEDIVRDMLQPLLRQWLDDNLPT

MIERMVQKELEKLAQ

>WP_121048327
EEAQSAVSDDIMAKASESFSALSSLRLRGDGAGPETLEGLVREMLQPMLKSWLDANLPE

IVEQMVAREIARITR

>MAZ00165
VREELISATTASASLEAMSKLVAEEVARPDSSSTIEQITKDLLRPMLKDWLDANLPALIEK

LVQKELRRLS

>WP_129792709
VTEEAGLLSSGAAAASRERLAALSALRQRTEIPTDTGALEAVVRDMLRPMLKDWLDEH

LPAIVEQLVTREIARIT

>MBK18883
LLDDEPATATTSSLSNLVAAVDADNSGTPLGDGNRTIEDLVKEVMRPMIKEWLDDNLP

ALVDRVVRREIERLSR

>WP_119775134
AERLVSETIASQARNAFAQVAQASRPPAGTRRADGDARSVEEVVEDLLRPMLKDWLDT

HLAGIVERCVAEELARIS

>WP_151591514
VAPHILSQVAERQVAAAFQDLSHVVRAEPRRSFDDIAAEIILRPMLQDWLDNNLPTLVER

LVREEIERVVRG

-continued

>PJI44352
EGLVSPPTAARAAAHLGQLSGAIAGSRAMGLGNSQRTLEELVKELLRPMLKEWLDAHL

ATIVQRIVEREVARLT

>WP_121154820
LVSDATLNASRSSIAALSALVIKPEITGGDTLEGLVREMLKPMLADWLDQRLPDVVERL

VAQEISRITARG

>WP_114911944
LANDTAESAAASIVGLVRTLAADRLTPVHRGGPTTEDLVREEIRPLLKTWLDAHLPALVE

RLVQNEIERV

>PIR33635
EHISDKTAATAKSSIESLVSQLANDTDTDPGAPFRSGETVEDLVKEMLKPMLKTWLDANL

PELVEAIVQKEIKKI

>MAQ70769
ATTATSDAFHKLAENVAISRQVGKVTLEDITRDLLRPMLRQWIHENMPQIVERLVQKEL

EKIAK

>WP_119268692
LMSEASSDATQAAFGRLAETLTRRALGERPIADVTQELLKGMLKQWLDENLPKIVERLV

REEIERVVR

>WP_011389550
VDERLISATTEVAAGGLLAELASAVARERTIGLGHGGVTLEDMVREILRQLLKDWLDEN

LPYMTERLVQKEIERL

>PCI01942
ILNDAAATATVSSMARLAENIAVSRTTEGTTLEDITRDLLRPMLKIWLDENLPTVIERLV

AQELERLAE

>MBL41367
DVASLLDSVTADNASAAFAQLANTRAERATTLEELVKELLRPMLKTWLDENLSQVVER

LVEKEITKLS

>WP_127612254
IAGATAAAMRDQLSALSNFSAAAPKTETTPHPLEDAVRDMLRPLLKEWLDANLEGIVER

IVQDEISRITGSR

>WP_068498366
AEPLISDPVARHSTSLLSDLAREIVRHRGIGLGNGGITLEDMVRELLKPILKEWLDDNLPY

MIERLVKQEIEKM

>WP_143130987
DSLLSPRAADSSATALAELSAAVARGRALGLGAGHTTLEEIVKELLRPILKEWLDNHLPG

MVERMVRQEMERL

PJB72509
EDGDSIFTDSAENAALQGFMKLASKMPLDRRGTGETTIEDIIREMMKPMLREWLDIHLPP

LIEKVVQKELRNIAR

>WP_025898636
EEPVVQAATSSFASLAGAVSASRGMPMGNSAATLEELVRDLLRPMLKEWLDEHLASIV

QRIVEREVSKLA

>SFF08372
SASSSRYGDVPPPLVSPTTGQLVGASFNELAEAIRQGELRSLEAMAQEMLQPMLRDWLD

DNLPKMVERLIREEIERLARG

>WP_093311076
LVSEQAASASRLSLAALSALIVSPAAEPARDNTLEGLVREMLRPMLKEWLDARLPEMVE

GLVAREIARIT

>BAT28987

-continued

AEPLISETSEAAIGASFAELTQAIRAGELRSLEEMAQDLLRPMMREWLEENLARMVEDIV

REEIRRAVTRGR

>PZU09872
VPEPAMLLSKQTQAASQRALAALSGLSIDPNADANTMDGLVREMLRPMLKDWLDAHL

PEMVERLVAREVARISGR

>MAH04765
GVTAEATLGAFERLAQSIPVNRPGTHGHTLEDIVRDMLRPMLRQWVDENMPTIAERLV

KKELERL

>WP_136694877
ELAEGLTNTVAADSMRQSLAALAMLSEPSAKPQIVRSGETSLEDMVRDLLRPLMAQWL

DAHLPEIVERLVKEEITRIA

>WP_083548962
ATELMSQTTRLAAGAAFEELSRSLQARDGAEPSRGTNPLEDLVKEAMRPMLREWLDAN

LNGIVERLVREEIQKVT

>MQA65746
DPLVSGSVAAASTAALGRLAQTVNRDPGSVGNFSLGAGTTLEDMVRDMVRPMLKEWL

DANLGPLVERMVKREIERMVR

>KAB2836666
EEIISSAAAHEFANAFSNLENTLKAPLSSAPQLPTFDKNNVGQMTLEMIVNQMLQPLLKE

WLDKHLPSLVKLLVSEQIEKI

>WP_007066121
LISDNAETKVSASFSELAAVLRDEQAQRMDATVREMLQPMLSDWLEDNLPIIVERLVRE

EIERVARG

>MSP19964
MAEGLVSRDTEAAATRSFAGLGATVSAVTGMPLGHPQRTIEELVRELLRPMLKQWLDR

NLQAIVALAVEREISCLSGRA

>WP_062139950
EKLLSEDALQESASAFAELARATQKPAVQDKPFKIESAGEYTVDNLMRELLRPLLREWL

DAHLPSIIRTLVAEQIEKTLQQR

>OYV24965
ESPDGLVGDEISTAVVSSIGSLVNSINNERSVTISRAGVTIEDVIREEIKPLLKAWLNTHLP

VLVERVVRAEIARV

>WP_022691990
EGLLSSTSAEASRSAFAALTQLQVRNDEGKSNTLEGLVSDLLRPMLKEYLDRELPGIVER

LVAVEVKRLA

>PHS77477
LSGADTQLEAGNAFASLTSTVQKQAVTEENGPPIGELVKEALKPMLQEWLDKNLKTMV

QRAVTKEIKRISTGK

>WP_130153757
EFQEGLLSPQAQAATIQSFAKLAEAAHHVQSAPKSEPTSPTLDQLIGELARPMVKQWLD

QHLPRLVELTVAKEIERLTK

>PKU24871
EVAEESLLSPPVQAASTTALAELARAVAQERGVGLGNGGVTLEEIVREILKSLIKDWLDQ

NLPYMIERIVKKEIEKM

-continued

```
>GDX38801
ETSEDLMSAQTASIVSDHFEALAARALVDNSDMVMALTQQLMKPMLKQWLDDHLPEI

VERLVQVEIKRISRQGRD

>GEL63958
ESLLGTSAKAAMDRSLESLNTALEQQAAPRHTLTATTRISNGTSSSIEDIVREEVREMVR

SWLDTNLPSMVENMVRAEITRMTR

>PZO84687
EDILTEAAKTAALSSMAKLAGNMPITRHREYGNITLEDLVREMLHPMLRDWVSENLPS

MVERLVQKELEKLAR

>WP_068070837
DAAAEEAGLLPEAAAASMRDSLTALAMLAEPGASPQIVRSGETSLEGLARELMRPMLA

EWLENNLPAMVEKMVAAEIARIAGKKG

>MAF67980
DVSEDNSEHISDRAAEEAVGALSKLAQNVALSNRSADVTLEDIVKELVRPMLRQWINEN

MSDIVEALVEKELEKLVR

>MBH63242
SEGLVSREAAEQTAAAFVDFASAVSSAQGVQLGASHRTLEELVKESLRPMLKVWLDNN

LQPIVSRTVEREIAKLAGRA

>WP_150061170
LVEASVAAVSSQYLSTLTDSLQGRDIPIGNGAITLEGLVRQIVRELVKQWLDENLPEMTE

RLVEREIQRLAKS

>WP_145609868
DRLMSQFTEEAASRAFSSLSGFRRGGPSLTGEGPIGRSDVTLEEIVHVLVRPILREWLDEN

LPSLVERLVKREIEKVVR

>TVQ33838
LTEVLLDSGTSSIASSALQRLSAAIAPGDAVAGGQRSIEVFLADLVRPELKAWLDTNLPP

LVERIVEREIKKLVR

>WP_138325922
EELIAARTRAATEQSFDALHAALKREEAANAPPAAPSPMLLRGGGPSLEDMVRQELRGL

LSAWLDEHLPGLVEALVRSQIEKMVRRGS
```

Example 2

Introduction

Biomolecular condensation is a powerful mechanism underlying cellular organization and regulation in cell physiology and disease [Boeynaems, S. et al., *Trends Cell Biol* 28, 420-435 (2018); *Shin, Y. & Brangwynne, C. P., Science* 357 (2017); Mathieu, *C., Pappu, R. V. & Taylor, J. P., Science* 370, 56-60 (2020)]. Many of these condensates are formed via reversible phase separation [Shin, Y. & Brangwynne, C. P., *Science* 357 (2017); Banani, S. F. et al., *Nat Rev Mol Cell Biol* 18, 285-298 (2017)], which allows for rapid sensing and responding to a range of cellular challenges [Yoo, H., Triandafillou, C. & Drummond, D. A., *J Biol Chem* 294, 7151-7159 (2019); *Franzmann, T. M. & Alberti, S., Cold Spring Harb Perspect Biol* 11 (2019)]. Biomolecular condensates can adopt a broad spectrum of material properties, from highly dynamic liquid to semi-fluid gels and solid amyloid aggregates [Banani, S. F. et al., *Nat Rev Mol Cell Biol* 18, 285-298 (2017); Kato, M. et al., *Cell* 149, 753-767 (2012); Boeynaems, S. & Gitler, A. D., *Dev Cell* 45, 279-281 (2018); Patel, A. et al., *Cell* 162, 1066-1077 (2015)]. Perturbing protein condensation can alter fitness[9-1] and mutations leading to high degrees of protein aggregation and other pathological phase transitions were implicated in various degenerative diseases [Patel, A. et al., *Cell* 162, 1066-1077 (2015); Boeynaems, S. et al., *Mol Cell* 65, 1044-1055 (2017); Molliex, A. et al., *Cell* 163, 123-133 (2015); Ramaswami, M., Taylor, J. P. & Parker, R., *Cell* 154, 727-736 (2013); Scheckel, C. & Aguzzi, A., *Nat Rev Genet* 19, 405-418 (2018)]. However, mechanistic link between the material properties of a biomolecular condensate and cellular fitness remains largely unexplored. Here, we show that the emergent properties of condensates formed by the bacterial protein PopZ confer biological function. Moreover, based on our insights into its underlying molecular grammar, we have engineered synthetic PopZ-based condensates in human cells with tunable cellular addresses and composition.

The bacterium *Caulobacter crescentus* reproduces by asymmetric division [Lasker, K., Mann, T. H. & Shapiro, L., *Curr Opin Microbiol* 33, 131-139 (2016)], and a key player orchestrating this event is the intrinsically disordered Polar Organizing Protein Z, PopZ [Bowman, G. R. et al., *Cell* 134, 945-955 (2008); Ebersbach, G. et al., *Cell* 134, 956-968 (2008)]. PopZ self-assembles into 200 nm microdomains that are localized to the cell poles (FIG. 1*a*). Visualizing the microdomain via cryo-electron tomography shows a homogeneous membraneless compartment that excludes large protein complexes, such as ribosomes [Bowman, G. R. et al., *Molecular microbiology* 76, 173-189 (2010); Dahlberg, P. D. et al., *Proc Natl Acad Sci USA* 117, 13937-13944 (2020)](FIG. 1*b*). In previous work, we found that retention in the microdomain is selective for cytosolic proteins that directly or indirectly bind to PopZ, allowing for the spatial regulation of kinase-signaling cascades that drive asymmetric cell division [Lasker, K. et al., *Nat Microbiol* 5, 418-429 (2020)]. PopZ mutants unable to condense into a polar microdomain result in severe cell division defects [Bowman, G. R. et al., *Mol Microbiol* 90, 776-795 (2013)]. Because of these properties, we sought to define material property-function relationships for the PopZ microdomain in vivo.

PopZ Phase Separates in *Caulobacter crescentus* and Human Cells.

To probe the dynamic behavior of PopZ, we expressed PopZ in a strain of *Caulobacter* bearing an mre$B^{A325P}$ mutant [Dye, N. A. et al., *Molecular microbiology* 81, 368-394 (2011)] that leads to irregular cellular elongation with a thin polar regions and wide cell bodies [Harris, L. K., Dye, N. A. & Theriot, J. A., *Mol Microbiol* (2014)]. In this background, the PopZ microdomain deforms and extends into the cell body before undergoing spontaneous fission, producing spherical droplets that moved throughout the cell (FIG. 1*c-d*). The deformation of the microdomain at the thinning cell pole, as well as the minimization of surface tension when unrestrained by the plasma membrane, provides in vivo evidence that the PopZ microdomain behaves as a liquid-like condensate. This observation is in line with the partial fluorescence recovery of PopZ upon photobleaching (FRAP), indicating slow internal dynamic rearrangements [Lasker, K. et al., *Nat Microbiol* 5, 418-429 (2020)] (FIG. 1*e*).

PopZ homologs are restricted to α-proteobacteria, and the sequence composition of the PopZ intrinsically disordered region (IDR) is divergent from the human disordered proteome (FIG. if). We thus reasoned that human cells could serve as a biorthogonal system for studying PopZ phase separation. When expressed in a human osteosarcoma U2OS cells PopZ phase-separated into micron-sized cytoplasmic condensates (FIG. 1*g*) that underwent spontaneous fusion events (FIG. 1*h*) and experienced dynamic internal rearrangements, as assayed by FRAP. Importantly, even though they were expressed in human cells, PopZ condensates retained specificity for their bacterial client proteins, such as ChpT Lasker, K. et al., *Nat Microbiol* 5, 418-429 (2020)], and were distinct from human stress granules (FIG. 1*i*). Thus, PopZ is sufficient for condensation and client recruitment, and human cells serve as an independent platform to study its behavior.

PopZ IDR Tunes the Microdomain Viscosity

PopZ is composed of three functional regions [Bowman, G. R. et al., *Mol Microbiol* 90, 776-795 (2013); Holmes, J. A. et al., *Proc Natl Acad Sci USA* 113, 12490-12495 (2016)](FIG. 2*a*, FIG. 6*a*): (i) a short N-terminal predicted helical region (H1) used for client binding [Holmes, J. A. et al., *Proc Natl Acad Sci USA* 113, 12490-12495 (2016); Nordyke, C. T. et al., *J Mol Biol* (2020), (ii) a 78 amino-acid (aa) IDR (IDR-78) [Nordyke, C. T. et al., *J Mol Biol* (2020)], and (iii) a helical C-terminal region (H2, H3, and H4) which is required and sufficient for PopZ self-oligomerization [Bowman, G. R. et al., *Mol Microbiol* 90, 776-795 (2013)]. To define the molecular features driving phase separation of PopZ, we determined the contribution of each of these domains to condensation in human and *Caulobacter* cells. PopZ mutants missing either the N-terminal region (Δ1-23) or the IDR (Δ24-101) were able to form condensates in both cell types (FIG. 2*b*). Deletion of the IDR resulted in the formation of irregular gel-like condensates characterized by arrested fusion events in human cells (FIG. 2*b*) while producing dense microdomains in *Caulobacter* (FIG. 2*b*). In contrast, deleting any of the three predicted C-terminal helical regions (Δ102-132, Δ133-156, and A157-177) drastically reduced visible PopZ condensates (FIG. 2*b*). Therefore, the C-terminal helices are required for the formation of condensates, and the IDR may play a role in tuning their material properties.

The architecture of the PopZ protein from *Caulobacter crescentus* is conserved not only within the Caulobacterales order, to which *Caulobacter crescentus* belongs (FIG. 2*c*), but also across all α-proteobacteria (FIG. 6*b*). All PopZ proteins consist of a short helical N-terminal region, an IDR, and a helical C-terminal region. The C-terminal region is divided into two sub-modules: a region that includes helix 2, which varies in length and helicity, and a region that includes helices 3 and 4, which is highly conserved. Further, despite showing little sequence conservation, the IDR length exhibits a narrow distribution in Caulobacterales with a mean of 93 ±1 aa (FIG. 2*d*), while other clades of α-proteobacteria occupy different length distributions (FIG. 6*c*).

To better characterize the PopZ linker we performed all-atoms simulations. We found the linker adopts an extended conformation, with a radius of gyration ($R_G$) of 34.4±4.8 Å and an apparent scaling exponent ($v^{app}$) of 0.7, corresponding to a self-repulsing polyelectrolyte (FIG. 2*e*). These estimates are in agreement with scaling exponents measured for other highly charged IDRs [Hofmann, H. et al., *Proc Natl Acad Sci USA* 109, 16155-16160 (2012); Sorensen, C. S. & Kjaergaard, M., *Proc Natl Acad Sci USA* 116, 23124-23131 (2019)]. Due to electrostatic repulsion between negatively charged residues in the linker and the high proline content the linker length and the global dimensions are tightly coupled (FIG. 2*e*). These results suggest that the evolution of the IDR length might be constrained.

We generated PopZ mutants with a truncated or expanded IDR; namely, IDR-40, corresponding to half the wild-type IDR length and an IDR-156, corresponding to double the length of the wild-type IDR. We tested their ability to form condensates in human cells by measuring partition coefficients compared to wild type PopZ. First, we mapped an eGFP-PopZ phase diagram as a function of concentration and IDR length. For any phase separating protein, condensates emerge as the cytoplasmic concentration exceeds the saturation concentration ($C_{sat}$). At high cytoplasmic concentrations ($C_D$), the system can then move to the dense phase regime characterized by the cytoplasm being taken over by one large droplet. We indeed observed that PopZ could occur in dilute, demixed, and dense regimes, as a function of its cytoplasmic concentration (FIG. 2*f*). Halving the PopZ IDR (IDR-40) decreased $C_{sat}$ and increased the $C_D$, compared to wild-type PopZ. In contrast, doubling the PopZ IDR (IDR-156) increased $C_{sat}$ and decreased $C_D$, resulting in a narrower two-phase window (FIG. 2*f*). Finally, increasing the IDR length decreased PopZ partitioning (FIG. 2*g*) and increased FRAP dynamics (FIG. 2*i*) in human cells. Collectively, our data suggest that the material properties of PopZ condensates are dependent on its IDR length.

Given the IDR offers one means to tune PopZ material properties, we wondered if altering the degree of multivalency could be used as an orthogonal control parameter. We increased the valency of the C-terminal region containing three helices (trivalent) by repeating the last highly conserved helix-turn-helix motif (FIG. 2*c*), resulting in PopZ variants carrying five C-terminal helices (pentavalent) (FIG.

2*h*). We found that pentavalent PopZ condensates had strongly reduced FRAP dynamics, compared to wild-type trivalent PopZ. Combining IDR-156 with a pentavalent oligomerization domain (OD) normalized the FRAP dynamics to a physiological range (FIG. 2*i*). Taken together, our work reveals two independent knobs through which we can tune the material properties of PopZ condensate, providing robust design principles for synthetic engineering of customizable condensates.

Maintaining PopZ as a Viscous Liquid is Essential for Cell Viability

To test whether IDR length-dependent changes in PopZ condensate viscosity would affect biological function, we expressed IDR-48 and IDR-156 PopZ mutants in ΔpopZ *Caulobacter* cells (FIG. 3*a*). The FRAP dynamics of these mutants were consistent between *Caulobacter* and human cells (FIG. 3*b*). IDR-48 PopZ condensates showed slightly slower FRAP dynamics compared to wild-type PopZ condensates (FIG. 3*b*). ΔpopZ cells expressing IDR-48 PopZ behaved similarly to wild-type in terms of cell length (FIG. 3*c*), PopZ localization to both poles, and cell growth (FIG. 3*d*). In contrast, expressing IDR-156 PopZ in a ΔpopZ background led to filamentous and largely stalkless cells (FIG. 3*c*) with severe fitness loss (FIG. 3*d*). Time-lapse images of these cells showed PopZ condensates that left the pole and diffused across the entire cell. In addition, tomography data revealed that these IDR-156 condensates retain their ability to form a barrier against ribosomes (FIG. 3*e*,). Thus, IDR-156 dynamics led to a constant reorganization of the cytosol and aberrant cell division.

Given the ability to rescue PopZ condensate material properties by combining IDR-156 with the pentavalent C-terminal region, we reasoned that this 'double mutant' would rescue function and fitness from the 'single mutant' defects observed for cells with IDR-156. In line with our expectation, PopZ with IDR-156 and pentavalent C-terminal region restored FRAP dynamics and localization to the poles (FIG. 3*b*). We further found that in this background, cell length, stalk formation, and viability are restored (FIG. 3*c,d*). Moreover, disrupting the material state by expressing pentavalent PopZ with the wild-type IDR-78 led to solid condensates localized to a single-pole (FIG. 3*be*), with stalkless cells and arrested growth (FIG. 3*a,d*). Collectively, our data reveal that too solid-like or too fluid-like microdomains are non-functional, suggesting that the function of the PopZ microdomain is intimately linked to its material properties, which have been precisely tuned to meet the cell's needs. As the valency of the OD can restore IDR length phenotypes and vice versa, we suggest that a tight balance of opposing forces mediated by the IDR and the OD define this physiological window.

The Net Charge and Charge Distribution of the IDR are Conserved and Tune the Material Properties of the PopZ Condensate In addition to conserved length (FIG. 2*d*), the IDR shows conservation of its strong enrichment for acidic and proline residues across Caulobacterales, with −0.28 net charge per residue and prolines constituting 29% of the IDR residues (FIG. 4*a,b*). Indeed, net charge and proline content are strongly correlated with increased $R_G$ in IDRs [Marsh, J. A. & Forman-Kay, J. D., *Biophys J* 98, 2383-2390 (2010)], which may explain the high $R_G$ value predicted for the PopZ IDR by all-atom simulations (FIG. 2*e*). To test whether amino acid content plays a role in the viscosity of the PopZ microdomain, we substituted acidic residues for asparagine and proline residues for glycine. Decreasing the negative charge of the linker reduced condensate fluidity in human cells as measured by FRAP dynamics of PopZ while substituting prolines for glycines slightly increased condensate fluidity (FIG. 4*c*). Our data suggest that electrostatic repulsion results in a more linear expansion of the linker region, which is mildly counteracted by proline residues via increased backbone rigidity or the formation of poly-proline helices [Martin, E. W. & Holehouse, A. S., *Emerg Top Life Sci*, doi:10.1042/ETLS20190164 (2020)]. Notably, as was the case for IDR length mutants, the FRAP dynamics of these IDR composition mutants observed in human cells correlated with their functionality in a APopZ *Caulobacter* background (FIG. 4*d*).

Since drastically changing the amino acid composition may affect several linker properties at once, we evaluated the role of potentially conserved primary sequence features. This allows us to explicitly test an alternative hypothesis—that the highly-charged IDR functions as a solubility tag, penalizing phase separation as a function of length. Accordingly, we constructed 17 scrambled versions of the IDR and measured their FRAP dynamics in human cells. We calculated primary sequence features for all of these mutants (Methods) and performed regression analysis to test which combination of features best explains the measured FRAP dynamics. We found that a combination of differential N-versus C acidity and differential proline enrichment best predicted experimental data with an R-square of 0.86. Notably, the values of the features used in the regression model show a narrow distribution across Caulobacterales, despite large differences in the actual primary IDR sequence.

Scramble 5 and scramble 17, with opposing differential N-versus C acidity, give rise to less dynamic or more fluid PopZ condensate compared to the wild-type protein (FIG. 4*e,f*). Similar to our observations for IDR length and composition mutants, the FRAP dynamics of these scrambled IDR mutants correlated directly with biological function-expression of scramble 17 was toxic to *Caulobacter* cells (FIG. 4*f*). Because PopZ condensation is driven by OD-OD interactions (FIG. 2*a*), we asked whether segregation of the IDR acidity close to (L5) or away from (L17) the OD could modulate these OD-OD interactions. We performed all-atom simulations on wild-type PopZ, scramble 5, and scramble 17 and calculated the degree of interactions between the IDR and the OD. We found that IDR scramble 17 tends to interact more with its adjacent OD, compared to the wild-type IDR, while IDR scramble 5 tends to interact less with its adjacent OD. These findings suggest that competing IDR-OD and OD-OD interactions can regulate the dynamics of PopZ condensates.

Cumulatively, our results show that the function of the PopZ microdomain is tuned by its material properties. By dissecting the molecular grammar of the PopZ IDR and the OD, we propose that the PopZ material properties can be explained by a molecular push-pull strategy. The valency of the OD drives condensation, while the electrostatic repulsion of the IDR fluidizes the condensates. Moreover, we show that three hierarchical IDR features can be tuned to alter its repulsive nature. While IDR length and charge drive linker extension, local variations in IDR acidity can promote competing IDR-OD interactions. By subsequently testing an array of carefully designed mutants, we provide for the first-time evidence that condensate material properties can tune organismal fitness. Looking at the evolutionary landscape of PopZ, we find evidence suggesting that tunable IDR properties may be under selective pressure, and therefore could have helped the boom in phenotypic and ecological diversity among α-proteobacteria.

An Engineered PopTag Phase Separates into Cytoplasmic Condensates with Tunable Material Properties.

The simple modular domain architecture of PopZ, with an N-terminal client binding domain, and discrete domains that tune and drive phase separation, highlights a novel topology that is distinct from most of the currently characterized phase separating proteins (FIG. 5*a*). Because PopZ condensates do not interfere with human membraneless organelles such as stress granules (FIG. 1*i*) and seemed well-tolerated by cells, we harnessed PopZ to engineer this simple design into a modular platform for the generation of designer condensates. We isolated the oligomerization domain and found it to be sufficient to drive condensate formation in human cells (FIG. 7*a*). This "PopTag" is a C-terminal protein tag of only 76 amino acids, an order of magnitude smaller than some of the currently available fusion constructs [Shin, Y. et al., *Cell* 168, 159-171 (2017)]. Just as was the case for PopZ, the material properties of these condensates could be tuned by the addition of a spacer (FIG. 7*b*). To functionalize these designer condensates, we fused the PopTag to different "actor" domains. For example, by fusing the PopTag to a drug-inducible degron, we generated condensates whose temporal expression is under tight pharmacological control (FIG. 7*c*). We also encoded biochemical reactions into these designer condensates. Fusing the PopTag to well-folded enzymes led to their condensation in the cytoplasm (FIG. 5*b*). To assay whether such enzymes would retain activity inside these droplets, we used TurboID, an engineered biotinylating enzyme [Guntas, G. et al., *Proc Natl Acad Sci US* A 112, 112-117 (2015)]. Treating cells with biotin resulted in the biotinylation of these TurboID-PopTag condensates, as assayed by streptavidin staining (FIG. 5*b*), demonstrating that PopTag-generated condensates facilitate the assembly of enzymatic microreactors.

Accumulating data indicates that cellular condensates are spatially regulated and can interact with other subcellular structures and compartments [Boeynaems, S. et al., *Trends Cell Biol* 28, 420-435 (2018); Wiegand, T. & Hyman, A. A., *Emerg Top Life Sci*, doi:10.1042/ETLS20190174 (2020)]. To test whether our designer condensates would be amenable to such specific subcellular localization, we fused the PopTag to different "cellular anchors"—tethering the condensates in the plasma membrane, on microtubules, or on the surface of lipid droplets (FIG. 5*c*). Moreover, when we target the PopTag to the actin cytoskeleton by fusing it to the beta spectrin-derived actin-binding domain, the straight actin bundles of the cytoskeleton would deform and buckle, while this was not the case when we expressed the actin-binding domain by itself (FIG. 5*d*). This observation suggests that cytoplasmic condensates can exert force upon the cytoskeleton, akin to nuclear bodies interacting with the genome [Shin, Y. et al., *Cell* 175, 1481-1491 (2018)] and TIS-granules embedded between endoplasmic reticulum tubules [Ma, W., Zhen, G., Xie, W. & Mayr, C., *bioRxiv*, 2020.2002.2014.949503, doi:10.1101/2020.02.14.949503 (2020)]. These different chimeric fusions highlight the versatility of the PopTag, which can facilitate engineering designer condensates that can differentially localize, compartmentalize biochemical reactions, or exert forces on cellular structural elements.

We next wondered if we could functionalize the PopTag with a nanobody to facilitate specific and targeted sequestration of specific clients. In order to more closely mimic the endogenous function of PopZ in *Caulobacter*, we focused on the N-terminal helix. PopZ uses this domain to specifically recruit client proteins to the microdomain. We replaced the N-terminal helix with a GFP-targeting nanobody (FIG. 5*e*) to create "NanoPop". These NanoPop condensates were able to efficiently sequester GFP or GFP-tagged proteins into cytoplasmic condensates (FIG. 5*e*, FIG. 7).

As a proof-of-concept study to test whether designer condensates can recapitulate specific cellular processes, we focused on the role of protein phase separation in nucleo-cytoplasmic transport. Nuclear import is mediated by karyopherins or importins, a class of proteins that binds to and facilitate the translation of client proteins through the nuclear pore complex. (FIG. 5*f*). It was recently shown that the formation of stress granules coincides with nuclear import defects, presumably due to disruption of karyopherin availability [Zhang, K. et al., *Cell* 173, 958-971 (2018); Vanneste, J. et al., *Sci Rep* 9, 15728 (2019)]. While cellular stress is a normally transient event, persistent nuclear import dysregulation has been implicated in several neurodegenerative disorders [Woerner, A. C. et al., *Science* 351, 173-176 (2016); Boeynaems, S. et al., *Acta Neuropathol* 132, 159-173 (2016)]. A key and unanswered question is whether the cytoplasmic retention of karyopherins is a direct consequence of their interaction with such liquid-like cytoplasmic assemblies, or an indirect effect of cellular stress. To answer this question we used NanoPop condensates to test whether the sequestration of karyopherins to synthetic cytoplasmic condensates is sufficient to block nuclear import of the client protein NPM1. We endogenously tagged the karyopherin KPNA2 with GFP in a human HapI cell line. Expressing GFP-NanoPop in these cells resulted in the recruitment of KPNA2 to cytoplasmic condensates and its subsequent nuclear depletion, with a concomitant decrease in nuclear NPM1 import. In contrast, when the nanobody was expressed by alone no such defects were observed (FIG. 5*e*). Beyond simply reducing client import, NPM1 was recruited to the NanoPop condensates, showing that we were able to sequester intact complexes of client-transporter. Thus, our synthetic condensates are sufficient to drive nucleocytoplasmic transport defects in a karyopherin-dependent manner. This experiment shows that tunable and functionalizable designer condensates provide a new means to untangle the contributions of specific molecular events to biological and pathological processes.

As IDRs code for 4% of bacterial proteomes, unlike 30-50% of eukaryotic proteomes [van der Lee, R. et al., *Chem Rev* 114, 6589-6631 (2014)], their role in bacteria physiology was largely overlooked. With accumulating evidence for abundance of biomolecular condensates in bacterial cells [Azaldegui, C. A., Vecchiarelli, A. G. & Biteen, J. S., *Biophys J*, doi:10.1016/j.bpj.2020.09.023 (2020)], and the vital role IDRs play in their formation [Cohan, M. C. & Pappu, R. V., *Trends Biochem Sci* 45, 668-680 (2020)], the importance of these proteins is gaining appreciation. Bacterial IDRs differ from their eukaryotic counterpartners, not only in proteome abundance, but also in amino acid composition (Extended Data FIG. 1*c* and [van der Lee, R. et al., *Chem Rev* 114, 6589-6631 (2014); Basile, W., Salvatore, M., Bassot, C. & Elofsson, A, *PLoS Comput Biol* 15 (2019)]). These differences open new possibilities to characterize bacterial IDRs and ultimately use them to engineer synthetic biomolecules condensates to better control the phase behavior in eukaryotic cells.

Here we studied the biophysical properties of the intrinsically disordered protein PopZ from the bacterium *Caulobacter crescentus*. We previously showed that PopZ forms membraneless condensates at the poles and selectively sequesters kinase-signaling cascades to regulate asymmetric cell division [Bowman, G. R. et al., *Cell* 134, 945-955 (2008); Ebersbach, G. et al., *Cell* 134, 956-968 (2008); Lasker, K. et al., *Nat Microbiol* 5, 418-429 (2020)]. We found that PopZ self-condenses by liquid-liquid phase separation in vivo both in *Caulobacter* and human cells (FIG. 1). We further showed that unlike most other phase separated IDPs, the disordered region of PopZ is used to not used to drive phase separation but rather to modulate the material properties of the condensate. Instead, a short structured helical domain is necessary and sufficient for phase separation (FIG. 2).We identified knobs that can be used to alter material properties, these include the IDR length, fraction of prolines and acidic residues, as well as the distribution of the acidic residues in the sequences (FIG. 4). Finally, we showed that the configuration of these knobs is conserved across PopZ homologs and lead to a viscous liquid PopZ condensate. Deviating from this configuration, either by making it too liquid or too solid, results in loss of fitness (FIGS. 3,4).

Combined, our studies reveal a simple modular biomolecular platform, comprising of client recognition, tuner, and driver modules, allows for the engineering of a virtually unlimited set of designer condensates for synthetic biology (FIG. 5*g*).

The above examples are provided to illustrate the invention but not to limit its scope. Other variants of the invention will be readily apparent to one of ordinary skill in the art and are encompassed by the appended claims. All publications, databases, internet sources, patents, patent applications, and accession numbers cited herein are hereby incorporated by reference in their entireties for all purposes.

What is claimed is:

1. A fusion protein comprising an amino acid sequence linked to a polypeptide sequence comprising SEQ ID NO: 1, or a variant thereof as set forth in Table 1, wherein the amino acid sequence is heterologous to the polypeptide sequence.

2. The fusion protein of claim 1, wherein the polypeptide sequence is at least 95% identical to SEQ ID NO:1.

3. The fusion protein of claim 1, wherein the amino acid sequence is an epitope-binding polypeptide.

4. The fusion protein of claim 3, wherein the epitope-binding polypeptide is a single domain antibody or a single-chain variable fragment (scfv) or comprises an immunoglobulin heavy chain variable region.

5. The fusion protein of claim 1, wherein the amino acid sequence is a target-binding polypeptide.

6. The fusion protein of claim 1, wherein the amino acid sequence comprises a fluorescent protein.

7. The fusion protein of claim 1, wherein the amino acid sequence comprises an enzyme.

8. A polynucleotide comprising a nucleic acid sequence that encodes the fusion protein of claim 1.

9. The polynucleotide of claim 8, comprising a promoter operably linked to the nucleic acid sequence.

10. An in vitro or ex vivo cell comprising a polynucleotide encoding the fusion protein of claim 1, wherein the cell expresses the fusion protein.

11. The cell of claim 10, wherein the cell is a eukaryotic cell.

12. The cell of claim 11, wherein the eukaryotic cell is a mammalian cell.

13. The cell of claim 10, wherein the cell comprises:

a. a first polynucleotide encoding a first fusion protein comprising SEQ ID NO:1 and a first heterologous amino acid sequence and;

b. a second polypeptide encoding a second fusion protein comprising SEQ ID NO:1 and a second heterologous amino acid sequence, wherein the first heterologous amino acid sequence and first heterologous amino acid sequence are different heterologous amino acid sequences.

14. The cell of claim 13, wherein the different heterologous amino acid sequences are different enzymes.

15. A method of purifying a product from a cell, the method comprising, expressing in the cell the fusion protein of claim 1, wherein the fusion protein forms compartments in the cell, wherein the compartments are membraneless synthetic organelles;

lysing the cell; and isolating the compartments from cell lysate material, wherein the compartments comprise the product, thereby purifying the product from the cell.

16. The method of claim 15, wherein the product is formed by performing a reaction in the compartments.

17. The method of claim 16, wherein the amino acid sequence comprises an enzyme and the enzyme catalyzes production of the product.

18. The method of claim 15, wherein the cell produces the product and the amino acid sequence comprises a binding polypeptide that binds the product, thereby binding the product to the compartment.

19. The method of claim 15, comprising a step of performing a reaction in the compartments to form the product after the expressing and before the lysing.

20. The cell of claim 10, wherein the polypeptide sequence comprises SEQ ID NO:1.

21. The fusion protein of claim 1, wherein the polypeptide sequence comprises SEQ ID NO:1.

* * * * *

```
                        SEQUENCE LISTING


<160> NUMBER OF SEQ ID NOS: 152

<210> SEQ ID NO 1
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Ala Glu Gln Leu Val Gly Val Ser Ala Ala Ser Ala Ala Ala
1               5                   10                  15

Ser Ala Phe Gly Ser Leu Ser Ser Ala Leu Leu Met Pro Lys Asp Gly
            20                  25                  30

Arg Thr Leu Glu Asp Val Val Arg Glu Leu Leu Arg Pro Leu Leu Lys
        35                  40                  45

Glu Trp Leu Asp Gln Asn Leu Pro Arg Ile Val Glu Thr Lys Val Glu
    50                  55                  60

Glu Glu Val Gln Arg Ile Ser Arg Gly Arg Gly Ala
65                  70                  75


<210> SEQ ID NO 2
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: E or D
<220> FEATURE:
<221> NAME/KEY: MOD_RES
<222> LOCATION: (4)..(4)
<223> OTHER INFORMATION: E or D
<220> FEATURE:
<221> NAME/KEY: MOD_RES
<222> LOCATION: (41)..(41)
<223> OTHER INFORMATION: E or D
<220> FEATURE:
<221> NAME/KEY: MOD_RES
<222> LOCATION: (52)..(52)
<223> OTHER INFORMATION: D or E
<220> FEATURE:
<221> NAME/KEY: MOD_RES
<222> LOCATION: (60)..(60)
<223> OTHER INFORMATION: E or D
<220> FEATURE:
<221> NAME/KEY: MOD_RES
```

<222> LOCATION: (64)..(66)
<223> OTHER INFORMATION: E or D

<400> SEQUENCE: 2

```
Xaa Val Ala Xaa Gln Leu Val Gly Val Ser Ala Ala Ser Ala Ala Ala
1               5                   10                  15

Ser Ala Phe Gly Ser Leu Ser Ser Ala Leu Leu Met Pro Lys Asp Gly
            20                  25                  30

Arg Thr Leu Glu Asp Val Val Arg Xaa Leu Leu Arg Pro Leu Leu Lys
        35                  40                  45

Glu Trp Leu Xaa Gln Asn Leu Pro Arg Ile Val Xaa Thr Lys Val Xaa
    50                  55                  60

Xaa Xaa Val Gln Arg Ile Ser Arg Gly Arg Gly Ala
65                  70                  75
```

<210> SEQ ID NO 3
<211> LENGTH: 74
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 3

```
Ala Glu Gln Leu Val Gly Val Ser Ala Ala Ser Ala Ala Ala Ser Ala
1               5                   10                  15

Phe Gly Ser Leu Ser Ser Ala Leu Leu Met Pro Lys Asp Gly Arg Thr
            20                  25                  30

Leu Glu Asp Val Val Arg Glu Leu Leu Arg Pro Leu Leu Lys Glu Trp
        35                  40                  45

Leu Asp Gln Asn Leu Pro Arg Ile Val Glu Thr Lys Val Glu Glu Glu
    50                  55                  60

Val Gln Arg Ile Ser Arg Gly Arg Gly Ala
65                  70
```

<210> SEQ ID NO 4
<211> LENGTH: 75
<212> TYPE: PRT
<213> ORGANISM: Maricaulis sp.

<400> SEQUENCE: 4

```
Glu Val Ser Glu Gly Ile Met Ser Glu Pro Ala Ala Ser Ala Ala Met
1               5                   10                  15

Gly Ser Phe His Thr Leu Ala Asp Gln Ile Arg Ile Ser Glu Glu Glu
            20                  25                  30

Gly Arg Thr Leu Glu Gly Val Val Arg Ala Leu Leu Arg Pro Met Leu
        35                  40                  45

Lys Glu Trp Leu Asp Ala Asn Leu Pro Ser Ile Val Asp Glu Lys Val
    50                  55                  60

Gln Ala Glu Ile Asp Arg Val Ser Arg Arg Arg
65                  70                  75
```

<210> SEQ ID NO 5
<211> LENGTH: 68
<212> TYPE: PRT
<213> ORGANISM: Hyphomonas sp.

<400> SEQUENCE: 5

```
Glu Pro Leu Thr Asp Ala Asn Thr Ala Glu Ser Ala Ala Gly Ala Leu
1               5                   10                  15
```

```
Gly Lys Leu Ile Ser Lys Met Asp Ile Gly Ser Asp Asn Thr Leu Glu
            20                  25                  30

Gly Leu Val Arg Glu Leu Leu Lys Pro Met Val Lys Glu Trp Leu Asp
        35                  40                  45

Ala Asn Leu Ala Arg Ile Val Glu Glu Lys Val Glu Ala Glu Val Gln
    50                  55                  60

Arg Ile Ala Arg
65


<210> SEQ ID NO 6
<211> LENGTH: 72
<212> TYPE: PRT
<213> ORGANISM: Methylovirgula sp.

<400> SEQUENCE: 6

Glu Leu Ser Asp Val Leu Leu Ser Pro Ala Ala Ser Glu Ser Val Ala
1               5                   10                  15

His Ala Phe Asp Thr Leu Asp Arg Thr Leu Lys Met Gln Asn Asp Gly
            20                  25                  30

Thr Leu Glu Asp Met Ser Arg Glu Leu Leu Arg Pro Met Leu Lys Ala
        35                  40                  45

Trp Leu Asp Glu Asn Leu Pro Ala Leu Val Glu Arg Leu Val Lys Ala
    50                  55                  60

Glu Ile Glu Arg Val Val Arg Gly
65                  70


<210> SEQ ID NO 7
<211> LENGTH: 70
<212> TYPE: PRT
<213> ORGANISM: Unknown
<220> FEATURE:
<223> OTHER INFORMATION: Description of Unknown:
      Rhabdaerophilum calidifontis sequence

<400> SEQUENCE: 7

Glu Arg Ile Met Ser Asp Asn Thr Lys Ala Leu Val Ser Gln Ala Phe
1               5                   10                  15

Gln Thr Leu Ser Arg His Thr Ala Met Pro Ala Met Gly Arg Ser Leu
            20                  25                  30

Glu Asp Val Val Val Glu Leu Leu Arg Pro Met Leu Arg Asp Trp Ile
        35                  40                  45

Asp Ser His Leu Pro Ala Ile Val Glu Lys His Val Arg Ala Glu Ile
    50                  55                  60

Glu Arg Val Ala Arg Gly
65                  70


<210> SEQ ID NO 8
<211> LENGTH: 72
<212> TYPE: PRT
<213> ORGANISM: Pseudoxanthobacter soli

<400> SEQUENCE: 8

Thr Ala Glu Asp Arg Ile Leu Ser Glu Ala Ala Asp Ala Ala Ile Gly
1               5                   10                  15

Ala Ser Phe Asn Val Leu Ser Arg Thr Val Val Ala Gln Asn Pro His
            20                  25                  30

Thr Ile Glu Asp Leu Val Arg Asp Met Leu Arg Pro Met Leu Gln Ser
        35                  40                  45
```

```
Trp Leu Asp Glu Asn Leu Pro Arg Ile Val Glu Arg Gln Val Arg Ala
    50                  55                  60

Glu Ile Glu Arg Val Ser Arg Gly
65                  70


<210> SEQ ID NO 9
<211> LENGTH: 72
<212> TYPE: PRT
<213> ORGANISM: Devosia sp.

<400> SEQUENCE: 9

Asp Ile Ala Glu Glu Leu Leu Glu Pro Ala Thr Lys Ala Ala Val Arg
1               5                   10                  15

Ser Thr Phe Ala Arg Leu Asn Gly Leu Ser Ala Val Ala Pro Gly Ile
            20                  25                  30

Thr Leu Glu Asp Leu Ile Arg Asp Met Met Arg Pro Met Leu Lys Glu
        35                  40                  45

Trp Leu Asp Glu Asn Leu Pro Ala Val Val Glu Arg Met Val Glu Lys
    50                  55                  60

Glu Ile Glu Arg Val Ser Arg Gly
65                  70


<210> SEQ ID NO 10
<211> LENGTH: 68
<212> TYPE: PRT
<213> ORGANISM: Unknown
<220> FEATURE:
<223> OTHER INFORMATION: Description of Unknown:
      Alphaproteobacteria bacterium sequence

<400> SEQUENCE: 10

Glu Thr Leu Thr Ser Ala Pro Val Ala Gln His Ala Ala Gly Ala Leu
1               5                   10                  15

Gly Lys Leu Met Gly Ser Met Leu Val Ser Ser Thr Gly Thr Leu Asp
            20                  25                  30

Asp Val Val Arg Glu Leu Leu Lys Pro Met Leu Lys Glu Trp Leu Asp
        35                  40                  45

Ala Asn Leu Pro Gln Leu Val Glu Ala Glu Val Ala Lys Glu Ile Asp
    50                  55                  60

Arg Ile Arg Arg
65


<210> SEQ ID NO 11
<211> LENGTH: 62
<212> TYPE: PRT
<213> ORGANISM: Unknown
<220> FEATURE:
<223> OTHER INFORMATION: Description of Unknown:
      Parvularculaceae bacterium sequence

<400> SEQUENCE: 11

Ala Ala Val Ala Glu Asp Ala Phe Lys Ser Leu Asn Gln Ser Ile Arg
1               5                   10                  15

Ile Ser Gly Gln Ser Glu Lys Thr Leu Glu Asp Leu Val Thr Asp Leu
            20                  25                  30

Leu Arg Pro Leu Met Lys Glu Trp Leu Asp Glu Asn Leu Pro Gln Ile
        35                  40                  45

Val Glu Asp Lys Val Gln Asp Glu Val Thr Arg Ile Ala Arg
    50                  55                  60
```

```
<210> SEQ ID NO 12
<211> LENGTH: 68
<212> TYPE: PRT
<213> ORGANISM: Unknown
<220> FEATURE:
<223> OTHER INFORMATION: Description of Unknown:
      Pseudorhodoplanes sp. sequence

<400> SEQUENCE: 12

Leu Leu Ser Ser Ala Ala Ser His Ala Val Asp His Ala Phe Ser Gln
1               5                   10                  15

Phe Thr Gln Thr Val Phe Thr Gln Asn Gly Arg Thr Ile Glu Asp Val
            20                  25                  30

Gly Arg Asp Met Leu Arg Pro Met Leu Lys Ser Trp Leu Asp Asp Asn
        35                  40                  45

Leu Pro Gly Leu Val Glu Arg Leu Val Arg Ala Glu Ile Glu Arg Val
    50                  55                  60

Ser Arg Gly Arg
65


<210> SEQ ID NO 13
<211> LENGTH: 70
<212> TYPE: PRT
<213> ORGANISM: Breoghania corrubedonensis

<400> SEQUENCE: 13

Asp Arg Leu Met Ser Asp Asn Thr Asp Thr Thr Val His Ser Ala Phe
1               5                   10                  15

Ala Ser Leu Ser Asn Thr Val Leu Ala Ala Asn Ser Arg Thr Leu Asp
            20                  25                  30

Glu Leu Val Arg Glu Met Leu Arg Pro Met Ile Lys Gly Trp Leu Asp
        35                  40                  45

Asp Asn Leu Pro Thr Met Val Glu Arg Met Val Arg Gln Glu Ile Glu
    50                  55                  60

Arg Val Thr Arg Gly Arg
65                  70


<210> SEQ ID NO 14
<211> LENGTH: 78
<212> TYPE: PRT
<213> ORGANISM: Unknown
<220> FEATURE:
<223> OTHER INFORMATION: Description of Unknown:
      Rhodospirillaceae bacterium sequence

<400> SEQUENCE: 14

Asp Ser Leu Leu Asp Lys Thr Ala Ala Ala Ala Ala Thr Glu Ser Phe
1               5                   10                  15

Gly Glu Leu Thr Lys Ala Val Ile Lys Glu Asp Gly Pro Gly Ile Gln
            20                  25                  30

Leu Gly Ser Leu Thr Glu Lys Thr Leu Glu Asp Leu Leu Lys Glu Leu
        35                  40                  45

Leu Arg Pro Met Leu Lys Glu Trp Leu Asp Gln Asn Leu Pro Ser Ile
    50                  55                  60

Thr Glu Lys Leu Val Arg Lys Glu Ile Glu Arg Thr Ala Arg
65                  70                  75


<210> SEQ ID NO 15
<211> LENGTH: 82
<212> TYPE: PRT
<213> ORGANISM: Unknown
```

```
<220> FEATURE:
<223> OTHER INFORMATION: Description of Unknown:
      Caulobacterales bacterium GWE1_67_11 sequence
<220> FEATURE:
<221> NAME/KEY: MOD_RES
<222> LOCATION: (11)..(13)
<223> OTHER INFORMATION: Any amino acid

<400> SEQUENCE: 15

Asp Ala Leu Val Gly Glu Ser Ala Ala Ala Xaa Xaa Xaa Ser Ala Phe
1               5                   10                  15

Ala Gly Leu Ala Ala Ser Phe Lys Lys Pro Glu Pro Ala Ala Ala Ser
            20                  25                  30

Ser Thr Glu Met Pro Phe Val Ser Gly Asn Thr Val Glu Ala Met Val
        35                  40                  45

Ala Glu Met Leu Arg Pro Met Leu Lys Asp Trp Leu Asp Asn Asn Leu
    50                  55                  60

Pro Ala Ile Val Glu Ala Ala Val Gln Arg Glu Val Glu Arg Ile Ala
65                  70                  75                  80

Arg Ser


<210> SEQ ID NO 16
<211> LENGTH: 72
<212> TYPE: PRT
<213> ORGANISM: Aureimonas sp.

<400> SEQUENCE: 16

Glu Gly Ala Ser Ala Leu Leu Ser Ala Gln Ala Gly Asp Gln Val Ala
1               5                   10                  15

Ala Ala Phe Asp Asp Leu Thr Arg Ala Ile Arg Asp Gly Gln Met Arg
            20                  25                  30

Ser Met Glu Glu Met Ala Arg Glu Met Met Arg Pro Met Leu Gln Glu
        35                  40                  45

Trp Leu Asp Asp Asn Leu Pro Arg Ile Val Glu Arg Leu Val Arg Asp
    50                  55                  60

Glu Ile Glu Arg Ile Ala Arg Gly
65                  70


<210> SEQ ID NO 17
<211> LENGTH: 73
<212> TYPE: PRT
<213> ORGANISM: Methylobacterium sp.

<400> SEQUENCE: 17

Gln Val Ser Glu Arg Leu Val Ser Ser His Thr Val Glu Ser Val Gly
1               5                   10                  15

Gln Asn Phe His Leu Leu Ala Gln Thr Val Leu Ser Gln Asn Ala Arg
            20                  25                  30

Thr Leu Glu Asp Leu Val Gln Asp Met Leu Arg Pro Met Leu Lys Gly
        35                  40                  45

Trp Leu Asp Glu Asn Leu Pro His Met Val Glu Arg Leu Val Arg Ala
    50                  55                  60

Glu Ile Glu Arg Val Ala Arg Gly Arg
65                  70


<210> SEQ ID NO 18
<211> LENGTH: 68
<212> TYPE: PRT
<213> ORGANISM: Azorhizobium sp.
```

<400> SEQUENCE: 18

Lys Asp Leu Leu Ser Pro Ser Val Asp Ala Val Val Ala Ala Ala Phe
1 5 10 15

Glu Ser Leu Gly Asp Met Val Leu Pro Ala His Glu Arg Thr Val Glu
20 25 30

Asp Leu Val Lys Glu Ile Leu Arg Pro Met Leu Lys Glu Trp Leu Asp
35 40 45

Ala His Leu Pro Asp Ile Val Glu Arg Leu Val Arg Ala Glu Ile Glu
50 55 60

Arg Val Ser Arg
65

<210> SEQ ID NO 19
<211> LENGTH: 70
<212> TYPE: PRT
<213> ORGANISM: Microvirga sp.

<400> SEQUENCE: 19

Asp Ala Leu Leu Ser Gly Ala Ala Asp Ala Cys Val Ala Asp Ala Phe
1 5 10 15

Gly Arg Leu Gly Ala Ala Val Ala Gly Arg Ser Ser Pro Ala Thr Met
20 25 30

Glu Asp Phe Val Ala Glu Leu Leu Arg Pro Leu Leu Arg Glu Trp Leu
35 40 45

Asp Glu Asn Leu Pro Pro Leu Val Glu Arg Leu Val Arg Ala Glu Ile
50 55 60

Glu Arg Ile Ser Arg Gly
65 70

<210> SEQ ID NO 20
<211> LENGTH: 73
<212> TYPE: PRT
<213> ORGANISM: Unknown
<220> FEATURE:
<223> OTHER INFORMATION: Description of Unknown:
Rhodobiaceae bacterium sequence

<400> SEQUENCE: 20

Glu Pro Leu Ile Ser Gly Ala Thr Glu Ala Ala Thr Ala Ala Ala Phe
1 5 10 15

Gly Ser Leu Ala Ser Ser Ile Leu Thr Ser Ser Gly Asp Ala Arg Thr
20 25 30

Leu Glu Asp Leu Val Ala Asp Met Leu Arg Pro Met Leu Lys Asp Trp
35 40 45

Met Asp Lys Asn Leu Pro Ser Leu Val Glu Gln Leu Val Arg Glu Glu
50 55 60

Ile Glu Arg Val Ala Arg Arg Gly Arg
65 70

<210> SEQ ID NO 21
<211> LENGTH: 72
<212> TYPE: PRT
<213> ORGANISM: Unknown
<220> FEATURE:
<223> OTHER INFORMATION: Description of Unknown:
Hyphomonadaceae bacterium sequence

<400> SEQUENCE: 21

Glu Ala Leu Thr Asp Glu Arg Ile Ala Gly Ala Ala Ala Thr Ala Leu
1 5 10 15

Gly Lys Leu Met Val Lys Arg Ser Ser Ser Glu Glu Glu Ala Asn Pro
20 25 30

Asn Thr Leu Asp Gly Leu Met Arg Glu Leu Leu Arg Pro Met Ile Lys
35 40 45

Glu Trp Leu Asp Ala Asn Leu Pro Ala Ile Val Glu Arg Lys Val Glu
50 55 60

Glu Glu Val Gln Arg Ile Ala Arg
65 70

<210> SEQ ID NO 22
<211> LENGTH: 77
<212> TYPE: PRT
<213> ORGANISM: Unknown
<220> FEATURE:
<223> OTHER INFORMATION: Description of Unknown:
Rhodospirillaceae bacterium sequence

<400> SEQUENCE: 22

Gly Glu Gly Leu Met Ser Gln Ser Ala Thr Met Ser Ser Ala Gly Ala
1 5 10 15

Ile Ala His Leu Asn Gln Ala Leu Leu Gly Asp Tyr Ser Asp Leu Leu
20 25 30

Gly Asn Met Gly Arg Met Thr Val Glu Asp Leu Val Arg Glu Leu Leu
35 40 45

Arg Pro Leu Leu Lys Glu Trp Leu Asp Arg Asn Leu Pro Pro Leu Val
50 55 60

Glu Gln Met Val Arg Asn Glu Ile Gln Arg Ile Val Arg
65 70 75

<210> SEQ ID NO 23
<211> LENGTH: 72
<212> TYPE: PRT
<213> ORGANISM: Unknown
<220> FEATURE:
<223> OTHER INFORMATION: Description of Unknown:
Alphaproteobacteria bacterium sequence

<400> SEQUENCE: 23

Ile Val Ser Asp Asp Val Ala Val Ala Ala Ser Ala Lys Phe Asp Gln
1 5 10 15

Leu Ser His Met Leu Val Arg Arg Tyr Pro Gly Ala Glu Asn Thr Leu
20 25 30

Glu Gly Leu Val Arg Asp Leu Leu Arg Pro Leu Leu Lys Glu Trp Leu
35 40 45

Asp Ala Asn Leu Pro Pro Leu Val Glu Glu Met Val Ala Arg Glu Ile
50 55 60

Glu Arg Ile Thr Arg Gly Lys Ser
65 70

<210> SEQ ID NO 24
<211> LENGTH: 70
<212> TYPE: PRT
<213> ORGANISM: Unknown
<220> FEATURE:
<223> OTHER INFORMATION: Description of Unknown:
Marinicauda sp. WD6-1 sequence

<400> SEQUENCE: 24

Leu Leu Gly Glu Ser Gln Ala Gly Val Ala Ser Ala Ala Phe Ala Ala
1 5 10 15

-continued

```
Leu Ser Glu Asn Leu Arg Val Ser Ser Gly Asn Gly Gln Thr Leu Glu
            20                  25                  30

Gly Ile Val Arg Glu Leu Met Lys Pro Met Leu Lys Gln Trp Leu Asp
        35                  40                  45

Glu Asn Leu Pro Thr Ile Val Glu Gln Lys Val Glu Glu Glu Ile Glu
    50                  55                  60

Arg Val Ala Arg Arg Arg
65                  70


<210> SEQ ID NO 25
<211> LENGTH: 72
<212> TYPE: PRT
<213> ORGANISM: Unknown
<220> FEATURE:
<223> OTHER INFORMATION: Description of Unknown:
      Proteobacteria bacterium HN_bin10 sequence

<400> SEQUENCE: 25

Thr Ala Asp Ala Ile Leu Ser Thr Pro Val Ala Ser Ala Ala Ala Gly
1               5                   10                  15

Ser Leu Ala Arg Leu Ala Gly Thr Leu Arg Ile Ser Asp Gln Pro Gly
            20                  25                  30

Gln Thr Val Glu Gly Val Val Arg Glu Leu Leu Lys Pro Met Leu Lys
        35                  40                  45

Glu Trp Leu Asp Arg Asn Leu Ala Ala Ile Val Glu Ala Arg Val Glu
    50                  55                  60

Ala Glu Leu Glu Arg Ile Ala Arg
65                  70


<210> SEQ ID NO 26
<211> LENGTH: 70
<212> TYPE: PRT
<213> ORGANISM: Pseudovibrio sp.

<400> SEQUENCE: 26

Asp Leu Thr Glu Thr Leu Ile Ser Ser Ala Thr Asp Gln Val Val Ser
1               5                   10                  15

Ser Ala Phe Asn Gly Leu Ala Asn Thr Val Leu Ser Lys Asn Ala Arg
            20                  25                  30

Thr Leu Glu Asp Met Val Ala Glu Met Leu Arg Pro Met Leu Lys Gly
        35                  40                  45

Trp Leu Asp Gln His Leu Pro Ser Val Val Glu Arg Leu Val Arg Gln
    50                  55                  60

Glu Ile Asp Arg Ile Ser
65                  70


<210> SEQ ID NO 27
<211> LENGTH: 75
<212> TYPE: PRT
<213> ORGANISM: Unknown
<220> FEATURE:
<223> OTHER INFORMATION: Description of Unknown:
      Alphaproteobacteria bacterium sequence

<400> SEQUENCE: 27

Leu Val Ser Ser His Thr Gln Ser Ala Val Asn Gln Ala Phe Ser Met
1               5                   10                  15

Leu Ser Arg Ser Asn Thr Asn Asp Met Pro Ile Ala Gln Gly Asp Gly
            20                  25                  30

Arg Thr Leu Glu Asp Ile Val Ala Gln Met Leu Arg Pro Met Leu Lys
```

```
        35                  40                  45

Asp Trp Leu Glu Asp Asn Leu Pro Ala Met Val Glu Arg Ile Val Arg
    50                  55                  60

Glu Glu Val Glu Arg Ala Ser Arg Thr Thr Gly
65                  70                  75


<210> SEQ ID NO 28
<211> LENGTH: 75
<212> TYPE: PRT
<213> ORGANISM: Unknown
<220> FEATURE:
<223> OTHER INFORMATION: Description of Unknown:
      Marinicaulis flavus sequence

<400> SEQUENCE: 28

Glu Ile Glu Asp Glu Ile Leu Asp Gln Thr Thr Ala Ala Ala Ala Ser
1               5                   10                  15

Lys Ala Phe Thr Thr Leu Ser Gln Ser Val Arg Val Ser Glu Gly Pro
            20                  25                  30

Gly Arg Thr Leu Glu Asp Ile Val Thr Glu Met Leu Arg Pro Met Val
        35                  40                  45

Lys Glu Trp Leu Asp Ala Asn Leu Pro Ala Ile Val Glu Glu Lys Val
    50                  55                  60

Glu Glu Glu Val Gln Arg Val Ala Arg Arg Arg
65                  70                  75


<210> SEQ ID NO 29
<211> LENGTH: 80
<212> TYPE: PRT
<213> ORGANISM: Devosia sp.

<400> SEQUENCE: 29

Asp Ile Ala Glu Gly Leu Leu Glu Thr Thr Thr Lys Ala Ala Val Arg
1               5                   10                  15

Ser Ser Ile Gly Lys Leu Gly Ala Ala Gly Leu Gly Thr Ile Ala Ser
            20                  25                  30

Pro Ala Leu Gly Asn Gly Gly Leu Thr Ile Glu Ala Met Val Arg Glu
        35                  40                  45

Leu Leu Arg Pro Met Leu Lys Glu Trp Leu Asp Glu Asn Leu Pro Ala
    50                  55                  60

Val Val Glu Arg Met Val Glu Lys Glu Ile Ala Arg Val Ala Arg Gly
65                  70                  75                  80


<210> SEQ ID NO 30
<211> LENGTH: 79
<212> TYPE: PRT
<213> ORGANISM: Pelagibacterium sp.

<400> SEQUENCE: 30

Asp Met Ala Asn Glu Leu Leu Glu Pro Ala Thr Lys Ala Ala Val His
1               5                   10                  15

Ser Ala Phe Ala Lys Leu Gly Thr Pro Ser Lys Gln Thr Ser Asp Met
            20                  25                  30

Ala Leu Gly Ala Ser Gly Leu Thr Ile Glu Asn Met Ile Arg Glu Met
        35                  40                  45

Leu Arg Pro Met Leu Lys Asp Trp Leu Glu Glu Asn Leu Pro Ser Met
    50                  55                  60

Val Glu Arg Met Val Glu Lys Glu Ile Glu Arg Val Ser Arg Gly
65                  70                  75
```

<210> SEQ ID NO 31
<211> LENGTH: 68
<212> TYPE: PRT
<213> ORGANISM: Hirschia maritima

<400> SEQUENCE: 31

```
Glu Gly Leu Val Ala Ala Ala Thr Ala Asp Ala Thr Ala Gly Gln Leu
1               5                   10                  15

Gly Lys Leu Met Gly Ser Met Met Leu Ser Gln Gly Thr Thr Ile Glu
            20                  25                  30

Asp Leu Val Arg Glu Met Leu Lys Pro Met Leu Lys Glu Trp Leu Asp
        35                  40                  45

Gly Asn Leu Pro Gln Leu Val Glu Gln Glu Val Lys Lys Glu Leu Gln
    50                  55                  60

Arg Ile Ser Arg
65
```

<210> SEQ ID NO 32
<211> LENGTH: 68
<212> TYPE: PRT
<213> ORGANISM: Unknown
<220> FEATURE:
<223> OTHER INFORMATION: Description of Unknown:
Rhodospirillaceae bacterium sequence

<400> SEQUENCE: 32

```
Asp Asn Leu Ile Gly Asp Ser Pro Arg Ala Gln Ala Thr Thr Ser Leu
1               5                   10                  15

Ala Asn Leu Ser Thr Ala Ile Arg Glu His Arg Pro Gly Leu Thr Val
            20                  25                  30

Glu Gln Leu Ala Glu Glu Leu Leu Arg Pro Met Leu Arg Glu Trp Leu
        35                  40                  45

Asp Ala Asn Leu Pro Asp Met Val Glu Arg Leu Val Gln Lys Glu Ile
    50                  55                  60

Gln Arg Met Ala
65
```

<210> SEQ ID NO 33
<211> LENGTH: 83
<212> TYPE: PRT
<213> ORGANISM: Unknown
<220> FEATURE:
<223> OTHER INFORMATION: Description of Unknown:
Rhodospirillales bacterium 35-66-84 sequence

<400> SEQUENCE: 33

```
Glu Ala Leu Val Gly Ala Gly Val Ala Gly Ala Thr Ser Ser Ala Phe
1               5                   10                  15

Ala Arg Leu Asn Gln Ala Val Gln Asp Ser Val Pro Ala Pro Ala Ala
            20                  25                  30

Thr Asp Pro Gly Pro Arg Val Gly Gly Ser Gly Gln Ser Ile Glu Asp
        35                  40                  45

Leu Val Lys Glu Met Leu Arg Pro Met Leu Lys Glu Trp Leu Asp Thr
    50                  55                  60

Asn Leu Pro Pro Met Val Glu Arg Tyr Val Glu Arg Glu Ile Ala Arg
65                  70                  75                  80

Leu Thr Arg
```

<210> SEQ ID NO 34
<211> LENGTH: 74
<212> TYPE: PRT
<213> ORGANISM: Sphingomonas sp.

<400> SEQUENCE: 34

Glu Asp Ile Val Ser Ala Ala Val Ala Ser Ala Ser Arg Asn Ala Leu
1 5 10 15

Ala Ser Leu Ala Arg Leu Lys Val Arg Ala Glu Asp Asp Ala Pro Glu
20 25 30

Asn Ser Leu Glu Gly Leu Val Arg Asp Met Leu Arg Pro Met Leu Lys
35 40 45

Glu Trp Leu Asp Ala Asn Leu Pro Arg Ile Val Glu Ala Met Val Ala
50 55 60

Lys Glu Ile Ala Arg Ile Ser Gly Asp Arg
65 70

<210> SEQ ID NO 35
<211> LENGTH: 67
<212> TYPE: PRT
<213> ORGANISM: Starkeya sp.

<400> SEQUENCE: 35

Glu Arg Leu Val Ser Gly Ser Ala Ser Asn Ala Val Ser Ala Ala Phe
1 5 10 15

Gly Ser Leu Gln Arg Thr Val Thr Ser Asn Ser Arg Thr Val Asp Asp
20 25 30

Leu Val Thr Glu Ala Ile Arg Pro Met Leu Lys Ala Trp Leu Asp Glu
35 40 45

Asn Leu Pro Thr Leu Val Glu Arg Leu Val Arg Ala Glu Ile Glu Arg
50 55 60

Val Ala Arg
65

<210> SEQ ID NO 36
<211> LENGTH: 70
<212> TYPE: PRT
<213> ORGANISM: Robiginitomaculum sp.

<400> SEQUENCE: 36

Asp Glu Leu Leu Ser Ala Ala Ser Thr Ala Ala Ser Ala Gly Thr Leu
1 5 10 15

Gly Ala Leu Ala Ser Ser Met Lys Leu Ala Glu Thr Asp Gly Gln Thr
20 25 30

Ile Glu Gly Val Met Arg Glu Leu Leu Arg Pro Leu Leu Lys Asp Trp
35 40 45

Leu Asp Thr Asn Leu Pro Ala Ile Val Glu Ala Lys Val Glu Ala Ala
50 55 60

Ile Asp Lys Val Val Arg
65 70

<210> SEQ ID NO 37
<211> LENGTH: 68
<212> TYPE: PRT
<213> ORGANISM: Methylosinus trichosporium

<400> SEQUENCE: 37

Leu Val Ser Ala Asp Ala Ala Asn Ser Val Ala Ser His Phe Gln Ala
1 5 10 15

```
Leu Ala Ala Ser Ile Val Leu Ser Glu Ser Asp Leu Ile Glu Arg Tyr
            20                  25                  30

Ala Arg Asp Leu Leu Arg Pro Leu Leu Lys Gln Trp Leu Asp Asp Asn
        35                  40                  45

Leu Pro His Ile Val Glu Arg Leu Val Arg Val Glu Ile Glu Arg Val
    50                  55                  60

Ala Arg Gly Arg
65


<210> SEQ ID NO 38
<211> LENGTH: 70
<212> TYPE: PRT
<213> ORGANISM: Unknown
<220> FEATURE:
<223> OTHER INFORMATION: Description of Unknown:
      Tardibacter chloracetimidivorans sequence

<400> SEQUENCE: 38

Ile Val Ser Asp Ala Thr Ala Ser Ala Thr Ala Glu Arg Leu Lys Ala
1               5                   10                  15

Leu Ser Ser Ala Met Ala Gly Pro Glu Ser Gly Ser Val Thr Leu Glu
            20                  25                  30

Gly Leu Val Arg Glu Met Leu Arg Pro Met Leu Lys Asp Trp Leu Asp
        35                  40                  45

Arg Asn Leu Pro Asp Ile Val Asp Glu Val Val Ser Arg Glu Ile Ala
    50                  55                  60

Arg Leu Thr Gly Lys Gly
65                  70


<210> SEQ ID NO 39
<211> LENGTH: 74
<212> TYPE: PRT
<213> ORGANISM: Microvirga sp.

<400> SEQUENCE: 39

Gln Thr Ala Glu Ala Leu Leu Ser Ser Glu Ala Val Ala Ser Val Thr
1               5                   10                  15

Gly Ala Phe Ser Arg Leu Ser Glu Ser Val Arg Pro Ala Gln Pro Gln
            20                  25                  30

Thr Val Glu Asp Leu Met Lys Glu Met Leu Arg Pro Met Leu Lys Ala
        35                  40                  45

Trp Leu Asp Asp Asn Leu Pro Pro Leu Val Glu Arg Leu Val Arg Glu
    50                  55                  60

Glu Ile Glu Arg Val Val Arg Arg Arg Ala
65                  70


<210> SEQ ID NO 40
<211> LENGTH: 74
<212> TYPE: PRT
<213> ORGANISM: Unknown
<220> FEATURE:
<223> OTHER INFORMATION: Description of Unknown:
      Rhodospirillaceae bacterium sequence

<400> SEQUENCE: 40

Leu Val Ser Ala Pro Val Ala Gln Gln Ala Ala Ser Thr Phe Ser Asn
1               5                   10                  15

Leu Ala Ser Thr Val Ser Gln Val Arg Gly Leu Pro Ile Gly Ser Pro
            20                  25                  30

Asn Arg Thr Leu Glu Asp Ile Val Lys Glu Leu Leu Arg Pro Met Leu
```

-continued

```
        35                  40                  45

Lys Asp Trp Leu Asp Ala Asn Leu Pro Thr Leu Val His Arg Ile Val
    50                  55                  60

Glu Arg Glu Val Ala Lys Leu Ala Gly Arg
65                  70


<210> SEQ ID NO 41
<211> LENGTH: 73
<212> TYPE: PRT
<213> ORGANISM: Unknown
<220> FEATURE:
<223> OTHER INFORMATION: Description of Unknown:
      Kordiimonadales bacterium JCM 17844 sequence

<400> SEQUENCE: 41

Glu Ala Leu Val Ser Ser Ser Thr Glu Glu Arg Ser Ser Ala Ser Phe
1               5                   10                  15

Ala Glu Leu Ser Ala Met Leu Val Gly Gly Tyr Glu Gly Ala Gly Asn
            20                  25                  30

Thr Leu Glu Gly Leu Val Arg Glu Met Leu Lys Pro Met Leu Arg Ala
        35                  40                  45

Trp Leu Asp Glu Asn Leu Pro Arg Ile Val Glu Asp Met Val Glu Arg
    50                  55                  60

Glu Val Ala Arg Ile Ala Ala Arg Gly
65                  70


<210> SEQ ID NO 42
<211> LENGTH: 75
<212> TYPE: PRT
<213> ORGANISM: Sphingobium sp.

<400> SEQUENCE: 42

Ala Glu Thr Met Leu Ser Val Glu Ser Glu Val Ala Thr Arg His Ser
1               5                   10                  15

Leu Ser Ala Leu Ser Ala Met Val Val Lys Pro Gln Glu Gly Gly Arg
            20                  25                  30

Asp Asn Thr Leu Glu Ser Leu Val Arg Glu Leu Leu Arg Pro Met Met
        35                  40                  45

Lys Asp Trp Leu Asp Ala His Leu Pro Asp Leu Val Glu Ala Met Val
    50                  55                  60

Ala Lys Glu Ile Ala Arg Ile Thr Gly Arg Ala
65                  70                  75


<210> SEQ ID NO 43
<211> LENGTH: 76
<212> TYPE: PRT
<213> ORGANISM: Microvirga sp.

<400> SEQUENCE: 43

Leu Leu Ser Pro Ala Val Asp Ser Thr Val Ser Gln Ala Phe Gly Leu
1               5                   10                  15

Leu Ser Ser Thr Ile Ser Asn Gln Ser Phe Ser Ser Thr Leu Leu Ser
            20                  25                  30

Ser Asn Pro Arg Thr Leu Glu Asp Leu Val Gly Asp Leu Leu Arg Pro
        35                  40                  45

Leu Leu Lys Ala Trp Leu Asp Glu His Leu Pro Pro Leu Val Glu Arg
    50                  55                  60

Leu Val Arg Ser Glu Ile Glu Arg Val Ala Arg Gly
65                  70                  75
```

<210> SEQ ID NO 44
<211> LENGTH: 63
<212> TYPE: PRT
<213> ORGANISM: Sphingobium sp.

<400> SEQUENCE: 44

Ser Thr Gln Ala Ala Arg Glu Ser Leu Val Asn Leu Ser Arg Leu Leu
1 5 10 15

Ile Arg Pro Glu Asp Gly Pro Ala Gly Thr Leu Glu Asp Leu Val Arg
20 25 30

Glu Met Leu Arg Pro Met Leu Lys Asp Trp Leu Asp Ala His Leu Pro
35 40 45

Gly Leu Val Glu Thr Leu Val Lys Arg Glu Ile Asp Arg Ile Thr
50 55 60

<210> SEQ ID NO 45
<211> LENGTH: 71
<212> TYPE: PRT
<213> ORGANISM: Unknown
<220> FEATURE:
<223> OTHER INFORMATION: Description of Unknown:
Alphaproteobacteria bacterium sequence

<400> SEQUENCE: 45

Ala Asp Ser Ile Ile Ser Thr Ser Thr Ala Ala Ala Gly Ile Ser Ser
1 5 10 15

Phe Gly Gln Leu Ala Arg Ser Val Lys Ser Gly Arg Pro Gly Ile Thr
20 25 30

Val Glu Gln Leu Ala Glu Glu Leu Met Arg Pro Met Leu Arg Gln Trp
35 40 45

Leu Asp Glu Asn Leu Pro Asp Met Val Glu Arg Leu Val Arg Arg Glu
50 55 60

Ile Glu Arg Met Ala Arg Ala
65 70

<210> SEQ ID NO 46
<211> LENGTH: 68
<212> TYPE: PRT
<213> ORGANISM: Hoeflea marina

<400> SEQUENCE: 46

Gln Leu Ile Ser Met Asp Ala Gly Ala Lys Val Ala Ala Ser Phe Asp
1 5 10 15

His Leu Ser Ala Thr Leu Ala Ala Ser Ser Thr Arg Ser Phe Asp Glu
20 25 30

Ile Ala Glu Glu Leu Leu Lys Pro Met Leu Gln Asn Trp Leu Asp Asp
35 40 45

Asn Leu Pro Thr Leu Val Glu Arg Leu Val Arg Glu Glu Ile Glu Arg
50 55 60

Val Ser Arg Gly
65

<210> SEQ ID NO 47
<211> LENGTH: 76
<212> TYPE: PRT
<213> ORGANISM: Micavibrio sp.

<400> SEQUENCE: 47

Glu Asp Asp Glu Asn Leu Leu Ser Glu Asn Thr Ala Ser Ala Ser Leu

```
1               5                   10                  15

Ala Ala Leu Asp Lys Leu Ser Arg Ser Ser Ala Ile Asp Asn Arg Arg
            20                  25                  30

Asn Ile Asn Asp Ala Val Thr Ile Glu Asp Ile Thr Arg Glu Met Leu
        35                  40                  45

Arg Pro Met Leu Lys Ala Trp Leu Asp Lys Asn Leu Pro Asp Ile Ile
    50                  55                  60

Glu Arg Thr Val Gln Lys Glu Ile Arg Arg Leu Ser
65                  70                  75


<210> SEQ ID NO 48
<211> LENGTH: 69
<212> TYPE: PRT
<213> ORGANISM: Unknown
<220> FEATURE:
<223> OTHER INFORMATION: Description of Unknown:
      Lichenihabitans psoromatis sequence

<400> SEQUENCE: 48

Glu Thr Leu Val Ser Pro Glu Ala Gly Ala Thr Val Gly Ser Ala Phe
1               5                   10                  15

Gln Thr Leu Ala Thr Ser Val Val Leu Gln Asn Ser Asp Thr Ile Glu
            20                  25                  30

Lys Leu Thr Arg Glu Met Leu Arg Pro Leu Leu Lys Ser Trp Leu Asp
        35                  40                  45

Asp His Leu Pro Ala Leu Val Glu Arg Leu Val Arg Gln Glu Ile Glu
    50                  55                  60

Arg Leu Ala Arg Gly
65


<210> SEQ ID NO 49
<211> LENGTH: 69
<212> TYPE: PRT
<213> ORGANISM: Unknown
<220> FEATURE:
<223> OTHER INFORMATION: Description of Unknown:
      Rhizobiales bacterium sequence

<400> SEQUENCE: 49

Asp His Leu Leu Ser Asn Gln Ala Ala Glu Ser Ile Ser Gly Ala Phe
1               5                   10                  15

Ser Asn Leu Ser Asn Leu Val Val Ser Gly Gln Ala Lys Thr Met Glu
            20                  25                  30

Asp Leu Met Arg Glu Met Leu Arg Pro Met Leu Gln Ala Trp Leu Asp
        35                  40                  45

Gln Asn Leu Pro Pro Met Val Glu Lys Met Val Ala Ser Glu Ile Arg
    50                  55                  60

Arg Leu Ser Gly Arg
65


<210> SEQ ID NO 50
<211> LENGTH: 72
<212> TYPE: PRT
<213> ORGANISM: Unknown
<220> FEATURE:
<223> OTHER INFORMATION: Description of Unknown:
      Alphaproteobacteria bacterium sequence

<400> SEQUENCE: 50

Ile Val Asp Lys Val Thr Ala Gln Ala Thr Ala Ala Ala Leu Asn Gln
1               5                   10                  15
```

```
Leu Val Val Asp Met Pro Ser Tyr Val Gly Met Gly Gln Gly Leu Ser
            20                  25                  30

Leu Glu Glu Ile Val Lys Glu Leu Leu Arg Pro Leu Leu Lys Glu Trp
        35                  40                  45

Leu Asp Gln His Leu Pro Gly Met Ala Glu Arg Leu Val Gln Glu Glu
    50                  55                  60

Ile Ser Arg Ile Ser Arg Ala Arg
65                  70


<210> SEQ ID NO 51
<211> LENGTH: 70
<212> TYPE: PRT
<213> ORGANISM: Devosia psychrophila

<400> SEQUENCE: 51

Asp Met Ala Asp Gln Leu Leu Glu Pro Ala Thr Gln Ala Ala Val Arg
1               5                   10                  15

Ser Ser Ile Thr Arg Leu Asn Gly Leu Gly Asn Thr Gly Ala Thr Ile
            20                  25                  30

Glu Ser Leu Met Arg Asp Met Leu Arg Pro Met Leu Lys Glu Trp Leu
        35                  40                  45

Asp Glu Asn Leu Pro Ser Val Val Glu Arg Met Val Glu Lys Glu Ile
    50                  55                  60

Ala Arg Val Ser Arg Gly
65                  70


<210> SEQ ID NO 52
<211> LENGTH: 73
<212> TYPE: PRT
<213> ORGANISM: Unknown
<220> FEATURE:
<223> OTHER INFORMATION: Description of Unknown:
      Aestuariivirga litoralis sequence

<400> SEQUENCE: 52

Ala Glu Gln Pro Ala Ile Leu Ser Gly Asn Ser Ala Gln Ala Val Gln
1               5                   10                  15

Ser Ala Phe Gly Lys Leu Ala Asp Ser Val Leu Ser Arg Ala Thr Asn
            20                  25                  30

Glu Arg Ser Val Glu Glu Val Thr Arg Glu Leu Leu Arg Val Met Leu
        35                  40                  45

Lys Gln Trp Leu Asp Glu Asn Leu Pro Ala Met Val Glu Arg Met Val
    50                  55                  60

Arg Glu Glu Ile Glu Arg Val Ala Arg
65                  70


<210> SEQ ID NO 53
<211> LENGTH: 68
<212> TYPE: PRT
<213> ORGANISM: Roseibium sp.

<400> SEQUENCE: 53

Leu Ile Ser Asn Asp Thr Gly Ala Ala Val His Thr Ala Leu Asp His
1               5                   10                  15

Leu Ser Ala Met Phe Val Gly Ser Lys Ala Gln Thr Val Glu Glu Leu
            20                  25                  30

Ile Gln Glu Met Leu Arg Pro Met Leu Lys Ala Trp Leu Asp Gln His
        35                  40                  45
```

```
Leu Pro Gly Met Val Glu Glu Met Val Gln Lys Glu Ile Lys Arg Ile
    50                  55                  60

Thr Arg Gly Arg
65


<210> SEQ ID NO 54
<211> LENGTH: 73
<212> TYPE: PRT
<213> ORGANISM: Devosia sp.

<400> SEQUENCE: 54

Asp Met Ala Glu Gln Leu Leu Ala Pro Ala Thr Asp Ala Ala Val Gln
1               5                   10                  15

Gly Ala Met Ser Arg Leu Gly Ser Leu Ala Gly Thr Gly Ile Gly Ser
            20                  25                  30

Met Thr Val Glu Ala Met Ile Arg Asp Met Leu Arg Pro Met Leu Lys
        35                  40                  45

Asp Trp Leu Asp Glu Asn Leu Pro Ala Leu Val Glu Arg Met Val Glu
    50                  55                  60

Lys Glu Ile Ser Arg Ile Ser Arg Gly
65                  70


<210> SEQ ID NO 55
<211> LENGTH: 76
<212> TYPE: PRT
<213> ORGANISM: Sphingobium sp.

<400> SEQUENCE: 55

Gln Leu Gln Asp Asn Ile Val Ser Ala Gln Ser Glu Asn Ala Ala Arg
1               5                   10                  15

Ser Ser Leu Ala Ala Leu Ser Asn Met Met Val Lys Ser Ala Gly Gln
            20                  25                  30

Gly Asp Pro Ala Thr Leu Glu Asp Leu Val Lys Asp Met Leu Arg Pro
        35                  40                  45

Met Leu Lys Glu Trp Leu Asp Ala Asn Leu Pro Asn Met Val Glu Gly
    50                  55                  60

Met Val Ala Lys Glu Ile Ser Arg Ile Thr Gly Arg
65                  70                  75


<210> SEQ ID NO 56
<211> LENGTH: 72
<212> TYPE: PRT
<213> ORGANISM: Labrenzia sp.

<400> SEQUENCE: 56

Glu Asp Asp Asp Pro Leu Thr Ser Asp Gln Thr Gly Glu Ala Val Asn
1               5                   10                  15

Ala Ala Phe Ser Asn Leu Ala Ser Leu Tyr Val Gly Asn Ala Gln Thr
            20                  25                  30

Val Glu Asp Leu Ile Lys Asp Met Leu Arg Pro Met Leu Lys Ala Trp
        35                  40                  45

Leu Asp Gln Asn Leu Pro Val Leu Val Glu Gln Leu Val Gln Lys Glu
    50                  55                  60

Ile Glu Arg Val Thr Arg Arg Arg
65                  70


<210> SEQ ID NO 57
<211> LENGTH: 73
<212> TYPE: PRT
```

<213> ORGANISM: Unknown
<220> FEATURE:
<223> OTHER INFORMATION: Description of Unknown:
Emcibacter congregatus sequence

<400> SEQUENCE: 57

Glu Val Leu Met Ser Ala Asn Ser Ser Gly Leu Ala Met Asp Gln Phe
1 5 10 15

Gly Ile Leu Ser Asp Leu Leu Thr Ser Gly Tyr Gln Gly Ser Gly Asn
20 25 30

Thr Leu Glu Asp Leu Val Arg Glu Met Leu Lys Pro Met Leu Arg Gly
35 40 45

Trp Leu Asp Glu Asn Leu Pro Pro Leu Val Glu Arg Met Val Ala Lys
50 55 60

Glu Ile Ala Arg Leu Ser Arg Thr Lys
65 70

<210> SEQ ID NO 58
<211> LENGTH: 72
<212> TYPE: PRT
<213> ORGANISM: Unknown
<220> FEATURE:
<223> OTHER INFORMATION: Description of Unknown:
Jiella endophytica sequence

<400> SEQUENCE: 58

Lys Phe Ala His Ala Leu Ile Ser Arg Glu Ala Gly Glu Arg Val Ala
1 5 10 15

Ala Ser Phe Ser Glu Leu Ala Ala Ala Ile Arg Asp Asp His Leu Arg
20 25 30

Asp Ser Asp Ala Ile Val Arg Glu Val Met Arg Pro Met Leu Gln Glu
35 40 45

Trp Leu Asp Glu Asn Leu Pro Arg Leu Val Glu Gln Leu Val Arg Glu
50 55 60

Glu Ile Glu Arg Ile Ala Arg Gly
65 70

<210> SEQ ID NO 59
<211> LENGTH: 68
<212> TYPE: PRT
<213> ORGANISM: Unknown
<220> FEATURE:
<223> OTHER INFORMATION: Description of Unknown:
Rhodospirillaceae bacterium sequence

<400> SEQUENCE: 59

Ile Val Ser Asp Pro Thr Ala Gln Ala Gly Val Asp Ala Phe Gly Gln
1 5 10 15

Leu Ala Gly Ile Ile Ala Gly Arg Met Gln Leu Gly Gln Gly Arg Thr
20 25 30

Val Glu Glu Leu Val Gln Glu Leu Leu Arg Pro Leu Leu Arg Glu Trp
35 40 45

Leu Asp Lys Asn Leu Pro Glu Leu Val Asp Glu Leu Val Lys Lys Glu
50 55 60

Ile Glu Arg Met
65

<210> SEQ ID NO 60
<211> LENGTH: 75
<212> TYPE: PRT
<213> ORGANISM: Unknown

<220> FEATURE:
<223> OTHER INFORMATION: Description of Unknown:
Alphaproteobacteria bacterium sequence

<400> SEQUENCE: 60

Glu Ile Glu Glu Gly Leu Leu Ser Ala Asp Ala Ala Val Ala Thr Ser
1 5 10 15

Ala Ala Phe Gly Asp Leu Asn Arg Thr Leu Thr Val Ser Leu Gly Glu
20 25 30

Gly Lys Thr Val Glu Ala Ile Val Gly Asp Leu Leu Arg Pro Leu Leu
35 40 45

Lys Ser Trp Leu Asp Gln His Leu Pro Pro Leu Val Glu Gln Met Val
50 55 60

Gln Glu Glu Ile Glu Arg Leu Ala Arg Arg Arg
65 70 75

<210> SEQ ID NO 61
<211> LENGTH: 68
<212> TYPE: PRT
<213> ORGANISM: Pseudochrobactrum asaccharolyticum

<400> SEQUENCE: 61

Leu Ile Ser Gln Ala Ala Glu Lys Gln Val Ala Ala Ser Phe Gly Ser
1 5 10 15

Leu Ser Gln Ala Leu Leu Glu Glu Gln Lys Arg Leu Leu Asn Asp Lys
20 25 30

Met Glu Ala Met Leu Arg Pro Met Leu Gln Glu Trp Leu Asp Thr Asn
35 40 45

Leu Pro Pro Leu Val Glu Arg Leu Val Arg Glu Glu Ile Glu Arg Val
50 55 60

Val Arg Arg Gly
65

<210> SEQ ID NO 62
<211> LENGTH: 76
<212> TYPE: PRT
<213> ORGANISM: Rhizobium sp.

<400> SEQUENCE: 62

Ala Glu Ala Leu Ser Gly Leu Asn Ala Leu Val Ser Ala Ala Thr Val
1 5 10 15

Glu Gln Val Ser Arg Ser Phe Gly Glu Leu Ala Ala Ala Ile Asp Gly
20 25 30

Gln Gln Arg Arg Ser Leu Asp Glu Met Ala Glu Asp Met Leu Arg Pro
35 40 45

Met Leu Arg Glu Trp Leu Asp Asp Asn Leu Pro Thr Leu Val Glu Arg
50 55 60

Leu Val Arg Glu Glu Ile Glu Arg Val Ala Arg Gly
65 70 75

<210> SEQ ID NO 63
<211> LENGTH: 69
<212> TYPE: PRT
<213> ORGANISM: Beijerinckia sp.

<400> SEQUENCE: 63

Gln Pro Leu Leu Ser Ala Glu Thr Asn Ala Ser Val Ala Thr Ala Phe
1 5 10 15

Gln Ser Leu Ala Gln Ser Val Leu Leu Arg Asp Pro Gly Val Met Glu

```
            20                  25                  30

Asn Met Ala Arg Asp Leu Leu Arg Pro Met Leu Lys Gln Trp Leu Asp
        35                  40                  45

Asp Asn Leu Pro Pro Leu Val Glu Arg Leu Val Arg Ala Glu Ile Glu
    50                  55                  60

Arg Ala Ala Arg Gly
65


<210> SEQ ID NO 64
<211> LENGTH: 79
<212> TYPE: PRT
<213> ORGANISM: Oceanibaculum indicum

<400> SEQUENCE: 64

Glu Glu Asp Glu Gly Leu Val Ser Pro Pro Lys Arg Asp Glu Ala Val
1               5                   10                  15

Ser Ala Phe Ala Asn Leu Thr Ser Thr Leu Glu Ala Arg His Pro Glu
            20                  25                  30

Leu Pro Ile Gly Ala Gly His Lys Thr Leu Glu Ser Leu Thr Lys Glu
        35                  40                  45

Val Met Arg Pro Met Leu Lys Asp Trp Leu Asp Lys Asn Leu Pro His
    50                  55                  60

Ile Val Glu Arg Leu Val Arg Glu Glu Ile Glu Arg Ile Ala Arg
65                  70                  75


<210> SEQ ID NO 65
<211> LENGTH: 70
<212> TYPE: PRT
<213> ORGANISM: Roseibium denhamense

<400> SEQUENCE: 65

Glu Phe Leu Thr Ser Ala Ala Thr Gly Gln Ala Val His Ala Ala Leu
1               5                   10                  15

Asp Asn Phe Ser Asp Met Leu Ile Ser Thr Lys Ala Gln Thr Ile Glu
            20                  25                  30

Glu Met Val Arg Glu Met Leu Arg Pro Met Ile Lys Ala Trp Leu Asp
        35                  40                  45

Lys Asn Leu Pro Pro Met Val Glu Glu Met Val Lys Lys Glu Ile Gln
    50                  55                  60

Arg Val Ile Arg Arg Arg
65                  70


<210> SEQ ID NO 66
<211> LENGTH: 75
<212> TYPE: PRT
<213> ORGANISM: Unknown
<220> FEATURE:
<223> OTHER INFORMATION: Description of Unknown:
      Alphaproteobacteria bacterium sequence

<400> SEQUENCE: 66

Asp Arg Leu Val Ser Asp Phe Ala Ala Asn Met Ala Ser Ser Arg Phe
1               5                   10                  15

Ser Ala Leu Ala Arg Ala Ala Glu Pro Asp Pro Leu Glu Gly Val Gln
            20                  25                  30

Arg Thr Gly Arg Thr Val Glu Glu Ile Ala Val Asp Leu Leu Arg Pro
        35                  40                  45

Met Leu Lys Glu Trp Leu Asp Thr Asn Val Pro Ser Ile Val Glu Arg
    50                  55                  60
```

Met Val Glu Arg Glu Ile Arg Tyr Leu Ser Arg
65 70 75

<210> SEQ ID NO 67
<211> LENGTH: 79
<212> TYPE: PRT
<213> ORGANISM: Azospirillum lipoferum

<400> SEQUENCE: 67

Glu Val Asp Asp Gly Leu Ile Ser Arg Arg Thr Ala Glu Asp Ala Ser
1 5 10 15

His His Leu Thr His Leu Ala Arg Glu Leu Gly Asp Asp Leu Ser Ile
20 25 30

Gly Pro Met Pro Ile Gly Ile Arg Thr Val Glu Glu Val Val Arg Glu
35 40 45

Leu Leu Lys Pro Leu Leu Lys Glu Trp Leu Asp Glu Asn Leu Pro Thr
50 55 60

Val Val Glu Arg Leu Val Gln Gln Glu Ile Asp Arg Met Ile Arg
65 70 75

<210> SEQ ID NO 68
<211> LENGTH: 74
<212> TYPE: PRT
<213> ORGANISM: Acuticoccus kandeliae

<400> SEQUENCE: 68

Glu Met Asp Asp Ser Leu Thr Ser Gln Lys Thr Arg Gln Ser Val Thr
1 5 10 15

Asn Ser Leu Asp Gln Leu Ser Arg Thr Ile Leu Ser Asn Asn Pro Arg
20 25 30

Thr Leu Glu Asp Leu Val Arg Asp Met Val Arg Pro Leu Leu Arg Glu
35 40 45

Trp Leu Glu Ala Asn Leu Pro Asp Ile Val Glu Arg Gln Val Arg Gln
50 55 60

Glu Ile Asp Arg Val Ala Ser Arg Gly Arg
65 70

<210> SEQ ID NO 69
<211> LENGTH: 68
<212> TYPE: PRT
<213> ORGANISM: Unknown
<220> FEATURE:
<223> OTHER INFORMATION: Description of Unknown: Alphaproteobacteria bacterium sequence

<400> SEQUENCE: 69

Leu Met Ser Asp Ser Ala Ala Gly Ala Ala Ala Ala Ser Phe Glu Asn
1 5 10 15

Leu Ala Arg Ala Met Pro Val Leu Glu Glu Asp Ser Arg Ser Leu Glu
20 25 30

Gly Ile Val Val Glu Met Leu Arg Pro Val Leu Ala Ala Trp Leu Asp
35 40 45

Gln His Leu Pro Lys Ile Val Glu Gln Met Val Gln Lys Glu Ile Glu
50 55 60

Arg Val Ser Arg
65

<210> SEQ ID NO 70
<211> LENGTH: 64

```
<212> TYPE: PRT
<213> ORGANISM: Sphingomonas sp.

<400> SEQUENCE: 70

Ile Ala Glu Pro Ala Ala Ser Ala His Ala Gly Pro Ser Leu Ser Ser
1               5                   10                  15

Leu Ile Ile Asn Pro Ala Gly Thr Gly Gln Thr Leu Glu Gly Leu Val
            20                  25                  30

Arg Asp Met Leu Arg Pro Met Leu Ser Asp Trp Ile Asp Thr Asn Leu
        35                  40                  45

Pro Gly Ile Val Glu Arg Leu Val Lys Gln Glu Met Ser Gly Ile Asn
    50                  55                  60


<210> SEQ ID NO 71
<211> LENGTH: 69
<212> TYPE: PRT
<213> ORGANISM: Methyloferula stellata

<400> SEQUENCE: 71

Glu Pro Ile Ala Ser Pro Ala Thr Asp Ala Ala Val Ala Ser Ser Phe
1               5                   10                  15

Asn Ala Leu Phe Ala Ser Arg Leu Leu Pro Asn Pro Glu Met Leu Ala
            20                  25                  30

Glu Leu Thr Arg Asp Leu Leu Arg Pro Met Leu Lys Ala Trp Leu Asp
        35                  40                  45

Asp Asn Leu Pro Val Met Val Glu Arg Leu Val Arg Ala Glu Ile Glu
    50                  55                  60

Arg Val Ala Arg Gly
65


<210> SEQ ID NO 72
<211> LENGTH: 79
<212> TYPE: PRT
<213> ORGANISM: Zavarzinia sp.

<400> SEQUENCE: 72

Glu Pro Leu Val Ser Thr Pro Ile Ala Asn Gln Ala Arg Asn Ala Phe
1               5                   10                  15

Ala Gln Val Ala Asp Ala Ala Arg Pro Ser Val Ser Pro Arg Glu Ser
            20                  25                  30

Val Gly Asp Gly Arg Thr Val Glu Gln Val Ala Glu Asp Leu Met Arg
        35                  40                  45

Pro Met Leu Lys Ala Trp Leu Asp Ala His Leu Pro Ala Ile Val Glu
    50                  55                  60

Arg Ala Val Ala Glu Glu Leu Ala Arg Ile Thr Gly Arg Gly Ser
65                  70                  75


<210> SEQ ID NO 73
<211> LENGTH: 81
<212> TYPE: PRT
<213> ORGANISM: Unknown
<220> FEATURE:
<223> OTHER INFORMATION: Description of Unknown:
      Alphaproteobacteria bacterium MarineAlpha10_Bin3 sequence

<400> SEQUENCE: 73

Glu Val Val Glu Asp Asp Val Leu Val Ser Ala Ala Thr Thr Ala Val
1               5                   10                  15

Gly Ala Ser Ala Phe Ala Gln Leu Thr Gly Ala Met Asp Leu Ala Met
            20                  25                  30
```

```
Arg Leu Gly Gly Val Asp Arg Thr Leu Glu Ala Leu Val Lys Glu Leu
        35                  40                  45

Met Arg Pro Met Leu Arg Asp Trp Leu Glu Ala Asn Leu Pro Ala Val
    50                  55                  60

Val Glu Arg Leu Val Gln Arg Glu Ile Asp Lys Met Ser Val Lys Ser
65                  70                  75                  80

Gly


<210> SEQ ID NO 74
<211> LENGTH: 76
<212> TYPE: PRT
<213> ORGANISM: Caulobacter vibrioides

<400> SEQUENCE: 74

Glu Val Ala Glu Gln Leu Val Gly Val Ser Ala Ala Ser Ala Ala Ala
1               5                   10                  15

Ser Ala Phe Gly Ser Leu Ser Ser Ala Leu Leu Met Pro Lys Asp Gly
            20                  25                  30

Arg Thr Leu Glu Asp Val Val Arg Glu Leu Leu Arg Pro Leu Leu Lys
        35                  40                  45

Glu Trp Leu Asp Gln Asn Leu Pro Arg Ile Val Glu Thr Lys Val Glu
    50                  55                  60

Glu Glu Val Gln Arg Ile Ser Arg Gly Arg Gly Ala
65                  70                  75


<210> SEQ ID NO 75
<211> LENGTH: 70
<212> TYPE: PRT
<213> ORGANISM: Asticcacaulis sp.

<400> SEQUENCE: 75

Ala Ser Arg Leu Val Ser Asp Arg Thr Glu Ser Thr Ala Ala Asn Ala
1               5                   10                  15

Phe Gly Ala Leu Thr Asn Ala Leu Leu Val Pro Lys Asp Gly Arg Thr
            20                  25                  30

Leu Glu Asp Val Leu Lys Glu Leu Met Arg Pro Met Leu Gln Asp Trp
        35                  40                  45

Leu Asp Lys Asn Leu Ala Ala Ile Val Glu Glu Gln Val Arg Leu Glu
    50                  55                  60

Val Glu Arg Ile Ala Arg
65                  70


<210> SEQ ID NO 76
<211> LENGTH: 72
<212> TYPE: PRT
<213> ORGANISM: Phenylobacterium sp.

<400> SEQUENCE: 76

Ala Ala Asn Leu Val Ser Asp His Ile Ala Ala Ala Ala Ala Ala Thr
1               5                   10                  15

Phe Gly Gln Leu Ser Ser Ser Ile Leu Met Pro Ala Glu Gly Arg Thr
            20                  25                  30

Leu Glu Asp Val Val Arg Glu Met Leu Arg Pro Met Leu Gln Gln Trp
        35                  40                  45

Leu Asp Thr Asn Leu Pro Gly Ile Val Gln Glu Ala Val Gln Ala Glu
    50                  55                  60

Val Glu Arg Ile Ala Arg Gly Arg
```

65 70

<210> SEQ ID NO 77
<211> LENGTH: 61
<212> TYPE: PRT
<213> ORGANISM: Brevundimonas sp.

<400> SEQUENCE: 77

Ala Ser Ala Phe Ala Gly Leu Thr Ala Ala Ala Arg Thr Pro Ala Asp
1 5 10 15

Ala Arg Ser Leu Glu Asp Ile Val Arg Glu Leu Leu Arg Pro Met Leu
20 25 30

Lys Asp Trp Leu Asp Ala Asn Leu Pro Gly Ile Val Glu Arg Glu Val
35 40 45

Arg Ala Glu Val Glu Arg Ile Ser Arg Gln Gly Gly Ala
50 55 60

<210> SEQ ID NO 78
<211> LENGTH: 72
<212> TYPE: PRT
<213> ORGANISM: Asticcacaulis excentricus

<400> SEQUENCE: 78

Glu Thr Thr Ser His Leu Val Ser Glu Arg Thr Val Gln Ser Ala Val
1 5 10 15

Ser Ala Phe Gly Gln Leu Thr Ser Ala Ser Leu Leu Pro Arg Glu Gly
20 25 30

Arg Ser Ile Glu Asp Leu Leu Thr Glu Ile Leu Arg Pro Met Leu Gln
35 40 45

Asp Trp Leu Asp Gly Asn Leu Pro Ala Ile Val Glu Thr Ala Val Arg
50 55 60

Glu Glu Val Glu Arg Leu Ala Arg
65 70

<210> SEQ ID NO 79
<211> LENGTH: 61
<212> TYPE: PRT
<213> ORGANISM: Unknown
<220> FEATURE:
<223> OTHER INFORMATION: Description of Unknown:
Hyphomonadaceae bacterium sequence

<400> SEQUENCE: 79

Ser Ala Gly Lys Ala Ala Gly Ala Leu Gly Gln Leu Met Gly Ser Met
1 5 10 15

Ala Ile Gly Asn Gly Ala Thr Leu Glu Ser Ile Val Arg Glu Leu Leu
20 25 30

Arg Pro Met Leu Lys Glu Trp Leu Asn Glu Asn Leu Pro Gly Ile Val
35 40 45

Glu Ala Lys Val Glu Glu Glu Val Lys Arg Ile Ser Arg
50 55 60

<210> SEQ ID NO 80
<211> LENGTH: 74
<212> TYPE: PRT
<213> ORGANISM: Maritalea myrionectae

<400> SEQUENCE: 80

Asp Ile Ala Asp Ser Leu Leu Glu Pro Thr Ala Gln Ala Ala Ser Ser
1 5 10 15

```
His Ala Phe Ser Gln Leu Asp Asn Leu Ile Met Ser Gln Lys Gln Gly
            20                  25                  30

Gln Thr Ile Glu Asp Leu Ile Arg Glu Met Leu Arg Pro Met Leu Lys
        35                  40                  45

Ser Trp Leu Asp Glu Asn Leu Pro Gly Val Val Glu Gln Leu Val Gln
    50                  55                  60

Arg Glu Ile Glu Arg Val Ser Arg Gly Lys
65                  70
```

```
<210> SEQ ID NO 81
<211> LENGTH: 73
<212> TYPE: PRT
<213> ORGANISM: Pleomorphomonas oryzae

<400> SEQUENCE: 81

Glu Met Asp Glu Pro Leu Val Ser Ala Ala Ala Ser Ala Thr Val Gln
1               5                   10                  15

Ser Ala Phe Gly Gln Leu Ser His Thr Val Leu Ala Ala Asn Gly Arg
            20                  25                  30

Thr Leu Asp Asp Leu Val Lys Glu Met Leu Arg Pro Met Leu His Ala
        35                  40                  45

Trp Leu Asp Glu Asn Leu Pro Val Ile Val Glu Arg Leu Val Arg Ala
    50                  55                  60

Glu Ile Glu Arg Val Ser Arg Gly Arg
65                  70
```

```
<210> SEQ ID NO 82
<211> LENGTH: 70
<212> TYPE: PRT
<213> ORGANISM: Rhodobium orientis

<400> SEQUENCE: 82

Glu Pro Leu Leu Ser Pro Thr Ser Asp Ala Ala Val Ser Ala Ala Phe
1               5                   10                  15

Gly Asn Leu Ala His Thr Ile Leu Ser Asn Asn Ala Arg Thr Leu Glu
            20                  25                  30

Asp Leu Val Gly Glu Met Leu Arg Pro Met Leu Lys Thr Trp Leu Asp
        35                  40                  45

Asp Asn Leu Pro Ala Leu Val Glu Arg Leu Val Arg Gln Glu Ile Glu
    50                  55                  60

Arg Val Ser Arg Gly Arg
65                  70
```

```
<210> SEQ ID NO 83
<211> LENGTH: 71
<212> TYPE: PRT
<213> ORGANISM: Microvirga sp.

<400> SEQUENCE: 83

Ala Glu Thr Leu Leu Ser Ser Ala Ala Asn Ala Ser Val Ser Asp Ala
1               5                   10                  15

Phe Thr Arg Leu Gly Ser Thr Ile Met Pro Thr Gln Pro Gln Thr Leu
            20                  25                  30

Glu Asp Leu Met Lys Asp Leu Leu Arg Pro Ile Leu Lys Ser Trp Leu
        35                  40                  45

Asp Glu Asn Leu Pro Ser Leu Val Glu Arg Leu Val Gln Ala Glu Ile
    50                  55                  60

Glu Arg Ile Ser Arg Gly Gln
```

```
65                  70


<210> SEQ ID NO 84
<211> LENGTH: 82
<212> TYPE: PRT
<213> ORGANISM: Sphingopyxis macrogoltabida

<400> SEQUENCE: 84

Glu Glu Leu Val Ser Ala Ala Ser Ala Asp Ala Ala Arg Gln Ser Leu
1               5                   10                  15

Glu Ala Leu Ser Ala Ala Val Thr Pro Asp Thr Ala Ala Thr Asn Ala
            20                  25                  30

His Val Ala Pro Val Pro Ala Ala Arg Thr Met Glu Asp Val Val Leu
        35                  40                  45

Asp Ala Leu Arg Pro Met Leu Lys Asp Trp Leu Asp Thr Asn Leu Pro
    50                  55                  60

Ser Leu Val Glu Ala Met Val Ala Lys Glu Ile Ser Arg Ile Thr Gly
65                  70                  75                  80

Lys Arg


<210> SEQ ID NO 85
<211> LENGTH: 71
<212> TYPE: PRT
<213> ORGANISM: Unknown
<220> FEATURE:
<223> OTHER INFORMATION: Description of Unknown:
      Sphingomonadaceae sequence

<400> SEQUENCE: 85

Ile Val Ser Thr Val Ala Val Glu Ala Ser Arg His Ala Leu Ala Ser
1               5                   10                  15

Leu Ser Lys Met Val Val Lys Pro Glu Val Ala Gly Ser Asp Thr Leu
            20                  25                  30

Glu Gly Val Val Arg Asp Met Leu Lys Pro Met Leu Lys Asp Trp Leu
        35                  40                  45

Asp Thr His Leu Pro Asp Ile Val Glu Arg Met Val Ala Gln Glu Val
    50                  55                  60

Ala Arg Ile Ser Gly Arg Ser
65                  70


<210> SEQ ID NO 86
<211> LENGTH: 77
<212> TYPE: PRT
<213> ORGANISM: Croceicoccus sp.

<400> SEQUENCE: 86

Ser Glu Ser Leu Ile Ala Gly Ala Ala Ala Ala Thr Leu Arg Asp Ser
1               5                   10                  15

Phe Ala Ala Leu Gln Ser Val Ala Ser Thr Pro Glu Pro Ser Lys Pro
            20                  25                  30

Ala Gly Thr Ala Asn Pro Leu Glu Asp Met Val Arg Glu Met Met Arg
        35                  40                  45

Pro Met Leu Lys Gln Trp Leu Asp Asp Asn Met Pro Gly Met Val Glu
    50                  55                  60

Lys Ile Val Glu Arg Glu Ile Ala Arg Ile Thr Gly Arg
65                  70                  75


<210> SEQ ID NO 87
<211> LENGTH: 68
```

```
<212> TYPE: PRT
<213> ORGANISM: Unknown
<220> FEATURE:
<223> OTHER INFORMATION: Description of Unknown:
      Rhizobiales bacterium sequence

<400> SEQUENCE: 87

Asn Leu Val Ser Ala Glu Ala Gly Ala Gln Ile Ala Arg Ser Phe Gly
1               5                   10                  15

Ala Leu Ala Glu Val Phe Asp Gly Val Arg Asn Pro Thr Ile Glu Thr
            20                  25                  30

Val Ala Gln Asp Met Leu Arg Pro Met Leu Gln Glu Trp Leu Glu Asp
        35                  40                  45

Asn Leu Pro Thr Ile Val Glu Arg Met Val Arg Glu Glu Ile Glu Arg
    50                  55                  60

Val Ala Arg Gly
65


<210> SEQ ID NO 88
<211> LENGTH: 81
<212> TYPE: PRT
<213> ORGANISM: Unknown
<220> FEATURE:
<223> OTHER INFORMATION: Description of Unknown:
      Alphaproteobacteria bacterium 41-28 sequence

<400> SEQUENCE: 88

Ser Glu Pro Leu Val Ser Ser Ala Ala Val Ser Glu Ala Ala Leu Ser
1               5                   10                  15

Phe Gln Ala Leu Asn Lys Val Ala Ser Glu Ser Pro Arg Tyr Pro Asp
            20                  25                  30

Pro Arg Leu Asn Ala Gly Ile Gly Gly Gln Thr Val Glu Asn Leu Val
        35                  40                  45

Arg Glu Ile Leu Arg Pro Leu Leu Lys Glu Trp Leu Asp Ala Asn Leu
    50                  55                  60

Pro Thr Leu Val Arg Trp Val Val Asn Glu Gln Val Glu Arg Ile Val
65                  70                  75                  80

Arg


<210> SEQ ID NO 89
<211> LENGTH: 73
<212> TYPE: PRT
<213> ORGANISM: Parvularcula sp.

<400> SEQUENCE: 89

Ala Gln Thr Leu Val Ser Asp Gly Ala Ala Lys Lys Val Ser Asp Ala
1               5                   10                  15

Phe Gly Ala Leu His Glu Asn Val Arg Val Ser Asn Ala Gly Gly Gln
            20                  25                  30

Thr Ile Glu Asp Ile Val Glu Ala Met Leu Arg Pro Met Ile Gln Gln
        35                  40                  45

Trp Leu Asp Gln Asn Leu Pro Arg Ile Val Glu Glu Lys Val Glu Glu
    50                  55                  60

Glu Val Arg Arg Ile Ala Arg Arg Arg
65                  70


<210> SEQ ID NO 90
<211> LENGTH: 71
<212> TYPE: PRT
<213> ORGANISM: Unknown
```

```
<220> FEATURE:
<223> OTHER INFORMATION: Description of Unknown:
      Alphaproteobacteria bacterium sequence

<400> SEQUENCE: 90

Leu Val Gly Asp Pro Ala Val Gln Ala Ala Gly Ala Ser Ile Ala Gln
1               5                   10                  15

Leu Ala Asn Ala Val Ser Arg Glu Arg Ala Val Val Leu Gly Asn Thr
            20                  25                  30

Gly Ile Thr Leu Glu Gln Leu Val Arg Glu Ile Cys Thr Pro Ile Leu
        35                  40                  45

Lys Glu Trp Leu Asp Thr Asn Leu Pro His Ile Val Asp Arg Val Val
    50                  55                  60

Lys Gln Glu Ile Glu Arg Ile
65                  70


<210> SEQ ID NO 91
<211> LENGTH: 70
<212> TYPE: PRT
<213> ORGANISM: Stakelama pacifica

<400> SEQUENCE: 91

Glu Thr Ile Val Ser Arg Gln Ala Ala Asp Ala Ser Arg Gly Lys Leu
1               5                   10                  15

Glu Ser Leu Ser Arg Met Val Val Lys Pro Glu Thr Pro Gly Ser Asp
            20                  25                  30

Thr Leu Glu Gly Met Val Arg Glu Met Leu Arg Pro Met Leu Arg Glu
        35                  40                  45

Trp Met Asp Ala Asn Leu Pro Gly Leu Val Glu Arg Met Val Gln Arg
    50                  55                  60

Glu Ile Glu Arg Ile Thr
65                  70


<210> SEQ ID NO 92
<211> LENGTH: 70
<212> TYPE: PRT
<213> ORGANISM: Unknown
<220> FEATURE:
<223> OTHER INFORMATION: Description of Unknown:
      Rhizobiales bacterium sequence

<400> SEQUENCE: 92

Glu Gly Leu Leu Ser Asp Arg Ala Gly Ala Ser Val Gly His Ala Phe
1               5                   10                  15

Asp Ala Leu Ser Arg Thr Val Ser Ala Gln Thr Pro Arg Ser Val Glu
            20                  25                  30

Glu Leu Val Ala Asp Ile Leu Arg Pro Met Leu Lys Ser Trp Leu Asp
        35                  40                  45

Gln Asn Leu Pro Gly Leu Val Glu Asp Leu Val Arg Gln Glu Ile Glu
    50                  55                  60

Arg Ile Ala Arg Ser Arg
65                  70


<210> SEQ ID NO 93
<211> LENGTH: 70
<212> TYPE: PRT
<213> ORGANISM: Unknown
<220> FEATURE:
<223> OTHER INFORMATION: Description of Unknown:
      Alphaproteobacteria bacterium sequence
```

<400> SEQUENCE: 93

```
Val Ser Asp Glu Val Glu Glu Val Ser Ala Ala Ser Met Ser Gly Leu
1               5                   10                  15

Thr Ala Ala Leu Ala Ala Thr Ala Ala Val Gly Asp Gly Asn Lys Thr
            20                  25                  30

Leu Glu Glu Leu Val Lys Glu Val Leu Arg Pro Ile Leu Lys Glu Trp
        35                  40                  45

Leu Asp Asp Asn Leu Pro Asp Val Val Asp Arg Ile Val His Glu Glu
    50                  55                  60

Val Glu Arg Ile Ser Gln
65                  70
```

<210> SEQ ID NO 94
<211> LENGTH: 70
<212> TYPE: PRT
<213> ORGANISM: Micavibrio sp.

<400> SEQUENCE: 94

```
Ile Leu Ser Asp Ser Ala Gln Ser Ala Thr Met Ser Ser Leu Ser Lys
1               5                   10                  15

Leu Val Gly Asn Val Pro Leu Asn Arg Arg Gly Tyr Asp Gly Ile Thr
            20                  25                  30

Leu Glu Asp Ile Val Arg Glu Leu Leu Asn Pro Met Leu Arg Asp Trp
        35                  40                  45

Met Asp Asp Asn Leu Pro Pro Met Val Glu Arg Ile Val Gln Lys Glu
    50                  55                  60

Leu Glu Lys Leu Ala Arg
65                  70
```

<210> SEQ ID NO 95
<211> LENGTH: 83
<212> TYPE: PRT
<213> ORGANISM: Unknown
<220> FEATURE:
<223> OTHER INFORMATION: Description of Unknown:
      Alphaproteobacteria bacterium MarineAlpha3_Bin2 sequence

<400> SEQUENCE: 95

```
Val Thr Ser Glu Ile Val Ser Ala Ser Thr Ala His Ala Ala Thr Asp
1               5                   10                  15

Ile Leu Ser Glu Leu Ala Lys Ala Ile Leu Asn Arg Arg Asp Val Ala
            20                  25                  30

Val Asp Asp Ala Gly Gln Asn Met Thr Leu Glu Gly Met Val Arg Glu
        35                  40                  45

Ile Leu Lys Pro Leu Leu Arg Glu Trp Leu Asp Arg Asn Leu Pro Tyr
    50                  55                  60

Leu Ile Glu Arg Leu Val Lys Lys Glu Ile Asp Thr Met Ile Asn Arg
65                  70                  75                  80

Ala Glu Gly
```

<210> SEQ ID NO 96
<211> LENGTH: 79
<212> TYPE: PRT
<213> ORGANISM: Unknown
<220> FEATURE:
<223> OTHER INFORMATION: Description of Unknown:
      Elstera cyanobacteriorum sequence

<400> SEQUENCE: 96

-continued

```
Asp Ala Leu Met Ser Pro Asp Thr Ala Ser Ala Ala Ser Arg Ala Phe
1               5                   10                  15

Ala Lys Leu Gln Asp Met Asp Glu Asp Glu Ser Pro Ala Ala Ala Val
            20                  25                  30

Met Arg Ala Ser Gly Gly Gly Asn Pro Thr Leu Asp Glu Leu Val Arg
        35                  40                  45

Glu Ala Leu Lys Pro Val Leu Arg Glu Trp Leu Asp Arg Asn Leu Pro
    50                  55                  60

Pro Met Val Glu Thr Met Val Arg Glu Glu Ile Gln Arg Leu Ala
65                  70                  75


<210> SEQ ID NO 97
<211> LENGTH: 73
<212> TYPE: PRT
<213> ORGANISM: Unknown
<220> FEATURE:
<223> OTHER INFORMATION: Description of Unknown:
      OCS116 cluster bacterium sequence

<400> SEQUENCE: 97

Ile Ser Asp Ser Leu Ile Ser Glu Gln Val Gly Asp Ala Val Asn Lys
1               5                   10                  15

Asn Phe His Leu Leu Ala Asn Thr Leu Leu Ala Gln Asn Gly Ala Gly
            20                  25                  30

Gln Thr Val Glu Ser Met Val Met Ala Leu Met Arg Pro Met Leu Lys
        35                  40                  45

Ser Trp Leu Asp Glu Asn Leu Pro Val Met Val Glu Lys Ile Val Arg
    50                  55                  60

Glu Glu Ile Glu Arg Val Ala Arg Gly
65                  70


<210> SEQ ID NO 98
<211> LENGTH: 76
<212> TYPE: PRT
<213> ORGANISM: Sphingomonas sp.

<400> SEQUENCE: 98

Glu Glu Ala Pro Ala Val Ser Pro Ala Thr Val Glu Ala Thr Arg Gly
1               5                   10                  15

Ala Leu Gly Ala Leu Ser Arg Leu Ile Val Lys Pro Glu Pro Glu Ser
            20                  25                  30

Asp Gly Thr Leu Glu Gly Leu Val Arg Glu Met Leu Arg Pro Met Leu
        35                  40                  45

Ser Glu Trp Leu Asp His Asn Leu Pro Pro Leu Val Glu Gln Met Val
    50                  55                  60

Ala Arg Glu Ile Ala Lys Ile Ile Ala Asn Gln Gly
65                  70                  75


<210> SEQ ID NO 99
<211> LENGTH: 76
<212> TYPE: PRT
<213> ORGANISM: Insolitispirillum peregrinum

<400> SEQUENCE: 99

Asp Arg Leu Val Ser Pro Pro Thr Glu Val Ala Ser Ala Ala Ile Phe
1               5                   10                  15

Ser Glu Leu Tyr Gly Ala Leu Ala Arg Asp Arg Gly Leu Gly Ile Gly
            20                  25                  30

Lys Val Gly Ile Thr Leu Glu Glu Ile Val Arg Glu Ala Leu Arg Pro
```

```
        35                  40                  45

Leu Leu Arg Glu Trp Leu Asp Ala Asn Leu Pro Glu Leu Val Glu Arg
    50                  55                  60

Leu Val Arg Lys Glu Ile Glu Arg Leu Val Thr Gly
65                  70                  75


<210> SEQ ID NO 100
<211> LENGTH: 79
<212> TYPE: PRT
<213> ORGANISM: Unknown
<220> FEATURE:
<223> OTHER INFORMATION: Description of Unknown:
      Rhodospirillaceae bacterium sequence

<400> SEQUENCE: 100

Glu Pro Leu Met Glu Val Ser Ser Glu Asp Val Ala Val Ser Ala Phe
1               5                   10                  15

Ala Ala Leu Ala Ser Gln Val Ser Ser Gly Ser Ala Glu His Arg Ala
            20                  25                  30

Gln Ala Ile Ser Pro Ser Glu Arg Thr Leu Glu Asp His Val Leu Glu
        35                  40                  45

Met Leu Arg Pro Met Leu Arg Glu Trp Leu Asp Lys His Leu Pro Glu
    50                  55                  60

Met Val Gln Arg Leu Val Gln Arg Glu Ile Asp Arg Ile Thr His
65                  70                  75


<210> SEQ ID NO 101
<211> LENGTH: 67
<212> TYPE: PRT
<213> ORGANISM: Unknown
<220> FEATURE:
<223> OTHER INFORMATION: Description of Unknown:
      Aestuariispira insulae sequence

<400> SEQUENCE: 101

Val Ser Gln Ala Thr Asp Ala Leu Gly Thr Ala Ser Phe Ala Tyr Leu
1               5                   10                  15

Glu Lys Ser Ile Arg Met Gly Gln Val Gly Asp Thr Leu Glu Asp Ile
            20                  25                  30

Val Lys Gly Leu Leu Arg Pro Met Leu Gln Ser Trp Leu Asp Glu Asn
        35                  40                  45

Leu Pro Gln Leu Val Glu Arg Leu Val Gln Arg Glu Ile Glu Met Met
    50                  55                  60

Ala Gly Gly
65


<210> SEQ ID NO 102
<211> LENGTH: 74
<212> TYPE: PRT
<213> ORGANISM: Micavibrio sp.

<400> SEQUENCE: 102

Glu Ser Val Leu Gly Glu Val Ala Ala Ser Ala Thr Phe Ala Gly Phe
1               5                   10                  15

Ala Arg Leu Ala Asn Asn Ile Ala Val Asp Arg Arg Arg Gln Thr Gly
            20                  25                  30

Glu Gly Val Thr Ile Glu Asp Ile Val Arg Asp Met Leu Gln Pro Leu
        35                  40                  45

Leu Arg Gln Trp Leu Asp Asp Asn Leu Pro Thr Met Ile Glu Arg Met
    50                  55                  60
```

Val Gln Lys Glu Leu Glu Lys Leu Ala Gln
65 70

<210> SEQ ID NO 103
<211> LENGTH: 74
<212> TYPE: PRT
<213> ORGANISM: Sphingosinicella microcystinivorans

<400> SEQUENCE: 103

Glu Glu Ala Gln Ser Ala Val Ser Asp Asp Ile Met Ala Lys Ala Ser
1 5 10 15

Glu Ser Phe Ser Ala Leu Ser Ser Leu Arg Leu Arg Gly Asp Gly Ala
20 25 30

Gly Pro Glu Thr Leu Glu Gly Leu Val Arg Glu Met Leu Gln Pro Met
35 40 45

Leu Lys Ser Trp Leu Asp Ala Asn Leu Pro Glu Ile Val Glu Gln Met
50 55 60

Val Ala Arg Glu Ile Ala Arg Ile Thr Arg
65 70

<210> SEQ ID NO 104
<211> LENGTH: 71
<212> TYPE: PRT
<213> ORGANISM: Micavibrio sp.

<400> SEQUENCE: 104

Val Arg Glu Glu Leu Ile Ser Ala Thr Thr Ala Ser Ala Ser Leu Glu
1 5 10 15

Ala Met Ser Lys Leu Val Ala Glu Glu Val Ala Arg Pro Asp Ser Ser
20 25 30

Ser Thr Ile Glu Gln Ile Thr Lys Asp Leu Leu Arg Pro Met Leu Lys
35 40 45

Asp Trp Leu Asp Ala Asn Leu Pro Ala Leu Ile Glu Lys Leu Val Gln
50 55 60

Lys Glu Leu Arg Arg Leu Ser
65 70

<210> SEQ ID NO 105
<211> LENGTH: 75
<212> TYPE: PRT
<213> ORGANISM: Sphingosinicella sp.

<400> SEQUENCE: 105

Val Thr Glu Glu Ala Gly Leu Leu Ser Ser Gly Ala Ala Ala Ala Ser
1 5 10 15

Arg Glu Arg Leu Ala Ala Leu Ser Ala Leu Arg Gln Arg Thr Glu Ile
20 25 30

Pro Thr Asp Thr Gly Ala Leu Glu Ala Val Val Arg Asp Met Leu Arg
35 40 45

Pro Met Leu Lys Asp Trp Leu Asp Glu His Leu Pro Ala Ile Val Glu
50 55 60

Gln Leu Val Thr Arg Glu Ile Ala Arg Ile Thr
65 70 75

<210> SEQ ID NO 106
<211> LENGTH: 74
<212> TYPE: PRT
<213> ORGANISM: Unknown
<220> FEATURE:

-continued

<223> OTHER INFORMATION: Description of Unknown:
      Rhodospirillaceae bacterium sequence

<400> SEQUENCE: 106

```
Leu Leu Asp Asp Glu Pro Ala Thr Ala Thr Thr Ser Ser Leu Ser Asn
1               5                   10                  15

Leu Val Ala Ala Val Asp Ala Asp Asn Ser Gly Thr Pro Leu Gly Asp
            20                  25                  30

Gly Asn Arg Thr Ile Glu Asp Leu Val Lys Glu Val Met Arg Pro Met
        35                  40                  45

Ile Lys Glu Trp Leu Asp Asp Asn Leu Pro Ala Leu Val Asp Arg Val
    50                  55                  60

Val Arg Arg Glu Ile Glu Arg Leu Ser Arg
65                  70
```

<210> SEQ ID NO 107
<211> LENGTH: 76
<212> TYPE: PRT
<213> ORGANISM: Unknown
<220> FEATURE:
<223> OTHER INFORMATION: Description of Unknown:
      Oleomonas sp. K1W22B-8 sequence

<400> SEQUENCE: 107

```
Ala Glu Arg Leu Val Ser Glu Thr Ile Ala Ser Gln Ala Arg Asn Ala
1               5                   10                  15

Phe Ala Gln Val Ala Gln Ala Ser Arg Pro Pro Ala Gly Thr Arg Arg
            20                  25                  30

Ala Asp Gly Asp Ala Arg Ser Val Glu Glu Val Val Glu Asp Leu Leu
        35                  40                  45

Arg Pro Met Leu Lys Asp Trp Leu Asp Thr His Leu Ala Gly Ile Val
    50                  55                  60

Glu Arg Cys Val Ala Glu Glu Leu Ala Arg Ile Ser
65                  70                  75
```

<210> SEQ ID NO 108
<211> LENGTH: 71
<212> TYPE: PRT
<213> ORGANISM: Ochrobactrum sp.

<400> SEQUENCE: 108

```
Val Ala Pro His Ile Leu Ser Gln Val Ala Glu Arg Gln Val Ala Ala
1               5                   10                  15

Ala Phe Gln Asp Leu Ser His Val Val Arg Ala Glu Pro Arg Arg Ser
            20                  25                  30

Phe Asp Asp Ile Ala Ala Glu Ile Leu Arg Pro Met Leu Gln Asp Trp
        35                  40                  45

Leu Asp Asn Asn Leu Pro Thr Leu Val Glu Arg Leu Val Arg Glu Glu
    50                  55                  60

Ile Glu Arg Val Val Arg Gly
65                  70
```

<210> SEQ ID NO 109
<211> LENGTH: 74
<212> TYPE: PRT
<213> ORGANISM: Unknown
<220> FEATURE:
<223> OTHER INFORMATION: Description of Unknown:
      Ferrovibrio sp. sequence

<400> SEQUENCE: 109

```
Glu Gly Leu Val Ser Pro Pro Thr Ala Ala Arg Ala Ala Ala His Leu
1               5                   10                  15

Gly Gln Leu Ser Gly Ala Ile Ala Gly Ser Arg Ala Met Gly Leu Gly
            20                  25                  30

Asn Ser Gln Arg Thr Leu Glu Glu Leu Val Lys Glu Leu Leu Arg Pro
        35                  40                  45

Met Leu Lys Glu Trp Leu Asp Ala His Leu Ala Thr Ile Val Gln Arg
    50                  55                  60

Ile Val Glu Arg Glu Val Ala Arg Leu Thr
65                  70


<210> SEQ ID NO 110
<211> LENGTH: 71
<212> TYPE: PRT
<213> ORGANISM: Sphingomonas sp.

<400> SEQUENCE: 110

Leu Val Ser Asp Ala Thr Leu Asn Ala Ser Arg Ser Ser Ile Ala Ala
1               5                   10                  15

Leu Ser Ala Leu Val Ile Lys Pro Glu Ile Thr Gly Gly Asp Thr Leu
            20                  25                  30

Glu Gly Leu Val Arg Glu Met Leu Lys Pro Met Leu Ala Asp Trp Leu
        35                  40                  45

Asp Gln Arg Leu Pro Asp Val Val Glu Arg Leu Val Ala Gln Glu Ile
    50                  55                  60

Ser Arg Ile Thr Ala Arg Gly
65                  70


<210> SEQ ID NO 111
<211> LENGTH: 70
<212> TYPE: PRT
<213> ORGANISM: Unknown
<220> FEATURE:
<223> OTHER INFORMATION: Description of Unknown:
      Acidibrevibacterium fodinaquatile sequence

<400> SEQUENCE: 111

Leu Ala Asn Asp Thr Ala Glu Ser Ala Ala Ala Ser Ile Val Gly Leu
1               5                   10                  15

Val Arg Thr Leu Ala Ala Asp Arg Leu Thr Pro Val His Arg Gly Gly
            20                  25                  30

Pro Thr Ile Glu Asp Leu Val Arg Glu Glu Ile Arg Pro Leu Leu Lys
        35                  40                  45

Thr Trp Leu Asp Ala His Leu Pro Ala Leu Val Glu Arg Leu Val Gln
    50                  55                  60

Asn Glu Ile Glu Arg Val
65                  70


<210> SEQ ID NO 112
<211> LENGTH: 75
<212> TYPE: PRT
<213> ORGANISM: Unknown
<220> FEATURE:
<223> OTHER INFORMATION: Description of Unknown:
      Alphaproteobacteria bacterium CG11_big_fil_rev_8_21_14_0
      _20_44_7 sequence

<400> SEQUENCE: 112

Glu Ile Ile Ser Asp Lys Thr Ala Ala Thr Ala Lys Ser Ser Ile Glu
1               5                   10                  15
```

Ser Leu Val Ser Gln Leu Ala Asn Asp Thr Asp Thr Asp Pro Gly Ala
20 25 30

Pro Phe Arg Ser Gly Glu Thr Val Glu Asp Leu Val Lys Glu Met Leu
35 40 45

Lys Pro Met Leu Lys Thr Trp Leu Asp Ala Asn Leu Pro Glu Leu Val
50 55 60

Glu Ala Ile Val Gln Lys Glu Ile Lys Lys Ile
65 70 75

<210> SEQ ID NO 113
<211> LENGTH: 64
<212> TYPE: PRT
<213> ORGANISM: Unknown
<220> FEATURE:
<223> OTHER INFORMATION: Description of Unknown:
Alphaproteobacteria bacterium sequence

<400> SEQUENCE: 113

Ala Thr Thr Ala Thr Ser Asp Ala Phe His Lys Leu Ala Glu Asn Val
1 5 10 15

Ala Ile Ser Arg Gln Val Gly Lys Val Thr Leu Glu Asp Ile Thr Arg
20 25 30

Asp Leu Leu Arg Pro Met Leu Arg Gln Trp Ile His Glu Asn Met Pro
35 40 45

Gln Ile Val Glu Arg Leu Val Gln Lys Glu Leu Glu Lys Ile Ala Lys
50 55 60

<210> SEQ ID NO 114
<211> LENGTH: 68
<212> TYPE: PRT
<213> ORGANISM: Unknown
<220> FEATURE:
<223> OTHER INFORMATION: Description of Unknown:
Phyllobacteriaceae bacterium sequence

<400> SEQUENCE: 114

Leu Met Ser Glu Ala Ser Ser Asp Ala Thr Gln Ala Ala Phe Gly Arg
1 5 10 15

Leu Ala Glu Thr Leu Thr Arg Arg Ala Leu Gly Glu Arg Pro Ile Ala
20 25 30

Asp Val Thr Gln Glu Leu Leu Lys Gly Met Leu Lys Gln Trp Leu Asp
35 40 45

Glu Asn Leu Pro Lys Ile Val Glu Arg Leu Val Arg Glu Glu Ile Glu
50 55 60

Arg Val Val Arg
65

<210> SEQ ID NO 115
<211> LENGTH: 75
<212> TYPE: PRT
<213> ORGANISM: Rhodospirillum rubrum

<400> SEQUENCE: 115

Val Asp Glu Arg Leu Ile Ser Ala Thr Thr Glu Val Ala Ala Gly Gly
1 5 10 15

Leu Leu Ala Glu Leu Ala Ser Ala Val Ala Arg Glu Arg Thr Ile Gly
20 25 30

Leu Gly His Gly Gly Val Thr Leu Glu Asp Met Val Arg Glu Ile Leu
35 40 45

```
Arg Gln Leu Leu Lys Asp Trp Leu Asp Glu Asn Leu Pro Tyr Met Thr
    50                  55                  60

Glu Arg Leu Val Gln Lys Glu Ile Glu Arg Leu
65                  70                  75


<210> SEQ ID NO 116
<211> LENGTH: 69
<212> TYPE: PRT
<213> ORGANISM: Unknown
<220> FEATURE:
<223> OTHER INFORMATION: Description of Unknown:
      Alphaproteobacteria bacterium sequence

<400> SEQUENCE: 116

Ile Leu Asn Asp Ala Ala Ala Thr Ala Thr Val Ser Ser Met Ala Arg
1               5                   10                  15

Leu Ala Glu Asn Ile Ala Val Ser Arg Thr Thr Glu Gly Thr Thr Leu
            20                  25                  30

Glu Asp Ile Thr Arg Asp Leu Leu Arg Pro Met Leu Lys Ile Trp Leu
        35                  40                  45

Asp Glu Asn Leu Pro Thr Val Ile Glu Arg Leu Val Ala Gln Glu Leu
    50                  55                  60

Glu Arg Leu Ala Glu
65


<210> SEQ ID NO 117
<211> LENGTH: 68
<212> TYPE: PRT
<213> ORGANISM: Unknown
<220> FEATURE:
<223> OTHER INFORMATION: Description of Unknown:
      Rhodospirillaceae bacterium sequence

<400> SEQUENCE: 117

Asp Val Ala Ser Leu Leu Asp Ser Val Thr Ala Asp Asn Ala Ser Ala
1               5                   10                  15

Ala Phe Ala Gln Leu Ala Asn Thr Arg Ala Glu Arg Ala Thr Thr Leu
            20                  25                  30

Glu Glu Leu Val Lys Glu Leu Leu Arg Pro Met Leu Lys Thr Trp Leu
        35                  40                  45

Asp Glu Asn Leu Ser Gln Val Val Glu Arg Leu Val Glu Lys Glu Ile
    50                  55                  60

Thr Lys Leu Ser
65


<210> SEQ ID NO 118
<211> LENGTH: 72
<212> TYPE: PRT
<213> ORGANISM: Croceicoccus sp.

<400> SEQUENCE: 118

Ile Ala Gly Ala Thr Ala Ala Ala Met Arg Asp Gln Leu Ser Ala Leu
1               5                   10                  15

Ser Asn Phe Ser Ala Ala Ala Pro Lys Thr Glu Thr Thr Pro His Pro
            20                  25                  30

Leu Glu Asp Ala Val Arg Asp Met Leu Arg Pro Leu Leu Lys Glu Trp
        35                  40                  45

Leu Asp Ala Asn Leu Glu Gly Ile Val Glu Arg Ile Val Gln Asp Glu
    50                  55                  60

Ile Ser Arg Ile Thr Gly Ser Arg
```

65 70

<210> SEQ ID NO 119
<211> LENGTH: 74
<212> TYPE: PRT
<213> ORGANISM: Magnetospirillum sp.

<400> SEQUENCE: 119

Ala Glu Pro Leu Ile Ser Asp Pro Val Ala Arg His Ser Thr Ser Leu
1 5 10 15

Leu Ser Asp Leu Ala Arg Glu Ile Val Arg His Arg Gly Ile Gly Leu
20 25 30

Gly Asn Gly Gly Ile Thr Leu Glu Asp Met Val Arg Glu Leu Leu Lys
35 40 45

Pro Ile Leu Lys Glu Trp Leu Asp Asp Asn Leu Pro Tyr Met Ile Glu
50 55 60

Arg Leu Val Lys Gln Glu Ile Glu Lys Met
65 70

<210> SEQ ID NO 120
<211> LENGTH: 73
<212> TYPE: PRT
<213> ORGANISM: Roseospirillum parvum

<400> SEQUENCE: 120

Asp Ser Leu Leu Ser Pro Arg Ala Ala Asp Ser Ser Ala Thr Ala Leu
1 5 10 15

Ala Glu Leu Ser Ala Ala Val Ala Arg Gly Arg Ala Leu Gly Leu Gly
20 25 30

Ala Gly His Thr Thr Leu Glu Glu Ile Val Lys Glu Leu Leu Arg Pro
35 40 45

Ile Leu Lys Glu Trp Leu Asp Asn His Leu Pro Gly Met Val Glu Arg
50 55 60

Met Val Arg Gln Glu Met Glu Arg Leu
65 70

<210> SEQ ID NO 121
<211> LENGTH: 75
<212> TYPE: PRT
<213> ORGANISM: Unknown
<220> FEATURE:
<223> OTHER INFORMATION: Description of Unknown:
Alphaproteobacteria bacterium CG_4_9_14_3_um_filter_47_13
sequence

<400> SEQUENCE: 121

Glu Asp Gly Asp Ser Ile Phe Thr Asp Ser Ala Glu Asn Ala Ala Leu
1 5 10 15

Gln Gly Phe Met Lys Leu Ala Ser Lys Met Pro Leu Asp Arg Arg Gly
20 25 30

Thr Gly Glu Thr Thr Ile Glu Asp Ile Ile Arg Glu Met Met Lys Pro
35 40 45

Met Leu Arg Glu Trp Leu Asp Ile His Leu Pro Pro Leu Ile Glu Lys
50 55 60

Val Val Gln Lys Glu Leu Arg Asn Ile Ala Arg
65 70 75

<210> SEQ ID NO 122
<211> LENGTH: 70
<212> TYPE: PRT

<213> ORGANISM: Sneathiella glossodoripedis

<400> SEQUENCE: 122

Glu Glu Pro Val Val Gln Ala Ala Thr Ser Ser Phe Ala Ser Leu Ala
1               5                   10                  15

Gly Ala Val Ser Ala Ser Arg Gly Met Pro Met Gly Asn Ser Ala Ala
            20                  25                  30

Thr Leu Glu Glu Leu Val Arg Asp Leu Leu Arg Pro Met Leu Lys Glu
        35                  40                  45

Trp Leu Asp Glu His Leu Ala Ser Ile Val Gln Arg Ile Val Glu Arg
    50                  55                  60

Glu Val Ser Lys Leu Ala
65                  70

<210> SEQ ID NO 123
<211> LENGTH: 80
<212> TYPE: PRT
<213> ORGANISM: Aureimonas sp.

<400> SEQUENCE: 123

Ser Ala Ser Ser Ser Arg Tyr Gly Asp Val Pro Pro Pro Leu Val Ser
1               5                   10                  15

Pro Thr Thr Gly Gln Leu Val Gly Ala Ser Phe Asn Glu Leu Ala Glu
            20                  25                  30

Ala Ile Arg Gln Gly Glu Leu Arg Ser Leu Glu Ala Met Ala Gln Glu
        35                  40                  45

Met Leu Gln Pro Met Leu Arg Asp Trp Leu Asp Asp Asn Leu Pro Lys
    50                  55                  60

Met Val Glu Arg Leu Ile Arg Glu Glu Ile Glu Arg Leu Ala Arg Gly
65                  70                  75                  80

<210> SEQ ID NO 124
<211> LENGTH: 70
<212> TYPE: PRT
<213> ORGANISM: Sphingomonas sp.

<400> SEQUENCE: 124

Leu Val Ser Glu Gln Ala Ala Ser Ala Ser Arg Leu Ser Leu Ala Ala
1               5                   10                  15

Leu Ser Ala Leu Ile Val Ser Pro Ala Ala Glu Pro Ala Arg Asp Asn
            20                  25                  30

Thr Leu Glu Gly Leu Val Arg Glu Met Leu Arg Pro Met Leu Lys Glu
        35                  40                  45

Trp Leu Asp Ala Arg Leu Pro Glu Met Val Glu Gly Leu Val Ala Arg
    50                  55                  60

Glu Ile Ala Arg Ile Thr
65                  70

<210> SEQ ID NO 125
<211> LENGTH: 72
<212> TYPE: PRT
<213> ORGANISM: Aureimonas frigidaquae

<400> SEQUENCE: 125

Ala Glu Pro Leu Ile Ser Glu Thr Ser Glu Ala Ala Ile Gly Ala Ser
1               5                   10                  15

Phe Ala Glu Leu Thr Gln Ala Ile Arg Ala Gly Glu Leu Arg Ser Leu
            20                  25                  30

-continued

```
Glu Glu Met Ala Gln Asp Leu Leu Arg Pro Met Met Arg Glu Trp Leu
        35                  40                  45

Glu Glu Asn Leu Ala Arg Met Val Glu Asp Ile Val Arg Glu Glu Ile
    50                  55                  60

Arg Arg Ala Val Thr Arg Gly Arg
65                  70


<210> SEQ ID NO 126
<211> LENGTH: 75
<212> TYPE: PRT
<213> ORGANISM: Sphingomonas sp.

<400> SEQUENCE: 126

Val Pro Glu Pro Ala Met Leu Leu Ser Lys Gln Thr Gln Ala Ala Ser
1               5                   10                  15

Gln Arg Ala Leu Ala Ala Leu Ser Gly Leu Ser Ile Asp Pro Asn Ala
            20                  25                  30

Asp Ala Asn Thr Met Asp Gly Leu Val Arg Glu Met Leu Arg Pro Met
        35                  40                  45

Leu Lys Asp Trp Leu Asp Ala His Leu Pro Glu Met Val Glu Arg Leu
    50                  55                  60

Val Ala Arg Glu Val Ala Arg Ile Ser Gly Arg
65                  70                  75


<210> SEQ ID NO 127
<211> LENGTH: 65
<212> TYPE: PRT
<213> ORGANISM: Unknown
<220> FEATURE:
<223> OTHER INFORMATION: Description of Unknown:
      Alphaproteobacteria bacterium sequence

<400> SEQUENCE: 127

Gly Val Thr Ala Glu Ala Thr Leu Gly Ala Phe Glu Arg Leu Ala Gln
1               5                   10                  15

Ser Ile Pro Val Asn Arg Pro Gly Thr His Gly His Thr Leu Glu Asp
            20                  25                  30

Ile Val Arg Asp Met Leu Arg Pro Met Leu Arg Gln Trp Val Asp Glu
        35                  40                  45

Asn Met Pro Thr Ile Ala Glu Arg Leu Val Lys Lys Glu Leu Glu Arg
    50                  55                  60

Leu
65


<210> SEQ ID NO 128
<211> LENGTH: 78
<212> TYPE: PRT
<213> ORGANISM: Unknown
<220> FEATURE:
<223> OTHER INFORMATION: Description of Unknown:
      Alteraurantiacibacter aquimixticola sequence

<400> SEQUENCE: 128

Glu Leu Ala Glu Gly Leu Thr Asn Thr Val Ala Ala Asp Ser Met Arg
1               5                   10                  15

Gln Ser Leu Ala Ala Leu Ala Met Leu Ser Glu Pro Ser Ala Lys Pro
            20                  25                  30

Gln Ile Val Arg Ser Gly Glu Thr Ser Leu Glu Asp Met Val Arg Asp
        35                  40                  45

Leu Leu Arg Pro Leu Met Ala Gln Trp Leu Asp Ala His Leu Pro Glu
```

```
    50                  55                  60

Ile Val Glu Arg Leu Val Lys Glu Glu Ile Thr Arg Ile Ala
65                  70                  75


<210> SEQ ID NO 129
<211> LENGTH: 75
<212> TYPE: PRT
<213> ORGANISM: Stappia sp.

<400> SEQUENCE: 129

Ala Thr Glu Leu Met Ser Gln Thr Thr Arg Leu Ala Ala Gly Ala Ala
1               5                   10                  15

Phe Glu Glu Leu Ser Arg Ser Leu Gln Ala Arg Asp Gly Ala Glu Pro
            20                  25                  30

Ser Arg Gly Thr Asn Pro Leu Glu Asp Leu Val Lys Glu Ala Met Arg
        35                  40                  45

Pro Met Leu Arg Glu Trp Leu Asp Ala Asn Leu Asn Gly Ile Val Glu
    50                  55                  60

Arg Leu Val Arg Glu Glu Ile Gln Lys Val Thr
65                  70                  75


<210> SEQ ID NO 130
<211> LENGTH: 78
<212> TYPE: PRT
<213> ORGANISM: Unknown
<220> FEATURE:
<223> OTHER INFORMATION: Description of Unknown:
      Alphaproteobacteria bacterium sequence

<400> SEQUENCE: 130

Asp Pro Leu Val Ser Gly Ser Val Ala Ala Ala Ser Thr Ala Ala Leu
1               5                   10                  15

Gly Arg Leu Ala Gln Thr Val Asn Arg Asp Pro Gly Ser Val Gly Asn
            20                  25                  30

Phe Ser Leu Gly Ala Gly Thr Thr Leu Glu Asp Met Val Arg Asp Met
        35                  40                  45

Val Arg Pro Met Leu Lys Glu Trp Leu Asp Ala Asn Leu Gly Pro Leu
    50                  55                  60

Val Glu Arg Met Val Lys Arg Glu Ile Glu Arg Met Val Arg
65                  70                  75


<210> SEQ ID NO 131
<211> LENGTH: 81
<212> TYPE: PRT
<213> ORGANISM: Unknown
<220> FEATURE:
<223> OTHER INFORMATION: Description of Unknown:
      Caedimonadaceae bacterium sequence

<400> SEQUENCE: 131

Glu Glu Ile Ile Ser Ser Ala Ala Ala His Glu Phe Ala Asn Ala Phe
1               5                   10                  15

Ser Asn Leu Glu Asn Thr Leu Lys Ala Pro Leu Ser Ser Ala Pro Gln
            20                  25                  30

Leu Pro Thr Phe Asp Lys Asn Asn Val Gly Gln Met Thr Leu Glu Met
        35                  40                  45

Ile Val Asn Gln Met Leu Gln Pro Leu Leu Lys Glu Trp Leu Asp Lys
    50                  55                  60

His Leu Pro Ser Leu Val Lys Leu Leu Val Ser Glu Gln Ile Glu Lys
65                  70                  75                  80
```

-continued

Ile

<210> SEQ ID NO 132
<211> LENGTH: 67
<212> TYPE: PRT
<213> ORGANISM: Fulvimarina pelagi

<400> SEQUENCE: 132

Leu Ile Ser Asp Asn Ala Glu Thr Lys Val Ser Ala Ser Phe Ser Glu
1 5 10 15

Leu Ala Ala Val Leu Arg Asp Glu Gln Ala Gln Arg Met Asp Ala Thr
20 25 30

Val Arg Glu Met Leu Gln Pro Met Leu Ser Asp Trp Leu Glu Asp Asn
35 40 45

Leu Pro Ile Ile Val Glu Arg Leu Val Arg Glu Glu Ile Glu Arg Val
50 55 60

Ala Arg Gly
65

<210> SEQ ID NO 133
<211> LENGTH: 79
<212> TYPE: PRT
<213> ORGANISM: Unknown
<220> FEATURE:
<223> OTHER INFORMATION: Description of Unknown:
Alphaproteobacteria bacterium sequence

<400> SEQUENCE: 133

Met Ala Glu Gly Leu Val Ser Arg Asp Thr Glu Ala Ala Ala Thr Arg
1 5 10 15

Ser Phe Ala Gly Leu Gly Ala Thr Val Ser Ala Val Thr Gly Met Pro
20 25 30

Leu Gly His Pro Gln Arg Thr Ile Glu Glu Leu Val Arg Glu Leu Leu
35 40 45

Arg Pro Met Leu Lys Gln Trp Leu Asp Arg Asn Leu Gln Ala Ile Val
50 55 60

Ala Leu Ala Val Glu Arg Glu Ile Ser Cys Leu Ser Gly Arg Ala
65 70 75

<210> SEQ ID NO 134
<211> LENGTH: 82
<212> TYPE: PRT
<213> ORGANISM: Unknown
<220> FEATURE:
<223> OTHER INFORMATION: Description of Unknown:
Caedimonas varicaedens sequence

<400> SEQUENCE: 134

Glu Lys Leu Leu Ser Glu Asp Ala Leu Gln Glu Ser Ala Ser Ala Phe
1 5 10 15

Ala Glu Leu Ala Arg Ala Thr Gln Lys Pro Ala Val Gln Asp Lys Pro
20 25 30

Phe Lys Ile Glu Ser Ala Gly Glu Tyr Thr Val Asp Asn Leu Met Arg
35 40 45

Glu Leu Leu Arg Pro Leu Leu Arg Glu Trp Leu Asp Ala His Leu Pro
50 55 60

Ser Ile Ile Arg Thr Leu Val Ala Glu Gln Ile Glu Lys Thr Leu Gln
65 70 75 80

Gln Arg

```
<210> SEQ ID NO 135
<211> LENGTH: 76
<212> TYPE: PRT
<213> ORGANISM: Acidocella sp.

<400> SEQUENCE: 135

Glu Ser Pro Asp Gly Leu Val Gly Asp Glu Ile Ser Thr Ala Val Val
1               5                   10                  15

Ser Ser Ile Gly Ser Leu Val Asn Ser Ile Asn Asn Glu Arg Ser Val
            20                  25                  30

Thr Ile Ser Arg Ala Gly Val Thr Ile Glu Asp Val Ile Arg Glu Glu
        35                  40                  45

Ile Lys Pro Leu Leu Lys Ala Trp Leu Asn Thr His Leu Pro Val Leu
    50                  55                  60

Val Glu Arg Val Val Arg Ala Glu Ile Ala Arg Val
65                  70                  75


<210> SEQ ID NO 136
<211> LENGTH: 70
<212> TYPE: PRT
<213> ORGANISM: Unknown
<220> FEATURE:
<223> OTHER INFORMATION: Description of Unknown:
      Sphingomonas-like bacterium B12 sequence

<400> SEQUENCE: 136

Glu Gly Leu Leu Ser Ser Thr Ser Ala Glu Ala Ser Arg Ser Ala Phe
1               5                   10                  15

Ala Ala Leu Thr Gln Leu Gln Val Arg Asn Asp Glu Gly Lys Ser Asn
            20                  25                  30

Thr Leu Glu Gly Leu Val Ser Asp Leu Leu Arg Pro Met Leu Lys Glu
        35                  40                  45

Tyr Leu Asp Arg Glu Leu Pro Gly Ile Val Glu Arg Leu Val Ala Val
    50                  55                  60

Glu Val Lys Arg Leu Ala
65                  70


<210> SEQ ID NO 137
<211> LENGTH: 73
<212> TYPE: PRT
<213> ORGANISM: Robiginitomaculum sp.

<400> SEQUENCE: 137

Leu Ser Gly Ala Asp Thr Gln Leu Glu Ala Gly Asn Ala Phe Ala Ser
1               5                   10                  15

Leu Thr Ser Thr Val Gln Lys Gln Ala Val Thr Glu Glu Asn Gly Pro
            20                  25                  30

Pro Ile Gly Glu Leu Val Lys Glu Ala Leu Lys Pro Met Leu Gln Glu
        35                  40                  45

Trp Leu Asp Lys Asn Leu Lys Thr Met Val Gln Arg Ala Val Thr Lys
    50                  55                  60

Glu Ile Lys Arg Ile Ser Thr Gly Lys
65                  70


<210> SEQ ID NO 138
<211> LENGTH: 79
<212> TYPE: PRT
<213> ORGANISM: Unknown
<220> FEATURE:
```

```
<223> OTHER INFORMATION: Description of Unknown:
      Candidatus Finniella inopinata sequence

<400> SEQUENCE: 138

Glu Phe Gln Glu Gly Leu Leu Ser Pro Gln Ala Gln Ala Ala Thr Ile
1               5                   10                  15

Gln Ser Phe Ala Lys Leu Ala Glu Ala Ala His His Val Gln Ser Ala
            20                  25                  30

Pro Lys Ser Glu Pro Thr Ser Pro Thr Leu Asp Gln Leu Ile Gly Glu
        35                  40                  45

Leu Ala Arg Pro Met Val Lys Gln Trp Leu Asp Gln His Leu Pro Arg
    50                  55                  60

Leu Val Glu Leu Thr Val Ala Lys Glu Ile Glu Arg Leu Thr Lys
65                  70                  75


<210> SEQ ID NO 139
<211> LENGTH: 77
<212> TYPE: PRT
<213> ORGANISM: Telmatospirillum siberiense

<400> SEQUENCE: 139

Glu Val Ala Glu Glu Ser Leu Leu Ser Pro Pro Val Gln Ala Ala Ser
1               5                   10                  15

Thr Thr Ala Leu Ala Glu Leu Ala Arg Ala Val Ala Gln Glu Arg Gly
            20                  25                  30

Val Gly Leu Gly Asn Gly Gly Val Thr Leu Glu Glu Ile Val Arg Glu
        35                  40                  45

Ile Leu Lys Ser Leu Ile Lys Asp Trp Leu Asp Gln Asn Leu Pro Tyr
    50                  55                  60

Met Ile Glu Arg Ile Val Lys Lys Glu Ile Glu Lys Met
65                  70                  75


<210> SEQ ID NO 140
<211> LENGTH: 75
<212> TYPE: PRT
<213> ORGANISM: Unknown
<220> FEATURE:
<223> OTHER INFORMATION: Description of Unknown:
      Methylocystaceae bacterium sequence

<400> SEQUENCE: 140

Glu Thr Ser Glu Asp Leu Met Ser Ala Gln Thr Ala Ser Ile Val Ser
1               5                   10                  15

Asp His Phe Glu Ala Leu Ala Ala Arg Ala Leu Val Asp Asn Ser Asp
            20                  25                  30

Met Val Met Ala Leu Thr Gln Gln Leu Met Lys Pro Met Leu Lys Gln
        35                  40                  45

Trp Leu Asp Asp His Leu Pro Glu Ile Val Glu Arg Leu Val Gln Val
    50                  55                  60

Glu Ile Lys Arg Ile Ser Arg Gln Gly Arg Asp
65                  70                  75


<210> SEQ ID NO 141
<211> LENGTH: 84
<212> TYPE: PRT
<213> ORGANISM: Kozakia baliensis

<400> SEQUENCE: 141

Glu Ser Leu Leu Gly Thr Ser Ala Lys Ala Ala Met Asp Arg Ser Leu
1               5                   10                  15
```

```
Glu Ser Leu Asn Thr Ala Leu Glu Gln Gln Ala Ala Pro Arg His Thr
            20                  25                  30

Leu Thr Ala Thr Thr Arg Ile Ser Asn Gly Thr Ser Ser Ser Ile Glu
        35                  40                  45

Asp Ile Val Arg Glu Glu Val Arg Glu Met Val Arg Ser Trp Leu Asp
    50                  55                  60

Thr Asn Leu Pro Ser Met Val Glu Asn Met Val Arg Ala Glu Ile Thr
65                  70                  75                  80

Arg Met Thr Arg


<210> SEQ ID NO 142
<211> LENGTH: 73
<212> TYPE: PRT
<213> ORGANISM: Micavibrio sp.

<400> SEQUENCE: 142

Glu Asp Ile Leu Thr Glu Ala Ala Lys Thr Ala Ala Leu Ser Ser Met
1               5                   10                  15

Ala Lys Leu Ala Gly Asn Met Pro Ile Thr Arg His Arg Glu Tyr Gly
            20                  25                  30

Asn Ile Thr Leu Glu Asp Leu Val Arg Glu Met Leu His Pro Met Leu
        35                  40                  45

Arg Asp Trp Val Ser Glu Asn Leu Pro Ser Met Val Glu Arg Leu Val
    50                  55                  60

Gln Lys Glu Leu Glu Lys Leu Ala Arg
65                  70


<210> SEQ ID NO 143
<211> LENGTH: 85
<212> TYPE: PRT
<213> ORGANISM: Novosphingobium lentum

<400> SEQUENCE: 143

Asp Ala Ala Ala Glu Glu Ala Gly Leu Leu Pro Glu Ala Ala Ala Ala
1               5                   10                  15

Ser Met Arg Asp Ser Leu Thr Ala Leu Ala Met Leu Ala Glu Pro Gly
            20                  25                  30

Ala Ser Pro Gln Ile Val Arg Ser Gly Glu Thr Ser Leu Glu Gly Leu
        35                  40                  45

Ala Arg Glu Leu Met Arg Pro Met Leu Ala Glu Trp Leu Glu Asn Asn
    50                  55                  60

Leu Pro Ala Met Val Glu Lys Met Val Ala Ala Glu Ile Ala Arg Ile
65                  70                  75                  80

Ala Gly Lys Lys Gly
                85


<210> SEQ ID NO 144
<211> LENGTH: 77
<212> TYPE: PRT
<213> ORGANISM: Micavibrio sp.

<400> SEQUENCE: 144

Asp Val Ser Glu Asp Asn Ser Glu Ile Ile Ser Asp Arg Ala Ala Glu
1               5                   10                  15

Glu Ala Val Gly Ala Leu Ser Lys Leu Ala Gln Asn Val Ala Leu Ser
            20                  25                  30

Asn Arg Ser Ala Asp Val Thr Leu Glu Asp Ile Val Lys Glu Leu Val
```

```
        35                  40                  45

Arg Pro Met Leu Arg Gln Trp Ile Asn Glu Asn Met Ser Asp Ile Val
    50                  55                  60

Glu Ala Leu Val Glu Lys Glu Leu Glu Lys Leu Val Arg
65                  70                  75


<210> SEQ ID NO 145
<211> LENGTH: 78
<212> TYPE: PRT
<213> ORGANISM: Unknown
<220> FEATURE:
<223> OTHER INFORMATION: Description of Unknown:
      Alphaproteobacteria bacterium sequence

<400> SEQUENCE: 145

Ser Glu Gly Leu Val Ser Arg Glu Ala Ala Glu Gln Thr Ala Ala Ala
1               5                   10                  15

Phe Val Asp Phe Ala Ser Ala Val Ser Ser Ala Gln Gly Val Gln Leu
            20                  25                  30

Gly Ala Ser His Arg Thr Leu Glu Glu Leu Val Lys Glu Ser Leu Arg
        35                  40                  45

Pro Met Leu Lys Val Trp Leu Asp Asn Asn Leu Gln Pro Ile Val Ser
    50                  55                  60

Arg Thr Val Glu Arg Glu Ile Ala Lys Leu Ala Gly Arg Ala
65                  70                  75


<210> SEQ ID NO 146
<211> LENGTH: 73
<212> TYPE: PRT
<213> ORGANISM: Roseospira marina

<400> SEQUENCE: 146

Leu Val Glu Ala Ser Val Ala Ala Val Ser Ser Gln Tyr Leu Ser Thr
1               5                   10                  15

Leu Thr Asp Ser Leu Gln Gly Arg Asp Ile Pro Ile Gly Asn Gly Ala
            20                  25                  30

Ile Thr Leu Glu Gly Leu Val Arg Gln Ile Val Arg Glu Leu Val Lys
        35                  40                  45

Gln Trp Leu Asp Glu Asn Leu Pro Glu Met Thr Glu Arg Leu Val Glu
    50                  55                  60

Arg Glu Ile Gln Arg Leu Ala Lys Ser
65                  70


<210> SEQ ID NO 147
<211> LENGTH: 79
<212> TYPE: PRT
<213> ORGANISM: Unknown
<220> FEATURE:
<223> OTHER INFORMATION: Description of Unknown:
      Nitrospirillum amazonense sequence

<400> SEQUENCE: 147

Asp Arg Leu Met Ser Gln Phe Thr Glu Glu Ala Ala Ser Arg Ala Phe
1               5                   10                  15

Ser Ser Leu Ser Gly Phe Arg Arg Gly Gly Pro Ser Leu Thr Gly Glu
            20                  25                  30

Gly Pro Ile Gly Arg Ser Asp Val Thr Leu Glu Glu Ile Val His Val
        35                  40                  45

Leu Val Arg Pro Ile Leu Arg Glu Trp Leu Asp Glu Asn Leu Pro Ser
    50                  55                  60
```

```
Leu Val Glu Arg Leu Val Lys Arg Glu Ile Glu Lys Val Val Arg
65                  70                  75


<210> SEQ ID NO 148
<211> LENGTH: 75
<212> TYPE: PRT
<213> ORGANISM: Unknown
<220> FEATURE:
<223> OTHER INFORMATION: Description of Unknown:
      Geminicoccaceae bacterium sequence

<400> SEQUENCE: 148

Leu Thr Glu Val Leu Leu Asp Ser Gly Thr Ser Ser Ile Ala Ser Ser
1               5                   10                  15

Ala Leu Gln Arg Leu Ser Ala Ala Ile Ala Pro Gly Asp Ala Val Ala
            20                  25                  30

Gly Gly Gln Arg Ser Ile Glu Val Phe Leu Ala Asp Leu Val Arg Pro
        35                  40                  45

Glu Leu Lys Ala Trp Leu Asp Thr Asn Leu Pro Pro Leu Val Glu Arg
    50                  55                  60

Ile Val Glu Arg Glu Ile Lys Lys Leu Val Arg
65                  70                  75


<210> SEQ ID NO 149
<211> LENGTH: 88
<212> TYPE: PRT
<213> ORGANISM: Unknown
<220> FEATURE:
<223> OTHER INFORMATION: Description of Unknown:
      Lichenicoccus roseus sequence

<400> SEQUENCE: 149

Glu Glu Leu Ile Ala Ala Arg Thr Arg Ala Ala Thr Glu Gln Ser Phe
1               5                   10                  15

Asp Ala Leu His Ala Ala Leu Lys Arg Glu Glu Ala Ala Asn Ala Pro
            20                  25                  30

Pro Ala Ala Pro Ser Pro Met Leu Leu Arg Gly Gly Gly Pro Ser Leu
        35                  40                  45

Glu Asp Met Val Arg Gln Glu Leu Arg Gly Leu Leu Ser Ala Trp Leu
    50                  55                  60

Asp Glu His Leu Pro Gly Leu Val Glu Ala Leu Val Arg Ser Gln Ile
65                  70                  75                  80

Glu Lys Met Val Arg Arg Gly Ser
                85


<210> SEQ ID NO 150
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Asp Asp Ala Pro Ala Glu Pro Ala Ala Glu Ala Ala Pro Pro Pro Pro
1               5                   10                  15

Pro Glu Pro Glu Pro Glu Pro Val Ser Phe Asp Asp Glu Val Leu Glu
            20                  25                  30

Leu Thr Asp Pro Ile Ala Pro Glu Pro Glu Leu Pro Pro Leu Glu Thr
        35                  40                  45
```

```
Val Gly Asp Ile Asp Val Tyr Ser Pro Pro Glu Pro Glu Ser Glu Pro
    50                  55                  60

Ala Tyr Thr Pro Pro Pro Ala Ala Pro Val Phe Asp Arg Asp Asp Asp
65                  70                  75                  80

Ala Pro Ala Glu Pro Ala Ala Glu Ala Ala Pro Pro Pro Pro Pro Glu
                85                  90                  95

Pro Glu Pro Glu Pro Val Ser Phe Asp Asp Glu Val Leu Glu Leu Thr
            100                 105                 110

Asp Pro Ile Ala Pro Glu Pro Glu Leu Pro Pro Leu Glu Thr Val Gly
        115                 120                 125

Asp Ile Asp Val Tyr Ser Pro Pro Glu Pro Glu Ser Glu Pro Ala Tyr
    130                 135                 140

Thr Pro Pro Pro Ala Ala Pro Val Phe Asp Arg Asp
145                 150                 155


<210> SEQ ID NO 151
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Gly Gly Gly Ser Gly Gly Gly Gly Ser Gly Gly Gly Gly Ser Gly
1               5                   10                  15

Gly Gly Gly Ser
            20


<210> SEQ ID NO 152
<211> LENGTH: 178
<212> TYPE: PRT
<213> ORGANISM: Unknown
<220> FEATURE:
<223> OTHER INFORMATION: Description of Unknown:
      PopZ sequence

<400> SEQUENCE: 152

Met Ser Asp Gln Ser Gln Glu Pro Thr Met Glu Glu Ile Leu Ala Ser
1               5                   10                  15

Ile Arg Arg Ile Ile Ser Glu Asp Asp Ala Pro Ala Glu Pro Ala Ala
            20                  25                  30

Glu Ala Ala Pro Pro Pro Pro Pro Glu Pro Glu Pro Glu Pro Val Ser
        35                  40                  45

Phe Asp Asp Glu Val Leu Glu Leu Thr Asp Pro Ile Ala Pro Glu Pro
    50                  55                  60

Glu Leu Pro Pro Leu Glu Thr Val Gly Asp Ile Asp Val Tyr Ser Pro
65                  70                  75                  80

Pro Glu Pro Glu Ser Glu Pro Ala Tyr Thr Pro Pro Pro Ala Ala Pro
                85                  90                  95

Val Phe Asp Arg Asp Glu Val Ala Glu Gln Leu Val Gly Val Ser Ala
            100                 105                 110

Ala Ser Ala Ala Ala Ala Ser Ala Phe Gly Ser Leu Ser Ser Ala Leu
        115                 120                 125
```

-continued

```
Leu Met Pro Lys Asp Gly Arg Thr Leu Glu Asp Val Val Arg Glu Leu
    130                 135                 140

Leu Arg Pro Leu Leu Lys Glu Trp Leu Asp Gln Asn Leu Pro Arg Ile
145                 150                 155                 160

Val Glu Thr Lys Val Glu Glu Glu Val Gln Arg Ile Ser Arg Gly Arg
                165                 170                 175

Gly Ala
```